(12) United States Patent
Carroll et al.

(10) Patent No.: US 8,735,434 B2
(45) Date of Patent: May 27, 2014

(54) COMPOUNDS AS CANNABINOID RECEPTOR LIGANDS

(75) Inventors: William A. Carroll, Evanston, IL (US); Michael J. Dart, Highland Park, IL (US); Arturo Perez-Medrano, Grayslake, IL (US); Jennifer M. Frost, Grayslake, IL (US); Sridhar Peddi, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 161 days.

(21) Appl. No.: 12/120,969

(22) Filed: May 15, 2008

(65) Prior Publication Data

US 2008/0287510 A1    Nov. 20, 2008

Related U.S. Application Data

(60) Provisional application No. 60/938,838, filed on May 18, 2007.

(51) Int. Cl.
*A61K 31/429* (2006.01)
*C07D 513/04* (2006.01)

(52) U.S. Cl.
CPC ............ *A61K 31/429* (2013.01); *C07D 513/04* (2013.01)
USPC ............ 514/367; 548/147; 548/151; 548/153

(58) Field of Classification Search
USPC .................................. 548/151, 153
See application file for complete search history.

(56) References Cited

U.S. PATENT DOCUMENTS

| | | | |
|---|---|---|---|
| 3,843,683 A | 10/1974 | Bell | |
| 3,928,327 A | 12/1975 | Takamizawa et al. | |
| 4,885,295 A | 12/1989 | Bell | |
| 4,966,828 A | 10/1990 | Doenges et al. | |
| 4,973,587 A | 11/1990 | Ward et al. | |
| 4,978,664 A | 12/1990 | Bell | |
| 5,013,837 A | 5/1991 | Ward et al. | |
| 5,055,579 A | 10/1991 | Pawlowski et al. | |
| 5,250,498 A | 10/1993 | Andree et al. | |
| 5,468,722 A | 11/1995 | Shibata et al. | |
| 5,530,019 A | 6/1996 | Okada et al. | |
| 5,654,322 A | 8/1997 | Hirata et al. | |
| 6,323,214 B1 | 11/2001 | Baraldi | |
| 6,358,992 B1 | 3/2002 | Pamukcu et al. | |
| 6,369,052 B1 | 4/2002 | Kellar et al. | |
| 6,559,186 B1 | 5/2003 | Campbell | |
| 7,511,013 B2 | 3/2009 | Molino et al. | |
| 7,514,068 B2 | 4/2009 | Tung | |
| 7,521,421 B2 | 4/2009 | Naicker et al. | |
| 7,528,131 B2 | 5/2009 | Persichetti et al. | |
| 7,531,685 B2 | 5/2009 | Czarnik | |
| 7,534,814 B2 | 5/2009 | Ascher et al. | |
| 7,538,189 B2 | 5/2009 | Naicker et al. | |
| 7,560,456 B2 | 7/2009 | Araki et al. | |
| 7,560,481 B2 | 7/2009 | Frost et al. | |
| 7,674,912 B2 | 3/2010 | Sams et al. | |
| 7,683,084 B2 | 3/2010 | Faghih et al. | |
| 7,750,039 B2 | 7/2010 | Frost et al. | |
| 7,868,038 B2 | 1/2011 | Nelson et al. | |
| 7,872,006 B2 | 1/2011 | Moritani et al. | |
| 7,872,033 B2 | 1/2011 | Carroll et al. | |
| 7,875,639 B2 | 1/2011 | Florjancic et al. | |
| 7,875,640 B2 * | 1/2011 | Kolasa et al. ................. 514/370 |
| 7,985,768 B2 | 7/2011 | Nelson et al. | |
| 8,044,071 B2 | 10/2011 | Carroll | |
| 8,058,293 B2 | 11/2011 | Kolasa et al. | |
| 8,158,663 B2 | 4/2012 | Carroll et al. | |
| 8,173,687 B2 | 5/2012 | Carroll et al. | |
| 8,236,822 B2 | 8/2012 | Wang et al. | |
| 8,288,428 B2 | 10/2012 | Wang et al. | |
| 8,338,467 B2 | 12/2012 | Kolasa et al. | |
| 8,481,574 B2 | 7/2013 | Meyer et al. | |
| 8,492,371 B2 | 7/2013 | Carroll et al. | |
| 8,501,794 B2 | 8/2013 | Carroll et al. | |
| 8,586,596 B2 | 11/2013 | Dart et al. | |

(Continued)

FOREIGN PATENT DOCUMENTS

| | | | |
|---|---|---|---|
| CA | 2587667 A1 | 5/2006 | |
| DE | 1522361 A1 | 7/1969 | |

(Continued)

OTHER PUBLICATIONS

Rautio et al. Nature Reviews Drug Discovery 2008, 7, pp. 255-270.*
Wang et al. Drug Delivery: Principles and Applications, 2005 John Wiley & Sons, Inc. Publication, Section 8.3, pp. 136-137.*
Smith, D. A. Current Opinion in Drug Discovery & Development 2007, 10, 550-559.*
Testa, B. Current Opinion in Chemical Biology 2009, 13, pp. 338-344.*
CAPLUS Record of U.S. Patent Application Publication No. 2008/0242654 by Kolasa et al., 2008.*
CAPLUS Record of U.S. Patent Application Publication No. 2008/0058335 by Westheim et al., 2007.*
Giron, D. J. Therm. Anal. Cal. 2001, 64, pp. 37-60.*
Giron, D. J. Therm. Anal. Cal. 2002, 68, pp. 335-357.*
B. Rodriquez-Spong et al. Advanced Drug Delivery Reviews, 2004, 56, pp. 241-274.*

(Continued)

*Primary Examiner* — Joseph Kosack
*Assistant Examiner* — Matthew Coughlin
(74) *Attorney, Agent, or Firm* — Lisa V. Mueller; Michael Best & Friedrich LLP

(57) ABSTRACT

The present application relates to thiazolylidene containing compounds of formula (I)

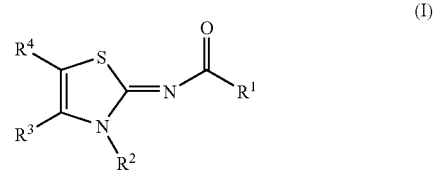

wherein $R^1$, $R^2$, $R^3$, and $R^4$ are as defined in the specification. The present application also relates to compositions comprising such compounds, and methods of treating conditions and disorders using such compounds and compositions.

20 Claims, No Drawings

(56) References Cited

U.S. PATENT DOCUMENTS

| | | |
|---|---|---|
| 2004/0023862 A1 | 2/2004 | Smart et al. |
| 2004/0029040 A1 | 2/2004 | Watanabe et al. |
| 2004/0034090 A1 | 2/2004 | Barth et al. |
| 2004/0077617 A1 | 4/2004 | Bennani et al. |
| 2004/0166539 A1 | 8/2004 | Akhavan-Tafti et al. |
| 2004/0259912 A1 | 12/2004 | Matsumoto et al. |
| 2005/0176713 A1 | 8/2005 | Freyne et al. |
| 2006/0199817 A1 | 9/2006 | Tasker et al. |
| 2007/0155738 A1 | 7/2007 | Steeneck et al. |
| 2008/0058335 A1* | 3/2008 | Florjancic et al. ......... 514/236.8 |
| 2008/0058355 A1* | 3/2008 | Westheim ................. 514/266.4 |
| 2008/0139635 A1 | 6/2008 | Martin et al. |
| 2008/0242654 A1* | 10/2008 | Kolasa et al. ............. 514/210.2 |
| 2008/0287510 A1 | 11/2008 | Carroll et al. |
| 2008/0312435 A1 | 12/2008 | Saito et al. |
| 2009/0082471 A1 | 3/2009 | Czarnik |
| 2009/0088416 A1 | 4/2009 | Czarnik |
| 2009/0093422 A1 | 4/2009 | Tung et al. |
| 2009/0105147 A1 | 4/2009 | Masse |
| 2009/0105305 A1 | 4/2009 | Butlin et al. |
| 2009/0105306 A1 | 4/2009 | Carroll et al. |
| 2009/0105307 A1 | 4/2009 | Galley et al. |
| 2009/0105338 A1 | 4/2009 | Czarnik |
| 2009/0111840 A1 | 4/2009 | Herold et al. |
| 2009/0118238 A1 | 5/2009 | Czarnik |
| 2009/0131363 A1 | 5/2009 | Harbeson |
| 2009/0131485 A1 | 5/2009 | Liu et al. |
| 2009/0137457 A1 | 5/2009 | Harbeson |
| 2010/0041720 A1 | 2/2010 | Carroll et al. |
| 2010/0063022 A1 | 3/2010 | Carroll et al. |
| 2010/0069348 A1 | 3/2010 | Carroll et al. |
| 2010/0069349 A1 | 3/2010 | Carroll et al. |
| 2010/0093814 A1 | 4/2010 | Florjancic et al. |
| 2010/0216760 A1 | 8/2010 | Frost |
| 2011/0065685 A1 | 3/2011 | Frost et al. |
| 2011/0082116 A1 | 4/2011 | Carroll et al. |
| 2011/0086832 A1* | 4/2011 | Kolasa et al. ............. 514/210.2 |
| 2011/0086838 A1 | 4/2011 | Nelson et al. |

FOREIGN PATENT DOCUMENTS

| | | |
|---|---|---|
| DE | 1772867 A1 | 6/1971 |
| DE | 2458933 A1 | 6/1975 |
| DE | 3533331 A1 | 3/1987 |
| EP | 412404 A2 | 2/1991 |
| EP | 568096 A1 | 11/1993 |
| EP | 0619316 A1 | 10/1994 |
| EP | 0639569 A1 | 2/1995 |
| EP | 1060734 A2 | 12/2000 |
| EP | 1219612 A1 | 7/2002 |
| EP | 1300401 A1 | 4/2003 |
| EP | 1640369 A1 | 3/2006 |
| EP | 1820504 A1 | 8/2007 |
| FR | 2796643 A1 | 1/2001 |
| JP | S57171986 A | 10/1982 |
| JP | 6345736 A | 12/1994 |
| WO | WO9507271 A1 | 3/1995 |
| WO | 9531448 A1 | 11/1995 |
| WO | 9601591 A1 | 1/1996 |
| WO | 9700860 A1 | 1/1997 |
| WO | WO9710223 A1 | 3/1997 |
| WO | 0063207 A1 | 10/2000 |
| WO | 0116138 A1 | 3/2001 |
| WO | 0128557 A1 | 4/2001 |
| WO | 0155139 A1 | 8/2001 |
| WO | 0155140 A1 | 8/2001 |
| WO | 0183422 A1 | 11/2001 |
| WO | 0242269 A1 | 5/2002 |
| WO | 02060447 A1 | 8/2002 |
| WO | 02102232 A2 | 12/2002 |
| WO | 03049741 A1 | 6/2003 |
| WO | 03097605 A1 | 11/2003 |
| WO | 2004050086 A1 | 6/2004 |
| WO | 2004110453 A1 | 12/2004 |
| WO | 2005023818 A2 | 3/2005 |
| WO | WO2005058887 A1 | 6/2005 |
| WO | 2005075464 A1 | 8/2005 |
| WO | 2005099353 A3 | 10/2005 |
| WO | WO2005099353 A2 | 10/2005 |
| WO | 2005115972 A1 | 12/2005 |
| WO | 2005115986 A1 | 12/2005 |
| WO | WO2006008754 A1 | 1/2006 |
| WO | 2006051704 A1 | 5/2006 |
| WO | WO-2006051704 A1 | 5/2006 |
| WO | 2006070106 A1 | 7/2006 |
| WO | WO2006100208 A1 | 9/2006 |
| WO | 2007061360 A2 | 5/2007 |
| WO | WO-2007140385 A2 | 12/2007 |
| WO | WO2007140439 A2 | 12/2007 |
| WO | WO2007140439 A3 | 1/2008 |
| WO | WO2007140385 A3 | 2/2008 |
| WO | 2008063781 A2 | 5/2008 |
| WO | WO2008079687 A1 | 7/2008 |
| WO | 2008130953 A2 | 10/2008 |
| WO | WO 2008121558 A1 * | 10/2008 |
| WO | WO2008144360 A1 | 11/2008 |
| WO | 2009009550 A1 | 1/2009 |
| WO | WO2009048936 A1 | 4/2009 |
| WO | WO 2009067613 A1 * | 5/2009 |
| WO | WO2009067613 A1 | 5/2009 |
| WO | WO2009114566 A1 | 9/2009 |
| WO | 2010019547 A1 | 2/2010 |
| WO | 2010033543 A2 | 3/2010 |
| WO | 2010054024 A2 | 5/2010 |
| WO | 2010071783 A1 | 6/2010 |
| WO | 2010111573 A1 | 9/2010 |
| WO | 2010111574 A1 | 9/2010 |

OTHER PUBLICATIONS

Souillac, et al., Characterization of Delivery Systems, Differential Scanning Calorimetry, pp. 217-218 (in Encyclopedia of Controlled Drug Delivery, 1999, John Wiley & Sons, pp. 212-227).*
CAplus entry for WO 2009067613 A1, 2009.*
Ex Parte Cai et al., Appeal No. 2011-005302, Decided Dec. 7, 2011.*
"IUPAC Commission on Nomenclature of Organic Chemistry—Rules for the Nomenclature of Organic Chemistry, Section E: Stereochemistry (Recommendations 1974)," Pure Appl Chem, 1976, 13-30, vol. 45.
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.
Berge, S.M. et al., "Journal of Pharmaceutical Sciences, Pharmaceutical Salts," J Pharmaceutical Sciences, 1977, 1-19, vol. 66.
Bouchard, J-F et al., "Contribution of endocannabinoids in the endothelial protection afforded by ischemic preconditioning in the isolated rat heart", Life Sciences, 2003, 1859-1870, vol. 72.
Boyle, W.J. et al., "Osteoclast differentiation and activation," (Binary/Image), 2003, 337-342, vol. 423.
Brennan, T.J. et al., "Characterization of a rat model of incisional pain," (Binary/Image), 1996, 493-501, vol. 64.
Buckley, N.E. et al., "Immunomodulation by cannabinoids is absent in mice deficient for the cannabinoid CB receptor," European Journal of Pharmacology, 2000, 141-149, vol. 396.
Carrier, E.J. et al., "Endocannabinoids in Neuroimmunology and Stress," Current Drug Targets—CNS & Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Clayton, N. et al., "CB1 and CB2 cannabinoid receptors are implicated in inflammatory pain," (Binary/Image), 2002, 253-260, vol. 96.
Dixon, W.J. "Efficient analysis of experimental observations," Annual Review of Pharmacology and Toxicology, 1980, 441-462, vol. 20.

(56) References Cited

OTHER PUBLICATIONS

Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.
Galiégue, et al., "Expression of central and peripheral cannabinoid receptors in human immune tissues and leukocyte subpopulations," European Journal of Biochemistry, 1995, 54-61, vol. 232.
Greene, T.W. et al., "Protective Groups in Organic Synthesis", 1999, 3 rd Ed, 494-653.
Grotenhermen, F. et al., "IACM 2nd Conference on Cannabinoids in Medicine," Expert Opinion in Pharmacotherapy, 2003, 2367-2371, vol. 4—Issue 12.
Hanus, L. et al., "HU-308: A specific agonist for CB 2, a peripheral cannabinoid receptor," Proceedings of the National Academy of Science, 1999, 14228-14233, vol. 96.
Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.
Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.
Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.
Ihenetu, K. et al., "Inhibition of interleukin-8 release in the human colonic epithelial cell line HT-29 by cannabinoids," European Journal of Pharmacology, 2003, 207-215, vol. 458.
International Search Report for application No. PCT/US08/063648, Mailed on Aug. 13, 2008, 3 pages.
Joshi S.K. et al., "Comparison of Antinociceptive Actoins of Standard Analgesics in Attenuating Capsaicin and Nerve-Injury-Induced Mechanical Hypersensitivty," Neurosci, 587-596, vol. 143, 2006.
Julien, B, et al., "Antifibrogenic Role of the Cannabinoid Receptor CB2 in the Liver," Gastroenterology, 2005, 742-755, vol. 128.
Karsak, M, et al., "Cannabinoid receptor type 2 gene is associated with human osteoporosis," Human Molecular Genetics, 2005, 3389-3396, vol. 14—Issue 22.
Kim, S.H. & Chung, J.M. "An experimental model for peripheral neuropathy produced by segmental spinal nerve ligation in the rat," (Binary/Image), 1992, 355-363, vol. 50—Issue 3.
Lepicier, P. et al., "Endocannabinoids protect the rat isolated heart against ischaemia," British Journal of Pharmacology, 2003, 805-815, vol. 139.
Li W., Wayne G.S., Lallaman J.E., Chang S.J., Wittenberger S.J., "An improved synthesis of pyran-3,5-dione: application to the synthesis of ABT-598, a potassium channel opener, via Hantzsch reaction," J Org Chem, 2006, 1725-1727, 71/4.
Lotersztajn, S. et al., "Hepatic Fibrosis: Molecular Mechanisms and Drug Targets," Annual Review of Pharmacology and Toxicology, 2005, 605-628, vol. 45.
Malan, T.P. et al., "CB2 cannabinoid receptor-mediated peripheral antinociception," (Binary/Image), 2001, 239-245, vol. 93.
Maresz, K, et al., "Modulation of the cannabinoid CB2 receptor in microglial cells in response to inflammatory stimuli," Journal of Neurochemistry, 2005, 437-445, vol. 95.
Mathison, R, et al., "Effects of cannabinoid receptor-2 activation on accelerated gastrointestinal transit in lipopolysaccharide-treated rats," British Journal of Pharmacology, 2004, 1247-1254, vol. 142.
McKallip, R.J. et al., "Targeting CB2 cannabinoid receptors as a novel therapy to treat malignant lymphoblastic disease," (Binary/Image), 2002, 627-634, vol. 15—Issue 2.
Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.
Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.
Pertwee, R.G. "Cannabinoids and multiple sclerosis," Pharmacology & Therapeutics, 2002, 165-174, vol. 95.
Prescott et al., Methods in Cell Biology, 1976, vol. XIV, 33, Academic Press.
Quartilho, A. et al., "Inhibition of Inflammatory Hyperalgesia by Activation of Peripheral CB2 Cannabinoid Receptors," Anesthesiology, 2003, 955-960, vol. 99.
Ralston, S.H. "Regulation of bone mass, bone loss and osteoclast activity by cannabinoid receptors," Nature Medicine, 2005, 774-779, vol. 11.
Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.
Sanchez C. et al., "Inhibition of Glioma Growth in Vivo by Selective Activation of the CB2 Cannabinoid Receptor1," Cancer Research, 2001, 5784-5789, vol. 61.
Steffens S. et al., "Low dose oral cannabinoid therapy reduces progression of atherosclerosis in mice," (Binary/Image), 2005, 782-786, vol. 434.
Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.
Warhurst A.C. et al., "Interferon ? induces differential upregulation of $a$ and $\beta$ chemokine secretion in colonic epithelial cell lines," (Binary/Image), 1998, 208-213, vol. 42.
Wright K. et al., "Differential Expression of Cannabinoid Receptors in the Human Colon: Cannabinoids Promote Epithelial Wound Healing," Gastroenterology, 2005, 437-453, vol. 129.
Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.
Yoshihara S. et al., "Endogenous Cannabinoid Receptor Agonists Inhibit Neurogenic Inflammations in Guinea Pig Airways" Allergy and Immunology, 2005, 80-87, vol. 138.
Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.
Abreo, et al., "Novel 3-Pyridyl Ethers with Subnanomolar Affinity for Central Neuronal Nicotonic Acetylcholine Receptors," Journal of Medicinal Chemistry, 1996, vol. 39 (4), pp. 817-825.
Ambartsumova, et al., "Effect of Various Factors on the Reaction of 2-Aminobenzothiazoles with Propylene Oxide," Chemistry of Heterocyclic Compounds, 2002, vol. 38 (8), pp. 994-999.
Araki, et al., (2003): STN International HCAPLUS database, (Columbus, OH). Accession No. 2003-931334.
Baker, et al., "Regiospecific Vinyl Phosphate/β-Keto Phosphonate Rearrangements Initiated by Halogen-Metal Exchange," Journal of Organic Chemistry, 1998, vol. 63 (8), pp. 2613-2618.
Benito, et al., "A Glial Endogenous Cannabinoid System is Upregulated in the Brains of Macaques with Simian Immunodeficiency Virus-Induced Encephalitis," Journal of Neuroscience, 2005, vol. 25 (10), pp. 2530-2536.
Bennett, et al., "A Peripheral Mononeuropathy in Rat that Produces Disorders of Pain Sensation like those Seen in Man," Pain, 1988, vol. 33 (1), pp. 87-107.
Beylot, et al., "In Vivo Studies of Intrahepatic Metabolic Pathways," Diabetes Metabolism, 1997, vol. 23 (3), pp. 251-257.
Blagojevic, et al., "Role of heavy water in Boron Neutron Capture Therapy," Topics in Dosimetry & Treatment Planning for Neutron Capture Therapy, 1994, pp. 125-134.
Blake, et al., "Studies With Deuterated Drugs," Journal of Pharmaceutical Sciences, 1975, vol. 64 (3), pp. 367-391.

(56) References Cited

OTHER PUBLICATIONS

Bozidar, et al., "Transformations of 1,2,4-Thiadiazolo/2,3-X/ Azines," Heterocycles, 1987, vol. 26 (3), pp. 689-697.
Bozidar, et al., "Transformations of 1-(2-Chloropyridyl-3)-4-ethoxycarbonyland 1-(2-Chloropyridyl-3)-4-ethoxycarbonylmethyl Thiosemicarbazides. Attempts to Prepare Pyrido [3,2-e]-1,2,4-thiadiazine," Monatshefte Fur Chemie, 1988, vol. 119, pp. 333-339.
Brickner, et al., "Synthesis and Antibacterial Activity of U-100592 and U-100766, Two Oxazolidinone Antibacterial Agents for the Potential Treatment of Multidrug-Resistant Gram-Positive Bacterial Infections," Journal of Medicinal Chemistry, 1996, vol. 39 (3), pp. 673-679.
CAPLUS Record of U.S. Patent Application Publication No. 2008/0058335 by Westheim, et al., 2007.
CAPLUS Record of U.S. Patent Application Publication No. 2008/0242654 by Kolasa, at al., 2008.
Carlisle, et al., "Differential Expression of the CB2 Cannabinoid Receptor by Rodent Macrophages and Macrophage-like Cells in Relation to Cell Activation," International Immunopharmacology, 2002, vol. 2, pp. 69.
Cichewicz, D., "Synergistic Interactions Between Cannabinoid and Opioid Analgesics," Life Sciences, 2004, vol. 74 (11), pp. 1317-1324.
Czajka, et al., "Effect of Deuterium Oxide on the Reproductive Potential of Mice," Annals of the New York Academy of Sciences, 1960, vol. 84, pp. 770-779.
Czajka, et al., "Physiological Effects of Deuterium on Dogs," American Journal of Physiology, 1961, vol. 201 (2), pp. 357-362.
Dart, et al (2007): STN International HCAPLUS database, Columbus (OH), Accession No. 2007:1396538.
Final Office Action mailed Mar. 10, 2010 for U.S. Appl. No. 11/755,434, filed May 30, 2007.
Final Office Action mailed Sep. 14, 2011 for U.S. Appl. No. 12/274,105, filed Nov. 19, 2008.
Final Office Action mailed Nov. 16, 2011 for U.S. Appl. No. 12/554,445, filed Sep. 4, 2009.
Final Office Action mailed Nov. 16, 2011 for U.S. Appl. No. 12/560,897, filed Sep. 16, 2009.
Final Office Action mailed Oct. 19, 2011 for U.S. Appl. No. 12/560,893, filed Sep. 16, 2009.
Final Office Action mailed Mar. 24, 2011 for U.S. Appl. No. 11/755,434, filed May 30, 2007.
Final Office Action mailed Dec. 28, 2011 for U.S. Appl. No. 12/639,173, filed Dec. 16, 2009.
Florjancic, et al (2009): Caplus Entry for WO2009067613, Accession No. 2009:649814.
Florjancic, et al (2010): STN International HCAPLUS database, Columbus (OH), Accession No. 2010:478868.
Foster, et al., "Deuterium Isotope Effects in the Metabolism of Drugs and Xenobiotics: Implications for Drug Design," Advances in Drug Research, 1985, vol. 14, pp. 2-36.
Giron, D., "Applications of Thermal Analysis and Coupled Techniques in Pharmaceutical Industry," Journal of Thermal Analysis and Calorimetry, 2002, vol. 68, pp. 335-357.
Giron, D., "Investigations of Polymorphism and Pseudo-Polymorphism in Pharmaceuticals by Combined Thermoanalytical Techniques," The Journal of Thermal Analysis and Calorimetry, 2001, vol. 64, pp. 37-60.
Golech, et al., "Human Brain Endothelium: Coexpression and Function of Vannilloid and Endocannabinoid Receptors," Molecular Brain Research, 2004, vol. 132 (1), pp. 87-92.
Golub, et al., "Molecular Classification of Cancer: Class Discovery and Class Prediction by Gene Expression Monitoring," Science, 1999, vol. 286 (5439), pp. 531-537.
Gouldson, et al., "Mutational Analysis and Molecular Modeling of the Antagonist SR144528 Binding Site on the Human Cannabinoid CB2 Receptor; Figures 4 and 5," European Journal of Pharmacology, 2000, vol. 401 (1), pp. 17-25.
Hargreaves, et al., "A New and Sensitive Method for Measuring Thermal Nociception in Cutaneous Hyperalgesia," Pain, 1988. 32 (1), pp. 77-88.
International Search Report for Application No. PCT/US07/069921, mailed on Nov. 27, 2007, 4 pages.
International Search Report for Application No. PCT/US2009/056179, mailed on Jun. 9, 2010, 4 pages.
International Search Report for Application No. PCT/US2009/057088, mailed on Oct. 5, 2010, 4 pages.
International Search Report for Application No. PCT/US2009/068173, mailed on Feb. 5, 2010, 3 pages.
Kato, et al., "Synthesis of Deuterated Mosapride Citrate," Journal of Labelled Compounds and Radiopharmaceuticals, 1995, vol. 36 (10), pp. 927-932.
Kreutzberg, et al., "Microglia: A Sensor for Pathological Events in the CNS," Trends in Neuroscience, 1996, vol. 19, pp. 312-318.
Kushner, et al., "Pharmacological uses and perspectives of heavy water and deuterated compounds," Canadian Journal of Physiology and Pharmacology, 1999, vol. 77 (2), pp. 79-88.
Lizondo, et al., "Linezolid: Oxazolidinone antibacterial," Drugs of the Future, 1996, vol. 21 (11), pp. 1116-1123.
Maligres, et al., "Stereocontrolled Preparation of a Nonpeptidal (−)-Spirobicyclic NK-1 Receptor Antagonist," Journal of Organic Chemistry, 2002, vol. 67 (4), pp. 1093-1101.
Mallesham, et al., "Highly Efficient CuI-Catalyzed Coupling of Aryl Bromides With Oxazolidinones Using Buchwald's Protocol: A Short Route to Linezolid and Toloxatone," Organic Letters, 2003, vol. 5 (7), pp. 963-965.
Manaka, et al., "2-Acylimino-3H-thiazoline Derivatives: A Novel Template for Platelet GPIIb/IIIa Receptor Antagonists," Bioorganic & Medicinal Chemistry Letters, 2001, vol. 11, pp. 1031-1035.
Molina-Holgado, et al., "Endogenous Interleukin-1 Receptor Antagonist Mediates Anti-Inflammatory and Neuroprotective Actions of Cannabinoids in Neurons and Glia," Journal of Neuroscience, 2003, vol. 23 (16), pp. 6470-6474.
Non-Final Office Action mailed Jun. 1, 2011 for U.S. Appl. No. 12/554,445, filed Sep. 4, 2009.
Non-Final Office Action mailed Jun. 1, 2011 for U.S. Appl. No. 12/560,897, filed Sep. 16, 2009.
Non-Final Office Action mailed Jun. 2, 2009 for U.S. Appl. No. 11/755,434, filed May 30, 2007.
Non-Final Office Action mailed May 17, 2011 for U.S. Appl. No. 12/560,893, filed Sep. 16, 2009.
Non-Final Office Action mailed Aug. 23, 2011 for U.S. Appl. No. 12/639,173, filed Dec. 16, 2009.
Non-Final Office Action mailed Jan. 27, 2011 for US. Appl. No. 12/274,105, filed Nov. 19, 2008.
Non-Final Office Action mailed Jun. 29, 2010 for U.S. Appl. No. 11/755,434, filed May 30, 2007.
Non-Final Office Action mailed Nov. 30, 2010 for U.S. Appl. No. 11/755,434, filed May 30, 2007.
Nunez, et al., "Cannabinoid CB2 Receptors Are Expressed by Perivascular Microglial Cells in the Human Brain: An Immunohistochemical Study," Synapse, 2004, vol. 53, pp. 208-213.
Ohta, et al., "N-Alkyidenearylcarboxamides as a new Potent and Selective CB2 Cannabinoid Receptor Agonist with an Analgesic Action," Bioorganic and Medicinal Chemistry Letters, 2007, vol. 17 (22), pp. 6299-6304.
Opposition filed by "Asociacion de Industrias Farmaceuticas Dominicanas Inc" for the Dominican Patent application Nr P2008-0060, received on Apr. 1, 2009, 8 pages.
Radulescu, et al., "Actes Du Colloque Franco-Roumain De Chimie Appliquee, 3Rd, Bacau, Romania," 2004, pp. 117-120.
Radulescu, et al., "Synthesis and Characteristics of Compact Condensed Heterocyclic System 2-Aminothiazolo[5,4-c]Pyridine," Revista de Chimie, 2004, vol. 55 (11), pp. 889-893.
Radulescu, et al., "The Comparative Study on the Synthesis Methods of a Heterocyclic System 2-Aminothiazolo[4,5-13]Pyricline," Revista de Chimie, 2005, vol. 56 (6), pp. 659-662.
Ralston, S., "Genetic Determinants of Susceptibility to Osteoporosis," Current Opinion in Pharmacology, 2003, vol. 3, pp. 286-290.

(56) References Cited

OTHER PUBLICATIONS

Rautio, et al, "Prodrugs: Design and Clinical Applications," Nature Reviews Drug Discovery, 2008, vol. 7 (3), pp. 255-270.
Rodriquez-Spong, et al., "General Principles of Pharmaceutical Solid Polymorphism: A Supramolecular Perspective," Advanced Drug Delivery Reviews, 2004, vol. 56 (3), pp. 241-274.
Ross, et al., "Antianaphylactic agents. 1. 2-(Acylamino)oxazoles," Journal of Medicinal Chemistry, 1979, vol. 22(4), pp. 412-417.
Shilpi, et al., "The Synthesis and Antimicrobial Screening of Some Novel Aza-Imidoxy Compounds as Potential Chemotherapeutic Agents," Phosphorus Sulfur and Silicon, 2006, vol. 181 (7), pp. 1665-1673.
Smith, D., "Do Prodrugs Deliver?" Current Opinion in Drug Discovery and Development, 2007, vol. 10 (5), 550-559.
Souillac, et al, "Characterization of Delivery Systems, Differential Scanning Calorimetry," Encyclopedia of Controlled Drug Delivery, 1999, pp. 217-218.
Testa, B., "Prodrugs: Bridging Pharmacodynamic/Pharmacokinetic Gaps," Current Opinion in Chemical Biology, 2009, vol. 13 (3), pp. 338-344.
Thomson, J., "Physiological Effects of D20 in Mammals," Annals of the New York Academy of Sciences, 1960, vol. 84, pp. 736-744.
Walter, et al., "Cannabinoids and Neuroinflammation," British Journal of Pharmacology, 2004, vol. 141 (5), pp. 775-785.
Wang, et al., Drug Delivery: Principles and Applications, John Wiley & Sons, Inc., 2005, pp. 136-137.
Watkins, et al., "Glial Activation: A Driving Force for Pathological Pain," Trends in Neuroscience, 2001, vol. 24 (8), pp. 450-455.
Werbel, et al., "1-Alkyl-3-(3-alkyl-5-nitro-4-thiazolin-2-ylidene)ureasa and Related Compounds as Schistosomicides," Journal of Medicinal Chemistry, 1972, vol. 15 (9), pp. 955-963.
Weyer, et al., "Blutzuckersenkende Chinolin-8-Carboxamidoalkyl-Benzol Sulfonamid Derivate," Arzneimittel-Forschung, 1974, vol. 24 (3), pp. 269-275.
Widdowson, et al., "Palladium Catalysed Suzuki Reactions of Fluoroarenes," Chemical Communication (Camb), 2003, vol. 5, pp. 578-579.
Williams, et al., "Renin Inhibitors Containing Conformationally Restricted P1-P1 Dipeptide Mimetics," Journal of Medicinal Chemistry, 1991, vol. 34 (3), pp. 887-900.
Zimmer, et al., "Increased Mortality, Hypoactivity, and Hypoalgesia in Cannabinoid CB1 Receptor Knockout Mice," Proceedings of the National Academy of Science, 1999, vol. 96 (10), pp. 5780-5785.
Alfaro I., et al., "Dihydroaromatic Compounds in the Diels-Alder Reaction—III :In Situ Generation and Diels-Alder Reaction of Cyclohexa-1,3-Dienes," Tetrahedron, 1970, vol. 26, pp. 201-218.
Ansell M.F., et al., "The Synthesis of (+/−)-10a-Homo-11a-Carbathromboxane A1, a Stable Thromboxane A Analogue," Journal of Chemical Society Perkin Trans, 1984, pp. 1061-1068.
Bacon E.R., et al., "Synthesis of 7-Ethyl-4, 7-dihydro-4-oxo-2-(4-pyridinyl)thieno[2,3-b]pyridine-5-carboxylic Acid," Journal of Heterocyclic Chemistry, 1991, vol. 28, pp. 1953-1955.
Bartlett P.A., et al., "Chorismate Mutase Inhibitors: Synthesis and Evaluation of Some Potential Transition-State Analogues," Journal of Organic Chemistry, 1988, vol. 53, pp. 3195-3210.
Bruson H.A., et al., "Action of Sulfuric Acid upon Unsaturated Isothiocyanates: Mercaptothiazolines," Journal of American Chemical Society, 2011, vol. 59 (10), pp. 2011-2013.
CAS Registry No. 1061668-81-2, which entered STN on Oct. 15, 2008.
Castejon P., et al., "A Convenient, Stereodivergent Approach to the Enantioselective Synthesis of N-Boc-Aminoalkyl Epoxides," Tetrahedron Letters, 1995, vol. 36 (17), pp. 3019-3022.
Chauhan M.S., "The Reaction of Some Heterocyclic Thiones with Ethyl Azidoformate," Canadian Journal of Chemistry, 1976, vol. 54 (24), pp. 3879-3883.
Cotarca L., et al., "Bis (trichloromethyl) Carbonate in Organic Synthesis," 1996, vol. 6, pp. 553-576.

Dauben W.G., et al., "Organic Reactions at High Pressure Cycloadditions with Furans," Journal of the American Chemical Society, 1976, vol. 98 (7), pp. 1992-1993.
Dawood K.M., et al., "Synthesis, Anticonvulsant, and Anti-Inflammatory Evaluation of Some New Benzotriazole and Benzofuran-Based Heterocycles," Bioorganic & Medicinal Chemistry, 2006, vol. 14 (11), pp. 3672-3680.
DeWolfe R.H., "Reactions of Aromatic Amines with Aliphatic Ortho Esters. A Convenient Synthesis of Alkyl N-Arylimidic Esters," Journal of Organic Chemistry, 1962, vol. 27, pp. 490-493.
Dorsch J.B., et al., "The Preparation of Benzoylacetic Ester and Some of its Homologs," Journal of the American Chemical Society, 1932, vol. 54, pp. 2960-2964.
Eckert H., et al., "Triphosgene, a Crystalline Phosgene Substitute," Angewandte Chemie International Edition in English, 1987, vol. 26 (9), pp. 894-895.
Ex Parte Quayle Action mailed Oct. 12, 2012 for U.S. Appl. No. 13/160,952, filed Jun. 15, 2011.
Fattori D., et al., "The Demjanov and Tiffeneau-Demjanov One-Carbon Ring Enlargements of 2-Aminomethy1-7-Oxabicyclo[2.2.1]Heptane derivatives. The Stereo- and Regioselective Additions of 8-Oxabicyclo[3.2.1]Oct-6-en-2-One to Soft Electrophiles," Tetrahedron, 1993, vol. 49 (8), pp. 1649-1664.
Final Office Action mailed Feb. 15, 2011 for U.S. Appl. No. 12/120,969, filed on May 15, 2008.
Final Office Action mailed Apr. 19, 2011 for U.S. Appl. No. 12/539,120, filed Aug. 11, 2009.
Goerdeler J., et al., ""Uber Isothiazole, VIII. Synthese von Sulfonylamino-isothiazolen and Sulfonyliminoisothiazolinen aus Sulfonylsenfolen,"" Chemische Berichte, 1969, vol. 102 (7), pp. 2273-2284.
Goodman A.J., et al., "CB2 Selective Sulfamoyl Benzamides; Optimization of the Amide Functionality," Bioorganic & Medicinal Chemistry Letters, 2009, vol. 19 (2), pp. 309-313.
Greene T.W., et al., in: Protective Groups in Organic Synthesis, 3rd Edition, John Wiley and Sons, Inc., 1999, Preface, Table of Contents, Abbreviations.
Hamuro Y., et al., "Solid-Phase Synthesis of Acyclic and Cyclic Amino Acid Derived Urea Peptidomimetics Using Phoxime Resin," The Journal of Combinatorial Chemistry, 1999, vol. 1, pp. 163-172.
Horig H., et al., "From Bench to Clinic and Back: Perspective on the 1st IQPC Translational Research conference," Journal of Translational Medicine, 2004, vol. 2 (44).
Hutchins S.M., et al., "A General Method for the Solid Phase Synthesis of Ureas," Tetrahedron Letters, 1994, vol. 35 (24), pp. 4055-4058.
Hutchins S.M., et al., "A Strategy for Urea Linked Diamine Libraries," Tetrahedron Letters, 1995, vol. 36 (15), pp. 2583-2586.
International Preliminary Report on Patentability and Written Opinion for Application No. PCT/US07/081263, mailed on Apr. 15, 2010, 8 pages.
International Preliminary Report on Patentability and Written Opinion for Application No. PCT/US08/069453, mailed on Jan. 12, 2010, 6 pages.
International Preliminary Report on Patentability and Written Opinion for Application No. PCT/US2005/046480, mailed on Jun. 26, 2007, 8 pages.
International Preliminary Report on Patentability and Written Opinion for Application No. PCT/US2007/0087175, mailed on Jun. 23, 2009, 8 pages.
International Preliminary Report on Patentability and Written Opinion for Application No. PCT/US2007/069921, mailed on Dec. 3, 2008, 10 pages.
International Preliminary Report on Patentability and Written Opinion for Application No. PCT/US2007/070029, mailed on Dec. 3, 2008, 8 pages.
International Preliminary Report on Patentability and Written Opinion for Application No. PCT/US2007/077321, mailed on Mar. 3, 2009, 7 pages.
International Preliminary Report on Patentability and Written Opinion for Application No. PCT/US2008/057460, mailed on Sep. 29, 2009, 11 pages.

(56) References Cited

OTHER PUBLICATIONS

International Preliminary Report on Patentability and Written Opinion for Application No. PCT/US2008/060400, mailed on Oct. 20, 2009, 11 pages.
International Preliminary Report on Patentability and Written Opinion for Application No. PCT/US2008/084216, mailed on May 25, 2010, 5 pages.
International Preliminary Report on Patentability and Written Opinion for Application No. PCT/US2009/053369, mailed on Feb. 15, 2011, 6 pages.
International Preliminary Report on Patentability and Written Opinion for Application No. PCT/US2009/056179, mailed on Mar. 8, 2011, 9 pages.
International Preliminary Report on Patentability and Written Opinion for Application No. PCT/US2009/063318, mailed on May 10, 2011, 5 pages.
International Preliminary Report on Patentability and Written Opinion for Application No. PCT/US2009/068173, mailed on Jun. 21, 2011, 8 pages.
International Preliminary Report on Patentability for Application No. PCT/US2007/077320, mailed on Mar. 3, 2009, 1 page.
International Preliminary Report on Patentability for Application No. PCT/US2009/036715, mailed on Sep. 14, 2010, 1 page.
International Search Report and Written Opinion for Application No. PCT/US2007/077320, mailed on Feb. 7, 2008, 12 pages.
International Search Report and Written Opinion for Application No. PCT/US2009/036715, mailed on Jun. 10, 2009, 9 pages.
International Search Report for Application No. PCT/US07/070029, mailed on Nov. 30, 2007, 3 pages.
International Search Report for Application No. PCT/US07/081263, mailed on Nov. 27, 2008, 3 pages.
International Search Report for Application No. PCT/US08/057460, mailed on Aug. 20, 2008, 3 pages.
International Search Report for Application No. PCT/US08/060400, mailed on Oct. 17, 2008, 3 pages.
International Search Report for Application No. PCT/US08/069453, mailed on Sep. 25, 2008, 2 pages.
International Search Report for Application No. PCT/US08/079182, mailed on Dec. 15, 2008, 2 pages.
International Search Report for Application No. PCT/US2005/0046480, mailed on Apr. 18, 2006, 5 pages.
International Search Report for Application No. PCT/US2007/0077321, mailed on Feb. 1, 2008, 3 pages.
International Search Report for Application No. PCT/US2007/0087175, mailed on Apr. 8, 2008, 4 pages.
International Search Report for Application No. PCT/US2008/084216, mailed on Feb. 19, 2009, 1 page.
International Search Report for Application No. PCT/US2009/053369, mailed on Oct. 22, 2009, 3 pages.
International Search Report for Application No. PCT/US2009/063318, mailed on May 6, 2010, 3 pages.
International Search Report for Application No. PCT/US2010/028794, mailed Jul. 20, 2010, 3 pages.
International Search Report for Application No. PCT/US2010/028796, mailed Jul. 16, 2010, 4 pages.
International Search Report for Application No. PCT/US2011/040501, mailed on Oct. 24, 2011, 2 pages.
Izdebski J., et al., "A New Convenient Method for the Synthesis of Symmetrical and Unsymmetrical N,N'-Disubstituted Ureas," Synthesis, 1989, pp. 423-425.
Jasys V.J., et al., "Preparation of Fluoroadamantane Acids and Amines: Impact of Bridgehead Fluorine Substitution on the Solution- and Solid-State Properties of Functionalized Adamantanes," Journal of the American Chemical Society, 2000, vol. 122, pp. 466-473.
Katritzky A.R., et al., "A General Synthesis of Unsymmetrical Tetrasubstituted Ureas," Journal of Organic Chemistry, 1997, vol. 62 (11), pp. 4155-4158.

Khusnutdinov R.I., et al., "Chlorination of Adamantane and its Derivatives by Carbon Tetrachloride in the Presence of Manganese-, Vanadium-, and molybdenum-Containing Catalysts," Neftekhimiya, 2004, vol. 44 (2), pp. 148-155.
Knolker H.J., et al., "A Novel Method for the Synthesis of Isocyanates Under Mild Conditions," Angewandte Chemie International Edition in English, 1995, vol. 34 (22), pp. 2497-2500.
Knolker H.J., et al., "Synthesis of Symmetrical and Unsymmetrical Ureas by DMAP-Catalyzed Reaction of Alkyl- and Arylamines with Di-tert-butyldicarbonate," Synlett, 1996, pp. 502-504.
Kolasa., "Thiazolylidene Derivatives as Cannabinoid Receptor Ligands and Their Preparation" Accession No. 2008:1184581, Mar. 22, 2011.
Kruijtzer J., et al., "Approaches to the Synthesis of Ureapeptoid Peptidomimetics," Tetrahedron Letters, 1997, vol. 38 (30), pp. 5335-5338.
Lamothe M., et al., "A Simple One-Pot Preparation of N,N'-unsymmetrical ureas from N-Boc Protected Primary Anilines and Amines," Synlett, 1996, vol. 6, pp. 507-508.
Lemoucheux L., et al., "Debenzylation of Tertiary Amines Using Phosgene or Triphosgene: An Efficient and Rapid Procedure for the Preparation of Carbamoyl Chlorides and Unsymmetrical Ureas. Application in Carbon-11 Chemistry," Journal of Organic Chemistry, 2003, vol. 68 (19), pp. 7289-7297.
Leung M.K., et al., "S,S-Dimethyl Dithiocarbonate: A Convenient Reagent for the Synthesis of Symmetrical and Unsymmetrical Ureas," Journal of Organic Chemistry, 1996, vol. 61 (12), pp. 4175-4179.
Linn, et al., Journal of American Chemistry Society, 1963, 2032, vol. 85.
Majer P., et al., "A Safe and Efficient Method for Preparation of N,"-Unsymmetrically Disubstituted Ureas Utilizing Triphosgene," Journal of Organic Chemistry, 1994, vol. 59, pp. 1937-1938.
Masciadri R., et al., "Regioselective Friedel_Crafts Alkylation of Anilines and Amino-Substituted Heteroarenes with Hexafluoroacetone Sesquihydrate," European Journal of Organic Chemistry, 2003, vol. 2003 (21), pp. 4286-4291.
Meyers A.I., et al., "Oxazolines. XX. Synthesis of Achiral and Chiral Thiiranes and Olefins by Reaction of Carbonyl Compounds with 2-(Alkylthio)-2-oxazolines," Journal of Organic Chemistry, 1976, vol. 41 (10), pp. 1735-1742.
Miyaura N., et al., ed., Topics in Current Chemistry: Cross-Coupling Reactions, Springer, 2002, Table of Contents.
Morii T., et al., "A General Strategy to Determine a Target DNA Sequence of a Short Peptide: Application to a [D]-Peptide," Journal American Chemical Society, 2002, vol. 124 (2), pp. 180-181.
Negishi E., et al., eds., Handbook of Organopalladium Chemistry for Organic Synthesis, vol. 1, John Wiley & Sons, 2002, Table of Contents.
Nieuwenhuijzen J.W., et al., "Solid and Solution Phase Combinatorial Synthesis of Ureas," Tetrahedron Letters, 1998, vol. 39, pp. 7811-7814.
Non-Final Office Action mailed Sep. 7, 2010 for U.S. Appl. No. 12/120,969, filed on May 15, 2008.
Non-Final Office Action mailed Mar. 9, 2012 for U.S. Appl. No. 12/732,428, filed Mar. 26, 2010.
Non-Final Office Action mailed Jan. 12, 2010 for U.S. Appl. No. 12/120,969, filed on May 15, 2008.
Ohta H., et al., "Imine Derivatives as new Potent and Selective CB2 Cannabinoid Receptor agonist with an Analgesic Action," Bioorganic and Medicinal Chemistry, 2007, vol. 16 (3), pp. 1111-1124.
Ozaki S., et al., "Recent Advances in Isocyanate Chemistry," Chemical Reviews, 1972, vol. 72 (5), pp. 457-496.
Partch, R., et al., "2-Oxaadamantane-1-N,N,N-trimethylmethanaminium Iodide:1 Synthesis and Potential for Muscarinic Activity," Croatia Chemical Acta, 1985, vol. 58 (4), pp. 661-669.
Rezoni G.E., et al., "Synthesis of 7-Carboxytricyclo[33103,7]nonan-3-ol," Journal of Organic Chemistry, 1983, vol. 48, pp. 5231-5236.
Sabnis R.W., et al., "2-Aminothiophenes by the Gewald Reaction," Journal of Heterocyclic Chemistry, 1999, vol. 36, pp. 333-345.

(56) References Cited

OTHER PUBLICATIONS

Schafer S., et al., "Failure is an Option: Learning from Unsuccessful Proof-of-concept Trials," Drug Discovery Today, 2008, vol. 13 (21-22), pp. 913-916.
Scialdone M.A., et al., "Phosgenated p-nitrophenyl(polystyrene)ketoxime or phoxime resin. A new resin for the solid-phase synthesis of ureas via thermolytic cleavage of oxime-carbamates", Journal of Organic Chemistry, 1998, vol. 63, pp. 4802-4807.
Shultz D.A., et al., "Synthesis of Bis(semiquinone)s and their Electrochemical and Electron Paramagnetic Resonance Spectral Characterization," Journal of Organic Chemistry, 1998, vol. 63(25), pp. 9462-9469.
Supplementary European Search Report for Application No. EP08852528, mailed on Nov. 8, 2010, 2 pages.
Takeda K., et al., "Convenient Methods for Syntheses of Active Carbamates, Ureas and Nitrosoureas Using N,N-disuccinimido Carbonate (DSC)," Tetrahedron Letters, 1983, vol. 24, pp. 4569-4572.
Vippagunta S.R., et al., "Crystalline Solids," Advanced Drug Delivery Reviews, 2001, vol. 48 (1), pp. 3-26.
Williams K., et al., "Central Nervous System Perivascular Cells Are Immunoregulatory Cells that Connect the CNS tith the Peripheral mune System," Journal of Glia, 2001, vol. 36 (2), pp. 156-164.
Wu K.M., et al., "Regulatory Perspectives of Type II Prodrug Development and Time-Dependent Toxicity Management: Nonclinical Pharm/Tox Analysis and the Role of Comparative Toxicology," Toxicology, 2007, vol. 236 (1-2), pp. 1-6.
Yao B.B., et al., "In Vitro Pharmacological Characterization Of Am1241: A Protean Agonist At The Cannabinoid Cb2 Receptor," British Journal of Pharmacology, 2006, vol. 149 (2), pp. 145- 54.
Andreani, et al., "Ring-opened, etc," Collection of Czechoslovak Chemical Communications, 1999, vol. 64, pp. 299-312.
Atwood B.K., et al., "CB2: Therapeutic Target-in-Waiting," Progress in Neuro-Psychopharmacology & Biological Psychiatry, 2012, vol. 38 (1), pp. 16-20.
Bermudez-Silva, et al., "Role of Cannabinoid CB2 Receptors in Glucose Homeostasis in Rats," European Journal of Pharmacology, 2007, vol. 565 (1-3), pp. 207-211.
Campbell V.A., et al., "Alzheimer's Disease; Taking the Edge off with Cannabinoids?," British Journal of Pharmacology, 2007, vol. 152 (5), pp. 655-662.
Caplus Entry for International Application Publication No. WO2008130953, Accessed Aug. 14, 2012, with Structures Relevant to Claim 25 as Filed Aug. 11, 2011.
Caplus Entry for International Application Publication No. WO2008130953, Accessed Aug. 14, 2012, with Structures Relevant to Claim 35 as Filed Aug. 11, 2011.
Chemical Abstracts Accession No. 1030770638, Jun. 26, 2008.
Cross., et al., "Rules for the Nomenclature of Organic Chemistry, Section E: Stereochemistry," International Union of Pure and Applied Chemistry, 1976, vol. 45, pp. 11-30.
Database Registry [Online] Chemical Abstracts Service, Columbus, Ohio, US, Mar. 2, 2008, XP002687516, Database Accession No. 1006022-43-0.
Database Registry [Online] Chemical Abstracts Service, Columbus, Ohio, US, Mar. 2, 2008, XP002687517, Database Accession No. 1005993-02-1.
Database Registry [Online] Chemical Abstracts Service, Columbus, Ohio, US, Mar. 6, 2008, XP002687515, Database Accession No. 1006758-59-3.
Database Registry [Online] Chemical Abstracts Service, Columbus, Ohio, US, Mar. 7, 2008, XP002687514, Database Accession No. 1007004-94-5.
Database Registry [Online] Chemical Abstracts Service, Columbus, Ohio, US, Mar. 10, 2008, XP002687513, Database Accession No. 1007244-89-4.
Database Registry [Online] Chemical Abstracts Service, Columbus, Ohio, US, Feb. 29, 2008, XP002687518, Database Accession No. 1005931-81-6.

Dellemijn P.L., et al., "Randomised Double-Blind Active-Placebo-Controlled Crossover Trial of Intravenous Fentanyl in Neuropathic Pain," Lancet, 1997, vol. 349 (9054), pp. 753-758.
Ebata et al., "Synthesis of Both Enantiomers of 4-Hexanolide and 4-Dodecanolide," Agriculture Biochemical, 1991, vol. 55 (6), pp. 1685-1686.
European Search Report for Application No. EP12187944, mailed on Nov. 20, 2012, 7 pages.
Final Office Action mailed Oct. 3, 2013 for U.S. Appl. No. 12/246,808, filed on Oct. 7, 2008.
Final Office Action mailed Jul. 14, 2011 for U.S. Appl. No. 12/246,808, filed on Oct. 7, 2008.
Final Office Action mailed Apr. 23, 2013 for U.S. Appl. No. 12/967,275, filed on Dec. 14, 2010.
International Preliminary Report on Patentability and Written Opinion for Application No. PCT/US08/079182, mailed on Apr. 13, 2010, 5 pages.
International Preliminary Report on Patentability and Written Opinion for Application No. PCT/US08/080253, mailed on Apr. 20, 2010, 6 pages.
International Preliminary Report on Patentability and Written Opinion for Application No. PCT/US2008/063648, mailed on Nov. 24, 2009, 7 pages.
International Preliminary Report on Patentability and Written Opinion for Application No. PCT/US2010/028790, mailed on Sep. 27, 2008, 5 pages.
International Search Report for Application No. PCT/US08/080253, mailed on Mar. 3, 2009, 3 pages.
International Search Report for Application No. PCT/US2010/028790, mailed Jul. 19, 2010, 3 pages.
Jhaveri M.D., et al., "Cannabinoid CB2 Receptor-Mediated Anti-Nociception in Models of Acute and Chronic Pain," Molecular Neurobiology, 2007, vol. 36 (1), pp. 26-35.
Kherjee S., et al., "Species Comparison and Pharmacological Characterization of Rat and Human Cb2 Cannabinoid Receptors," European Journal of Pharmacology, 2004, vol. 505 (1-3), pp. 1-9.
Kubinyi, "3D QSAR in Drug Design: Ligand Protein Interactions & Molecular Similarity, 800 pages," Springer, 1998, vol. 2-3, pp. 243-244.
Maclennan S.J., et al., "Evidence for Inverse Agonism of SR141716A at Human Recombinant Cannabinoid CB1 and CB2 Receptors," British Journal of Pharmacology, 1998, vol. 124 (4), pp. 619-622.
Malan T.P., et al., "Inhibition of Pain Responses by Activation of CB(2) Cannabinoid Receptors," Chemistry and Physics of Lipids, 2002, vol. 121 (1-2), pp. 191-200.
Mallat A., et al., "Cannabinoid Receptors as New Targets of Antifibrosing Strategies during Chronic Liver Diseases," Expert Opinion on Therapeutic Targets, 2007, vol. 11 (3), pp. 403-409.
Mayo clinic, Alzheimer's disease, [retrieved on Mar. 11, 2013]. Retrieved from the Internet< URL: http://www.mayoclinic.com/health/alzheimers•disease/DS00161/DSECTION=prevention>.
Morissette S.L., et al., "High-throughput Crystallization: Polymorphs, Salts, Co-crystals and Solvates of Pharmaceutical Solids.," Advanced Drug Delivery Reviews, 2004, vol. 56 (3), pp. 275-300.
Mucke L., "Neuroscience: Alzheimer's Disease," Nature, 2009, vol. 461 (7266), pp. 895-897.
Padgett L.W., et al., "Recent Developments in Cannabinoid Ligands," Life Sciences, 2005, vol. 77 (14), pp. 1767-1798.
Schuart J., et al., "2-aminooxazoles and 2-iminooxazolines. 3. Selected Examples of a Homolog Series of 3 Substituted 2-imino-4-methyl-5-phenyloxazolines," Die Pharmazie, 1974, vol. 29 (3), pp. 170-172.
STN International HCAPLUS database Accession number: 2008:1184581, Columbus, Ohio, Lolasa et al, 2008.
Supplementary European Search Report for Application No. EP08837396, mailed on Jan. 16, 2012, 2 pages.
Vasil'eva V.F., et al., "Synthesis and Properties of 2-imino-3-benzyl-5-phenyl-1,3,4-oxadiazoline, "Caplus, 1970.
Viallet, et al., "2-Aminothiazoline, etc," 1980, CA 93:8074.
Wermuth, "The practice of Medicinal chemistry," 2003, Chapters 9-10, 2nd edition, 768 pages.

(56) References Cited

OTHER PUBLICATIONS

Whiteside G.T., et al., "The Role of the Cannabinoid Cb2 Receptor in Pain Transmission and Therapeutic Potential of Small Molecule CB2 Receptor Agonists," Current medicinal chemistry, 2007, vol. 14 (8), pp. 917-936.

Non-Final Rejection mailed Dec. 5, 2013 for U.S. Appl. No. 12/967,282, filed Dec. 14, 2010.
Office Action mailed Nov. 15, 2013 for European Application No. 05855099.7 filed Dec. 21, 2005.

* cited by examiner

US 8,735,434 B2

COMPOUNDS AS CANNABINOID RECEPTOR LIGANDS

This application claims priority to U.S. Ser. No. 60/938,838, filed May 18, 2007, and is incorporated herein by reference, in its entirety.

TECHNICAL FIELD AND BACKGROUND

The present application relates to thiazolylidene containing compounds, compositions comprising such compounds, and methods of treating conditions and disorders using such compounds and compositions.

(−)-Δ$^9$-Tetrahydrocannabinol (Δ$^9$-THC), the major psychoactive constituent of marijuana, exerts a broad range of effects through its interactions with two cannabinoid (CB) receptor subtypes, CB$_1$ and CB$_2$. CB$_1$ receptors are highly expressed in the central nervous system and to a lesser degree in the periphery in a variety of tissues of the cardiovascular and gastrointestinal systems. By contrast, CB$_2$ receptors are most abundantly expressed in multiple lymphoid organs and cells of the immune system, including spleen, thymus, tonsils, bone marrow, pancreas and mast cells.

The psychotropic effects caused by Δ$^9$-THC and other nonselective CB agonists are mediated by CB$_1$ receptors. These CB$_1$ receptor-mediated effects, such as euphoria, sedation, hypothermia, catalepsy, and anxiety, have limited the development and clinical utility of nonselective CB agonists. Recent studies have demonstrated that CB$_2$ modulators are analgesic in pre-clinical models of nociceptive and neuropathic pain without causing the adverse side effects associated with CB$_1$ receptor activation. Therefore, compounds that selectively target CB$_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic). Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel CB$_2$ receptor modulators that have utility in treating pain, including nociceptive and neuropathic pain.

The location of CB$_2$ receptors on the surface of immune cells suggests a role for these receptors in immunomodulation and inflammation. Recent studies have demonstrated that CB$_2$ receptor ligands have immunomodulatory and anti-inflammatory properties. Therefore, compounds that interact with CB$_2$ receptors offer a unique pharmacotherapy for the treatment of immune and inflammatory disorders.

SUMMARY

One embodiment of the present application provides compounds of formula (I)

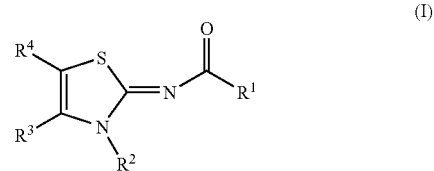

or a pharmaceutically acceptable salt, prodrug, salt of a prodrug, or a combination thereof, wherein R$^1$ is alkyl, alkenyl, alkynyl, haloalkyl, or a monocyclic ring selected from the group consisting of phenyl, cycloalkyl, cycloalkenyl, heteroaryl and heterocycle; wherein each of the monocyclic rings is independently unsubstituted or substituted by 1, 2, 3, 4, or 5 substituents as represented by T, wherein each T is independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$R$^d$, —N(R$^b$)C(O)O(R$^a$), —N(R$^b$)C(O)N(R$^b$)(R$^c$), —(CR$^e$R$^f$)$_r$—NO$_2$, —(CR$^e$R$^f$)$_r$—OR$^a$, —(CR$^e$R$^f$)$_r$—OC(O)R$^a$, —(CR$^e$R$^f$)$_r$—OC(O)N(R$^b$)(R$^c$), —(CR$^e$R$^f$)$_r$—SR$^a$, —(CR$^e$R$^f$)$_r$, —S(O)$_2$R$^d$, —(CR$^e$R$^f$)$_r$—S(O)$_2$N(R$^b$)(R$^c$), —(CR$^e$R$^f$)$_r$—C(O)R$^a$, —(CR$^e$R$^f$)$_r$—C(O)OR$^a$, —(CR$^e$R$^f$)$_r$—C(O)N(R$^b$)(R$^c$), —(CR$^e$R$^f$)$_r$—N(R$^b$)(R$^c$), —(CR$^e$R$^f$)$_r$—N(R$^b$)C(O)R$^a$, —(CR$^e$R$^f$)$_r$—N(R$^e$)S(O)$_2$R$^d$, (CR$^e$R$^f$)$_r$—N(R$^b$)C(O)O(R$^a$), —(CR$^e$R$^f$)$_r$—N(R$^b$)C(O)N(R$^b$)(R$^c$), —(CR$^e$R$^f$)$_r$-G$^1$, —(CR$^e$R$^f$)$_r$—CN, haloalkyl, —O—(CR$^e$R$^f$)$_r$—C(O)N(R$^{b1}$)(R$^{c1}$), —O—(CR$^e$R$^f$)$_r$—C(S)N(R$^{b1}$)(R$^{c1}$), —O—(CR$^e$R$^f$)$_r$—S(O)$_2$N(R$^{b1}$)(R$^{c1}$), —O—(CR$^e$R$^f$)$_s$—N(R$^b$)(R$^c$), —O—(CR$^e$R$^f$)$_s$—N(R$^b$)C(O)R$^a$, —O—(CR$^e$R$^f$)$_s$—N(R$^b$)S(O)$_2$R$^d$, and —O—(CR$^e$R$^f$)$_r$—CN;

two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$R$^d$, —N(R$^b$)C(O)O(R$^a$), —N(R$^b$)C(O)N(R$^b$)(R$^c$), —(CR$^e$R$^f$)$_r$—NO$_2$, —(CR$^e$R$^f$)$_r$—OR$^a$, —(CR$^e$R$^f$)$_r$—OC(O)R$^a$, —(CR$^e$R$^f$)$_r$—OC(O)N(R$^b$)

($R^c$), —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^b)C(O)R^a$, —$(CR^eR^f)_r$—$N(R^b)S(O)_2R^d$, —$(CR^eR^f)_r$—$N(R^b)C(O)O(R^a)$, —$(CR^eR^f)_r$—$N(R^b)C(O)N(R^b)(R^c)$, —$(CR^eR^f)_r$-$G^1$, —$(CR^eR^f)_r$—CN, and haloalkyl;

$R^2$ is alkyl, alkenyl, alkynyl, $G^2$, —$C(O)R^a$, —$S(O)_2$—$R^d$, —$O(G^1)$, —$O$—$(CR^eR^f)_r$-$G^1$, —$(CR^eR^f)_s$—$O$-$G^1$, —$(CR^eR^f)_s$—$O$—$(CR^eR^f)_r$-$G^1$, —$(CR^eR^f)_r$—$C(O)$—$R^a$, —$(CR^eR^f)_r$—$SO_2$—$R^d$, —$(CR^eR^f)_s$—$N(R^b)(R^c)$, —$(CR^eR^f)_r$-$G^2$, —$(CR^eR^f)_r$-$G^3$, —$(CR^eR^f)_s$—$N(R^b)SO_2R^d$, —$(CR^eR^f)_s$—$N(R^b)COR^a$, —$(CR^eR^f)_r$—$N(R^b)CON(R^b)(R^c)$, —$(CR^eR^f)_s$—$N(R^b)SO_2N(R^b)(R^c)$, —$(CR^eR^f)_r$—$SO_2N(R^b)(R^c)$, —$(CR^eR^f)_r$—$C(O)N(R^b)(R^c)$, —$(CR^eR^f)_r$—CN, haloalkyl, or haloalkoxyalkyl;

$R^3$ and $R^4$, together with the atoms to which they are attached, form a 5- to 8-membered monocyclic heterocycle or a spiroheterocycle; wherein said monocyclic heterocycle contains one oxygen atom, zero or one nitrogen atom, and zero or one additional double bond; two non-adjacent atoms of said monocyclic heterocycle can be optionally linked by an alkenylene bridge of 2-4 carbon atoms, or optionally linked by an alkylene bridge of 1-4 carbon atoms, wherein one of the methylene groups of the alkenylene or the alkylene bridge can be optionally replaced by O, S, S(O), $S(O)_2$, N(H), or N(alkyl); said monocyclic heterocycle or spiroheterocycle can be unsubstituted or substituted with 1, 2, 3, 4, or 5 substituents independently selected from the group consisting of oxo, alkyl, halogen, —OH, —O(alkyl), and haloalkyl;

$R^a$, $R^c$ and $R^{c1}$, at each occurrence, are each independently hydrogen, alkyl, haloalkyl, alkoxyalkyl, haloalkoxyalkyl, $G^1$, or —$(CR^eR^f)_r$-$G^1$;

$R^b$ and $R^{b1}$, at each occurrence, are each independently hydrogen, alkyl, haloalkyl, alkoxyalkyl, cycloalkyl, or haloalkoxyalkyl;

$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^d$, at each occurrence, is independently alkyl, haloalkyl, alkoxyalkyl, cyanoalkyl, $G^1$, or —$(CR^eR^f)_r$-$G^1$;

$R^e$ and $R^f$, at each occurrence, are each independently hydrogen, alkyl, halogen, or haloalkyl;

r, at each occurrence, is independently 1, 2, 3, 4, 5, or 6;

s, at each occurrence, is independently 2, 3, 4, 5, or 6;

$G^1$, at each occurrence, is independently aryl, heteroaryl, cycloalkyl, cycloalkenyl, or heterocycle;

$G^2$, at each occurrence, is independently aryl, heteroaryl, cycloalkyl, or cycloalkenyl;

$G^3$ is a monocyclic heterocycle containing 1 or 2 nitrogen atoms and 0 or 1 sulfur atom;

wherein the rings as represented by $G^1$, $G^2$, or $G^3$ are each independently unsubstituted or substituted with 1, 2, 3, 4, or 5 substituents independently selected from the group consisting of alkyl, alkenyl, alkynyl, halogen, =N—CN, =N—$OR''$, —CN, oxo, —$NO_2$, —$OR'''$, —$OC(O)R'''$, —$OC(O)N(R''')_2$, —$SR'''$, —$S(O)_2R''$, —$S(O)_2N(R''')_2$, —$C(O)R'''$, —$C(O)OR'''$, —$C(O)N(R''')_2$, —$N(R''')_2$, —$N(R''')C(O)R'''$, —$N(R''')S(O)_2R''$, —$N(R''')C(O)O(R''')$, —$N(R''')C(O)N(R''')_2$, —$(CR^eR^f)_r$—$NO_2$, —$(CR^eR^f)_r$—$OR'''$, —$(CR^eR^f)_r$—$OC(O)R'''$, —$(CR^eR^f)_r$—$OC(O)N(R''')_2$, —$(CR^eR^f)_r$—$SR'''$, —$(CR^eR^f)_r$—$S(O)_2R''$, —$(CR^eR^f)_r$—$S(O)_2N(R''')_2$, —$(CR^eR^f)_r$—$C(O)R'''$, —$(CR^eR^f)_r$—$C(O)OR'''$, —$(CR^eR^f)_r$—$C(O)N(R''')_2$, —$(CR^eR^f)_r$—$N(R''')_2$, —$(CR^eR^f)_r$—$N(R''')C(O)R'''$, —$(CR^eR^f)_r$—$N(R''')S(O)_2R''$, —$(CR^eR^f)_r$—$N(R''')C(O)O(R''')$, —$(CR^eR^f)_r$—$N(R''')C(O)N(R''')_2$, —$(CR^eR^f)_r$—CN, and haloalkyl;

$R'''$, at each occurrence, is independently hydrogen, alkyl, haloalkyl, alkoxyalkyl, cycloalkyl, or haloalkoxyalkyl; two $R'''$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and $R''$, at each occurrence, is independently alkyl, haloalkyl, cycloalkyl, cycloalkylalkyl, alkoxyalkyl, or cyanoalkyl.

Another embodiment of the invention is directed to pharmaceutical compositions comprising a therapeutically effective amount of a compound of the invention or a pharmaceutically acceptable salt thereof, in combination with a pharmaceutically acceptable carrier.

Yet another embodiment is related to methods of treating pain, (including, but not limited to, nociceptive pain and neuropathic pain) in a mammal in need of such treatment, said method comprises administering to the mammal a therapeutically effective amount of a compound of the invention or a pharmaceutically acceptable salt thereof, alone or in combination with one or more pharmaceutically acceptable carrier.

Still another embodiment provides methods of treating disorders selected from the group consisting of inflammatory disorders, immune disorders, neurological disorders, cancers of the immune system, respiratory disorders, and cardiovascular disorders in a mammal in need of such treatment comprising administering to the mammal a therapeutically effective amount of a compound of the invention or a pharmaceutically acceptable salt thereof, alone or in combination with one or more pharmaceutically acceptable carrier.

A further embodiment provides methods of providing neuroprotection in a mammal in need of such treatment comprising administering to the mammal a therapeutically effective amount of a compound of the invention or a pharmaceutically acceptable salt thereof, alone or in combination with one or more pharmaceutically acceptable carrier.

Further, the present invention provides the use of compounds of the present invention or a pharmaceutically acceptable salt thereof, in the manufacture of a medicament for the treatment of the disease conditions described above, alone or in combination with one or more pharmaceutically acceptable carrier.

These and other objects of the invention are described in the following paragraphs. These objects should not be deemed to narrow the scope of the invention.

DETAILED DESCRIPTION

Compounds of formula (I) are disclosed in this invention,

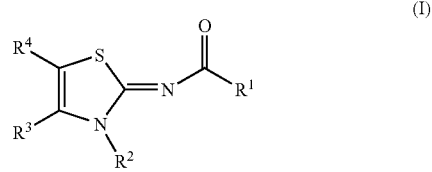

wherein $R^1$, $R^2$, $R^3$, and $R^4$ are as defined above in the Summary of the Invention and below in the Detailed Description.

Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. DEFINITIONS

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. The term "$C_2$-$C_4$ alkenyl" means a straight or branched hydrocarbon chain containing from 2 to 4 carbons and containing at least one carbon-carbon double bond. The term "$C_3$-$C_7$ alkenyl" means a straight or branched hydrocarbon chain containing from 3 to 7 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" denotes a divalent group derived from a straight or branched chain hydrocarbon of 2 to 4 carbon atoms and contains at least one carbon-carbon double bond. Representative examples of alkenylene include, but are not limited to, —CH═CH— and —CH$_2$CH═CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein, means an alkoxy group as defined herein appended to the parent moiety through an alkylene group, as defined herein.

The term "alkyl" as used herein, means a straight or branched, saturated hydrocarbon chain containing from 1 to 10 carbon atoms. The term "lower alkyl" or "$C_1$-$C_6$ alkyl" means a straight or branched chain hydrocarbon containing 1 to 6 carbon atoms. The term "$C_1$-$C_4$ alkyl" means a straight or branched chain hydrocarbon containing 1 to 4 carbon atoms. The term "$C_3$-$C_7$ alkyl" means a straight or branched chain hydrocarbon containing 3 to 7 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" denotes a divalent group derived from a straight or branched chain hydrocarbon of 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—

The term "alkynyl" as used herein, means a straight or branched chain hydrocarbon group containing from 2 to 10 carbon atoms and containing at least one carbon-carbon triple bond. The term "$C_2$-$C_4$ alkynyl" as used herein, means a straight or branched chain hydrocarbon group containing from 2 to 4 carbon atoms and containing at least one carbon-carbon triple bond. The term "$C_3$-$C_7$ alkynyl" as used herein, means a straight or branched chain hydrocarbon group containing from 3 to 7 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "cyanoalkyl" as used herein, means a CN group appended to the parent moiety through an alkylene group, as defined herein.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of between one and four carbon atoms of the bicyclic cycloalkyl ring. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The term "$C_3$-$C_6$ cycloalkyl" means cyclopropyl, cyclobutyl, cyclopentyl, and cyclohexyl. The $C_3$-$C_6$ cycloalkyl, monocyclic, bicyclic, and tricyclic cycloalkyls can be unsubstituted or substituted, and are attached to the parent molecular moiety through any substitutable atom contained within the ring system.

The term "cycloalkylalkyl" as used herein, means a cycloalkyl as defined herein appended to the parent molecular moiety through an alkylene group, as defined herein.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group. The monocyclic or bicyclic cycloalkenyl ring may contain one or two alkylene bridges, each consisting of one, two or three carbon atoms, each linking two non-adjacent carbon atoms of the ring system. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "ethylenedioxy" as used herein, means a —O(CH$_2$)$_2$O— group wherein the oxygen atoms of the ethylenedioxy group are attached to phenyl or naphthyl through two adjacent carbon atoms of the phenyl or the naphthyl, forming a six membered ring.

The term "halo" or "halogen" as used herein, means Cl, Br, I, or F.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, trifluoromethyl, difluoromethyl, pentafluoroethyl, and 2-chloro-3-fluoropentyl.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- or eight-membered ring contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non adjacent atoms of the ring are linked by an alkylene bridge containing one, two, three, or four carbon atoms. Representative examples of bicyclic heterocycles include, but are not limited to, benzopyranyl, benzothiopyranyl, 2,3-dihydrobenzofuranyl, 2,3-dihydrobenzothienyl, 7-oxabicyclo[2.2.1]heptane, and 2,3-dihydro-1H-indolyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non adjacent atoms of the bicyclic ring are linked by an alkylene bridge consisting of one, two, three, or four carbon atoms. Examples of tricyclic heterocycles include, but not limited to, octahydro-2,5-epoxypentalene, hexahydro-2H-2, 5-methanocyclopenta[b]furan, hexahydro-1H-1,4-methanocyclopenta[c]furan, aza-admantane such as 1-azatricyclo[3.3.1.1$^{3,7}$]decane, and oxa-adamantane such as 2-oxatricyclo[3.3.1.1$^{3,7}$]decane. The monocyclic, bicyclic, and tricyclic heterocycles are connected to the parent molecular moiety through any carbon atom or any nitrogen atom contained within the rings, and can be unsubstituted or substituted.

The term "haloalkoxy" as used herein, means an alkoxy group as defined herein in which one, two, three, four, five or six hydrogen atoms are replaced by halogen. Representative examples of haloalkyl include, but are not limited to, trifluoromethoxy and 2,2,2-trifluoroethoxy.

The term "haloalkoxyalkyl" as used herein, means an haloalkoxy group as defined herein appended to the parent moiety through an alkylene group.

The term "heteroaryl" as used herein, means a monocyclic heteroaryl or a bicyclic heteroaryl. The monocyclic heteroaryl is a five- or six-membered ring. The five-membered ring contains two double bonds. The five membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroatom" as used herein, means a nitrogen, oxygen, or sulfur atom.

The term "methylenedioxy" as used herein, means a —OCH$_2$O— group wherein the oxygen atoms of the methylenedioxy are attached to the phenyl or naphthyl through two adjacent carbon atoms of the phenyl or the naphthyl, forming a five-membered ring.

The term "oxo" as used herein, means a =O group.

The term "spiroheterocycle", as used herein, means a 5-, 6-, 7-, or 8-membered monocyclic heterocycle ring containing one oxygen atom, zero or one nitrogen atom, and zero or one double bond, wherein two of the substituents on the same carbon atom form a 4-, 5-, or 6-membered monocyclic cycloalkyl, wherein the cycloalkyl is optionally substituted with 1, 2, 3, 4, or 5 alkyl groups. One example of a spiroheterocycle is 5-oxaspiro[3.4]octane.

b. COMPOUNDS

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

As described generally above for compounds of formula (I), $R^1$ is alkyl, alkenyl, alkynyl, haloalkyl, or a monocyclic group selected from the group consisting of phenyl, cycloalkyl, cycloalkenyl, heteroaryl, and heterocycle, wherein each of these rings is independently unsubstituted or substituted as described in the Summary.

In certain embodiments, $R^1$ is alkyl, alkenyl, alkynyl, or haloalkyl.

In certain embodiments, $R^1$ is a monocyclic ring, substituted or unsubstituted, selected from the group consisting of phenyl, cycloalkyl, cycloalkenyl, heteroaryl and heterocycle. Preferred compounds include those in which $R^1$ is unsubstituted or substituted phenyl. Where the phenyl group is substituted, it is preferred that it is substituted with 1, 2, or 3 substituents as represented by T, more preferably, substituted by two substituents.

Examples of the optional substituents (T) on the monocyclic ring as represented by $R^1$ include, but are not limited to, alkyl, alkenyl, alkynyl, halogen, —CN, oxo, -$G^1$, —$NO_2$, —$OR^a$, —OC(O)$R^a$, —OC(O)N($R^b$)($R^c$), —$SR^a$, —S(O)$_2R^d$, —S(O)$_2$N($R^b$)($R^c$), —C(O)$R^a$, —C(O)O$R^a$, —C(O)N($R^b$)($R^c$), —N($R^b$)($R^c$), —N($R^b$)C(O)$R^a$, —N($R^b$)S(O)$_2R^d$, —N($R^b$)C(O)O($R^a$), —N($R^b$)C(O)N($R^b$)($R^c$), —(CR$^e$R$^f$)$_r$—$NO_2$, —(CR$^e$R$^f$)$_r$—OC(O)$R^a$, —(CR$^e$R$^f$)$_r$—OC(O)N($R^b$)($R^c$), —(CR$^e$R$^f$)$_r$—$SR^a$, —(CR$^e$R$^f$)$_r$—S(O)$_2R^d$, —(CR$^e$R$^f$)$_r$—S(O)$_2$N($R^b$)($R^c$), —(CR$^e$R$^f$)$_r$—C(O)$R^a$, —(CR$^e$R$^f$)$_r$—C(O)O$R^a$, —(CR$^e$R$^f$)$_r$—C(O)N($R^b$)($R^c$), —(CR$^e$R$^f$)$_r$—N($R^b$)($R^c$), —(CR$^e$R$^f$)$_r$—N($R^b$)C(O)$R^a$, —(CR$^e$R$^f$)$_r$—N($R^b$)S(O)$_2R^d$, —(CR$^e$R$^f$)$_r$—N($R^b$)C(O)O($R^a$), —(CR$^e$R$^f$)$_r$—N($R^b$)C(O)N($R^b$)($R^c$), —(CR$^e$R$^f$)$_r$-$G^1$, —(CR$^e$R$^f$)$_r$—CN, haloalkyl, —O—(CR$^e$R$^f$)$_r$—C(O)N($R^{b1}$)($R^{c1}$), —O—(CR$^e$R$^f$)$_r$—C(S)N($R^{b1}$)($R^{c1}$), —O—(CR$^e$R$^f$)$_r$—S(O)$_2$N($R^{b1}$)($R^{c1}$), —O—(CR$^e$R$^f$)$_s$—N($R^b$)($R^c$), —O—(CR$^e$R$^f$)$_s$—N($R^b$)C(O)$R^a$, —O—(CR$^e$R$^f$)$_s$—N($R^b$)S(O)$_2R^d$, and —O—(CR$^e$R$^f$)$_r$—CN; wherein $R^a$, $R^b$, $R^c$, $R^d$, $R^e$, $R^f$, r, s, $R^{b1}$, $R^{c1}$, and $G^1$ are as described in the Summary and in embodiments herein. Certain embodiments include compounds wherein T is —C(O)$R^a$, —C(O)O$R^a$, —C(O)N($R^b$)($R^c$), alkyl, alkenyl, alkynyl, halogen, —CN, -$G^1$, —$OR^a$, —N($R^b$)($R^c$), —N($R^b$)C(O)$R^a$, —N($R^b$)S(O)$_2R^d$, —N($R^b$)C(O)N($R^b$)($R^c$), —O—(CR$^e$R$^f$)$_r$—C(O)N($R^{b1}$)($R^{c1}$), —O—(CR$^e$R$^f$)$_r$—C(S)N($R^{b1}$)($R^{c1}$), —O—(CR$^e$R$^f$)$_r$—S(O)$_2$N($R^{b1}$)($R^{c1}$), —O—(CR$^e$R$^f$)$_s$—N($R^b$)($R^c$), —O—(CR$^e$R$^f$)$_s$—N($R^b$)C(O)$R^a$, —O—(CR$^e$R$^f$)$_s$—N($R^b$)S(O)$_2R^d$, —O—(CR$^e$R$^f$)$_r$—CN, or haloalkyl; wherein $R^a$, $R^b$, $R^c$, $R^d$, $R^e$, $R^f$, r, s, $R^{b1}$, and $R^{c1}$ are as described in the Summary and in embodiments herein.

In other embodiments, T is $C_{1-4}$ alkyl, $C_{2-4}$ alkenyl, $C_{2-4}$ alkynyl, halogen, —CN, —$OR^a$, —O—(CR$^e$R$^f$)$_r$—C(O)N($R^{b1}$)($R^{c1}$), —O(CR$^e$R$^f$)$_r$—S(O)$_2$N($R^{b1}$)($R^{c1}$), —O—(CR$^e$R$^f$)$_s$—N($R^b$)($R^c$), —O—(CR$^e$R$^f$)$_r$—CN, or $C_{1-4}$ haloalkyl; wherein $R^a$, $R^b$, $R^c$, $R^e$, $R^f$, r, s, $R^{b1}$, and $R^{c1}$ are as described in the Summary and in embodiments herein.

In still other embodiments, T is $C_1$-$C_4$ alkyl, $C_2$-$C_4$ alkenyl, $C_2$-$C_4$ alkynyl, halogen, —CN, —$OR^a$, —O—(CH$_2$)$_r$—C(O)N($R^{b1}$)($R^{c1}$), —O—(CH$_2$)$_s$—N($R^b$)($R^c$), —O—(CH$_2$)$_r$—CN, or $C_{1-4}$ haloalkyl; wherein $R^a$, $R^b$, $R^c$, r, s, $R^{b1}$, and $R^{c1}$ are as described in the Summary and in embodiments herein. In yet other embodiments, T is —$OR^a$; halogen, —CN, or trifluoromethyl; wherein $R^a$ is methyl, ethyl, isopropyl, n-propyl, trifluoromethyl, 2,2,2-trifluoroethyl, or 2-fluoroethyl.

In certain embodiments, $R^a$ and $R^c$ are each independently hydrogen, $C_1$-$C_4$ alkyl, $C_1$-$C_4$ haloalkyl, alkoxyalkyl, haloalkoxyalkyl, $G^1$, or —(CR$^e$R$^f$)$_r$-$G^1$. In other embodiments, $R^a$ and $R^c$ are each independently hydrogen, $C_1$-$C_4$ alkyl, $C_1$-$C_4$ haloalkyl, alkoxyalkyl, haloalkoxyalkyl, $G^1$, or —(CH$_2$)$_r$-$G^1$. In yet other embodiments, $R^a$ is methyl, ethyl, isopropyl, n-propyl, trifluoromethyl, 2,2,2-trifluoroethyl, or 2-fluoroethyl. $G^1$, $R^e$, $R^f$, and r are as described generally in the Summary and in the embodiments herein.

$R^b$ has values as described generally in the Summary. In certain embodiments, $R^b$ is hydrogen, $C_1$-$C_4$ alkyl, $C_3$-$C_6$ cycloalkyl, $C_1$-$C_4$ haloalkyl, or methoxyethyl. In other embodiments, $R^b$ is hydrogen, $C_1$-$C_4$ alkyl, $C_3$-$C_6$ cycloalkyl, or methoxyethyl.

$R^{b1}$ and $R^{c1}$ have values as described generally in the Summary. In certain embodiments, $R^{b1}$ is hydrogen, $C_1$-$C_4$ alkyl, $C_3$-$C_6$ cycloalkyl, $C_1$-$C_4$ haloalkyl, or methoxyethyl; $R^{c1}$ is hydrogen, $C_1$-$C_4$ alkyl, $C_3$-$C_6$ cycloalkyl, or $C_1$-$C_4$ haloalkyl; $R^{b1}$ and $R^{c1}$, together with the nitrogen atom to which they are both attached optionally form a 4-7 membered monocyclic heterocycle as described in the Summary. In other embodiments, $R^{b1}$ is hydrogen, $C_1$-$C_4$ alkyl, $C_3$-$C_6$ cycloalkyl, or methoxyethyl; and $R^{c1}$ is hydrogen, $C_1$-$C_4$ alkyl or $C_3$-$C_6$ cycloalkyl.

$R^d$ has values as described generally in the Summary. In certain embodiments, $R^d$, at each occurrence, is independently $C_1$-$C_4$ alkyl, $C_1$-$C_4$ haloalkyl, alkoxyalkyl, cyanoalkyl, $G^1$, or —(CR$^e$R$^f$)$_r$-$G^1$. $R^e$ and $R^f$ are each independently hydrogen or methyl. In other embodiments, $R^d$, at each occurrence, is independently $C_1$-$C_4$ alkyl, $G^1$, or —(CR$^e$R$^f$)$_r$-$G^1$. $G^1$, r, $R^e$, and $R^f$ are as described generally in the Summary and in embodiments herein.

$R^e$ and $R^f$ have values as described generally in the Summary. In certain embodiments, $R^e$ and $R^f$ are each independently hydrogen or methyl.

In certain embodiments, r is 1, 2, 3, or 4 and s is 2, 3, or 4.

$R^2$ has values as described generally in the Summary. Examples of $R^2$ include, but are not limited to alkyl, alkenyl, alkynyl, —(CR$^e$R$^f$)$_s$—O-$G^1$, —(CR$^e$R$^f$)$_s$—O—(CR$^e$R$^f$)$_r$-$G^1$, —(CR$^e$R$^f$)$_r$—C(O)—$R^a$, —(CR$^e$R$^f$)$_r$—SO$_2$—$R^d$, —(CR$^e$R$^f$)$_s$—N($R^b$)($R^c$), —(CR$^e$R$^f$)$_r$-$G^2$, —(CR$^e$R$^f$)$_r$-$G^3$, —(CR$^e$R$^f$)$_s$—N($R^b$)SO$_2R^d$, —(CR$^e$R$^f$)$_s$—N($R^b$)COR$^a$, —(CR$^e$R$^f$)$_s$—N($R^b$)CON($R^b$)($R^c$), —(CR$^e$R$^f$)$_s$—N($R^b$)SO$_2$N($R^b$)($R^c$), —(CR$^e$R$^f$)$_r$—SO$_2$N($R^b$)($R^c$), —(CR$^e$R$^f$)$_r$—C(O)N($R^b$)($R^c$), —(CR$^e$R$^f$)$_r$—CN, haloalkyl, and haloalkoxyalkyl; wherein $R^e$, $R^f$, $G^1$, $G^2$, $G^3$, s, $R^a$, $R^b$, $R^c$, $R^d$, and r are as described in the Summary and in embodiments herein. Particularly, examples of $R^2$ include, but are not limited to, $C_3$-$C_7$ alkyl, $C_3$-$C_7$ alkenyl, $C_3$-$C_7$ alkynyl, —(CR$^e$R$^f$)$_s$—O-$G^1$, —(CR$^e$R$^f$)$_s$—O—(CR$^e$R$^f$)$_r$-$G^1$, —(CR$^e$R$^f$)$_r$—C(O)—$R^a$, —(CR$^e$R$^f$)$_s$—N($R^b$)($R^c$), —(CR$^e$R$^f$)$_r$-$G^2$, —(CR$^e$R$^f$)$_r$-$G^3$, —(CR$^e$R$^f$)$_s$—N($R^b$)SO$_2R^d$, —(CR$^e$R$^f$)$_r$—SO$_2$N($R^b$)($R^c$), —(CR$^e$R$^f$)$_r$—CN, and $C_3$-$C_7$ haloalkyl. Even more particularly, examples of $R^2$ include, but are not limited to, $C_3$-$C_7$ alkyl, $C_3$-$C_7$ alkenyl, $C_3$-$C_7$ alkynyl, —(CH$_2$)$_s$—O-$G^1$, —(CH$_2$)$_s$—O—(CH$_2$)$_r$-$G^1$, —(CH$_2$)$_r$-$G^2$, —(CH$_2$)$_r$-$G^3$, —(CH$_2$)$_s$—N($R^b$)SO$_2R^d$, —(CH$_2$)$_r$—SO$_2$N($R^b$)($R^c$), —(CH$_2$)$_r$—CN, and $C_3$-$C_7$ haloalkyl. In certain embodiments, $R^2$ is n-butyl, isobutyl, n-pentyl, —(CH$_2$)-$G^2$, —(CH$_2$)$_2$—CN, —(CH$_2$)$_3$—CN, or —(CH$_2$)$_4$—CN. In certain embodiments, $R^2$ is $C_3$-$C_7$ alkyl or —(CH$_2$)-$G^2$. In other embodiments, $R^2$ is $C_3$-$C_7$ alkyl or —(CH$_2$)-$G^2$ wherein $G^2$ is cycloalkyl (e.g. $C_3$-$C_6$ cycloalkyl), unsubstituted or substituted as described in the Summary. In yet other embodiments, $R^2$ is —(CH$_2$)-$G^2$ wherein $G^2$ is aryl (e.g. phenyl), unsubstituted or substituted as described in the Summary. In yet other embodiments, $R^2$ is —(CR$^e$R$^f$)$_r$—CN wherein $R^e$ and $R^f$ are each independently hydrogen or methyl, and r is 2, 3, or 4.

G¹ is as described in the Summary. In certain embodiments, G¹ is heteroaryl, heterocycle, or cycloalkyl, unsubstituted or substituted. In other embodiments, G¹ is monocyclic heteroaryl, monocyclic heterocycle, or monocyclic cycloalkyl (e.g. $C_3$-$C_6$ cycloalkyl); each of which is optionally substituted as described generally in the Summary and in the embodiments herein.

G² has values as described generally in the Summary. In certain embodiments, G² is optionally substituted aryl (e.g. phenyl). In other embodiments, G² is monocyclic heteroaryl or monocyclic cycloalkyl (e.g. $C_3$-$C_6$ cycloalkyl), each of which is optionally substituted. In yet other embodiments, G² is cyclopropyl, cyclobutyl, or cyclopentyl, each of which is independently unsubstituted or substituted.

Optional substituents of G¹, G², and G³ are as described in the Summary. Examples include, but are not limited to, alkyl, alkenyl, alkynyl, halogen, =N—CN, =N—OR″, —CN, oxo, —NO₂, —OR‴, —OC(O)R‴, —OC(O)N(R‴)₂, —SR‴, —S(O)₂R″, —S(O)₂N(R‴)₂, —C(O)R‴, —C(O)OR‴, —C(O)N(R‴)₂, —N(R‴)₂, —N(R‴)C(O)R‴, —N(R‴)S(O)₂R″, —N(R‴)C(O)O(R‴), —N(R‴)C(O)N(R‴)₂, haloalkyl, and —(CR^eR^f)_r—O(haloalkyl) wherein R‴, R″, R^e, R^f, and r are as described in the Summary and in embodiments herein. In certain embodiments, the optional substituents are each independently selected from the group consisting of $C_1$-$C_4$ alkyl, $C_2$-$C_4$ alkenyl, $C_2$-$C_4$ alkynyl, halogen, =N—CN, =N—OR″, —CN, oxo, —NO₂, —OR‴, —OC(O)R‴, —OC(O)N(R‴)₂, —SR‴, —S(O)₂R″, —S(O)₂N(R‴)₂, —C(O)R‴, —C(O)OR‴, —C(O)N(R‴)₂, —N(R‴)₂, —N(R‴)C(O)R‴, —N(R‴)S(O)₂R″, —N(R‴)C(O)O(R‴), —N(R‴)C(O)N(R‴)₂, and —(CR^eR^f)_r—O(haloalkyl), wherein R‴, R″, R^e, R^f, and r are as described in the Summary and in embodiments herein. In other embodiments, the optional substituents are each independently selected from the group consisting of $C_1$-$C_4$ alkyl, $C_2$-$C_4$ alkenyl, $C_2$-$C_4$ alkynyl, halogen, —CN, oxo, —OR‴, —S(O)₂R″, —S(O)₂N(R‴)₂, —C(O)R‴, —C(O)N(R‴)₂, —N(R‴)₂, —N(R‴)C(O)R‴, —N(R‴)S(O)₂R″, —N(R‴)C(O)N(R‴)₂, and —(CR^eR^f)_r—O(haloalkyl); wherein R‴, R″, R^e, R^f, and r are as described in the Summary and in embodiments herein.

R‴ and R″ have values as described generally in the Summary. In certain embodiments, R‴ is independently $C_1$-$C_4$ alkyl, $C_1$-$C_4$ haloalkyl, alkoxyalkyl, $C_3$-$C_6$ cycloalkyl, or haloalkoxyalkyl; two R‴ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo. R″, at each occurrence, is independently $C_1$-$C_4$ alkyl, $C_1$-$C_4$ haloalkyl, $C_3$-$C_6$ cycloalkyl, cycloalkylalkyl, alkoxyalkyl, or cyanoalkyl.

R³ and R⁴ have values as described generally in the Summary. In certain embodiments, R³ and R⁴, together with the atoms to which they are attached, form a 5- to 8-membered spiroheterocycle, unsubstituted or substituted as described in the Summary.

In other embodiments, R³ and R⁴, together with the atoms to which they are attached, form a 5- to 8-membered monocyclic heterocycle.

In yet other embodiments, the monocyclic heterocycle is a 5- or 6-membered heterocycle. In still other embodiments, the 5- or 6-membered heterocycle contains one oxygen atom, zero nitrogen atom, zero additional double bond, no alkenylene or alkylene bridge, and is unsubstituted or substituted as described generally in the Summary.

In yet other embodiments, the monocyclic heterocycle is a 6-membered heterocycle containing one oxygen atom, zero nitrogen atom, zero additional double bond, an alkenylene or an alkylene bridge of two carbon atoms, and is unsubstituted or substituted as described generally in the Summary.

Optional substituents on the rings formed by R³, R⁴, and the carbon atoms to which they are attached include, but are not limited to, alkyl (e.g. $C_1$-$C_4$ alkyl), oxo, and hydroxy.

Examples of compounds of formula (I) wherein R³, R⁴, and the carbon atoms to which they are attached form a ring as described in the preceding paragraphs include those of formula (II) and (III)

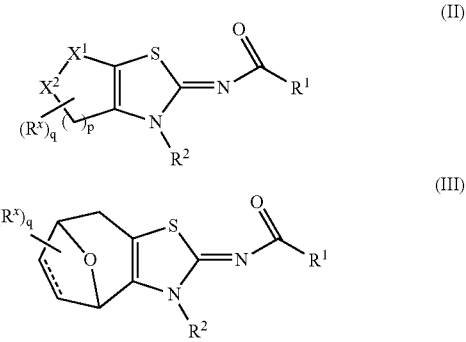

wherein
  X¹ is CH₂, X² is O, and p is 1 or 2; or
  X¹ is CH₂CH₂, X² is O, and p is 1; or
  X¹ is O, X² is CH₂, and p is 2;
  q is 0, 1, 2, 3, or 4;
  ═══ is a single bond or a double bond; and
  R^x is an optional substituent appended to any substitutable carbon within the ring and is selected from the group consisting of oxo, alkyl (e.g. $C_1$-$C_4$ alkyl), halogen, —OH, —O(alkyl), and haloalkyl; and R¹ and R² have values as described generally in the Summary and in embodiments above.

It is appreciated that the present invention contemplates compounds of formula (I) with combinations of the above embodiments, including particular, more particular and preferred embodiments.

Accordingly, one aspect of the invention provides compounds of formula (I), (II), or (III) wherein R¹ is an optionally substituted phenyl, wherein the substituents and R² have values as described generally in the Summary and in embodiments herein above.

For example, present invention provides compounds of formula (IV) or (V)

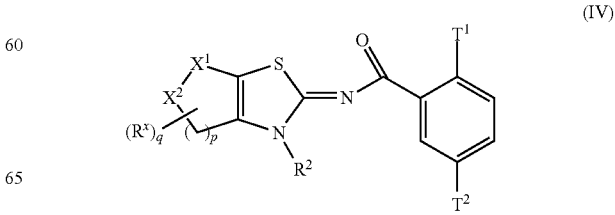

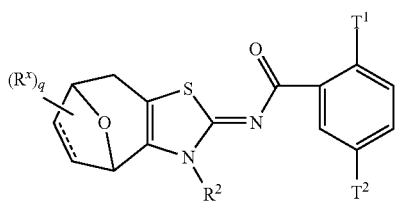

(V)

wherein
$X^1$ is $CH_2$, $X^2$ is O, and p is 1 or 2; or
$X^1$ is $CH_2CH_2$, $X^2$ is O, and p is 1; or
$X^1$ is O, $X^2$ is $CH_2$, and p is 2;
q is 0, 1, 2, 3, or 4;
==== is a single bond or a double bond;
$R^x$ is an optional substituent appended to any substitutable carbon atom in the ring, and is selected from the group consisting of oxo, alkyl, halogen, —OH, —O(alkyl), and haloalkyl;
$T^1$ is $C_1$-$C_4$ alkyl, $C_2$-$C_4$ alkenyl, $C_2$-$C_4$ alkynyl, halogen, —CN, —$OR^a$, —O—$(CR^eR^f)_r$—C(O)N($R^{b1}$)($R^{c1}$), —O—$(CR^eR^f)_r$—S(O)$_2$N($R^{b1}$)($R^{c1}$), —O—$(CR^eR^f)_s$—N($R^b$)($R^c$), —O—$(CR^eR^f)_r$—CN, or $C_{1-4}$ haloalkyl;
$T^2$ is $C_1$-$C_4$ alkyl, $C_2$-$C_4$ alkenyl, $C_2$-$C_4$ alkynyl, halogen, —CN, or $C_1$-$C_4$ haloalkyl;
$R^2$ is $C_3$-$C_7$ alkyl, $C_3$-$C_7$ alkenyl, $C_3$-$C_7$ alkynyl, —$(CR^eR^f)_s$—O-$G^1$, —$(CR^eR^f)_s$—O—$(CR^eR^f)_r$-$G^1$, —$(CR^eR^f)_r$—C(O)—$R^a$, —$(CR^eR^f)_s$—N($R^b$)($R^c$), —$(CR^eR^f)_r$-$G^2$, —$(CR^eR^f)_r$-$G^3$, —$(CR^eR^f)_s$—N($R^b$)SO$_2$$R^d$, —$(CR^eR^f)_r$—SO$_2$N($R^b$)($R^c$), —$(CR^eR^f)_r$—CN, or $C_3$-$C_7$ haloalkyl;
$R^a$ and $R^c$ are each independently hydrogen, $C_1$-$C_4$ alkyl, $C_1$-$C_4$ haloalkyl, alkoxyalkyl, haloalkoxyalkyl, $G^1$, or —$(CR^eR^f)_r$-$G^1$;
$R^b$ is hydrogen, $C_1$-$C_4$ alkyl, $C_3$-$C_6$ cycloalkyl, $C_1$-$C_4$ haloalkyl, or methoxyethyl;
$R^{b1}$ is hydrogen, $C_1$-$C_4$ alkyl, $C_3$-$C_6$ cycloalkyl, $C_1$-$C_4$ haloalkyl, or methoxyethyl;
$R^{c1}$ is hydrogen, $C_1$-$C_4$ alkyl, $C_3$-$C_6$ cycloalkyl, or $C_1$-$C_4$ haloalkyl;
$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;
$R^d$, at each occurrence, is independently $C_1$-$C_4$ alkyl, $C_1$-$C_4$ haloalkyl, alkoxyalkyl, cyanoalkyl, $G^1$, or —$(CR^eR^f)_r$-$G^1$;
$R^e$ and $R^f$ are each independently hydrogen or methyl;
$G^1$ is monocyclic heteroaryl, monocyclic heterocycle, or monocyclic cycloalkyl;
$G^2$ is monocyclic heteroaryl or monocyclic cycloalkyl;
$G^3$ is a monocyclic heterocycle containing 1 or 2 nitrogen atoms and 0 or 1 sulfur atom;
wherein the rings as represented by $G^1$, $G^2$, or $G^3$ are each independently unsubstituted or substituted with 1, 2, 3, 4, or 5 substituents independently selected from the group consisting of $C_{1-4}$ alkyl, $C_2$-$C_4$ alkenyl, $C_2$-$C_4$ alkynyl, halogen, =N—CN, =N—$OR^n$, —CN, oxo, —NO$_2$, —$OR^m$, —OC(O)$R^m$, —OC(O)N($R^m$)$_2$, —$SR^m$, —S(O)$_2$$R^n$, —S(O)$_2$N($R^m$)$_2$, —C(O)$R^m$, —C(O)O$R^m$, —C(O)N($R^m$)$_2$, —N($R^m$)$_2$, —N($R^m$)C(O)$R^m$, —N($R^m$)S(O)$_2$$R^n$, —N($R^m$)C(O)O($R^m$), —N($R^m$)C(O)N($R^m$)$_2$, and —$(CR^eR^f)_r$—O(haloalkyl);

$R^m$, at each occurrence, is independently hydrogen, $C_1$-$C_4$ alkyl, $C_1$-$C_4$ haloalkyl, alkoxyalkyl, $C_3$-$C_6$ cycloalkyl, or haloalkoxyalkyl; two $R^m$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;
$R^n$, at each occurrence, is independently $C_1$-$C_4$ alkyl, $C_1$-$C_4$ haloalkyl, $C_3$-$C_6$ cycloalkyl, cycloalkylalkyl, alkoxyalkyl, or cyanoalkyl;
r is 1, 2, 3, or 4; and
s is 2, 3, or 4.
Other compounds included are those having formula (IV) or (V) wherein
$X^1$ is $CH_2$, $X^2$ is O, and p is 1 or 2; or
$X^1$ is $CH_2CH_2$, $X^2$ is O, and p is 1; or
$X^1$ is O, $X^2$ is $CH_2$, and p is 2;
q is 0, 1, 2, 3, or 4;
==== is a single bond or a double bond;
$R^x$ is an optional substituent appended to any substitutable carbon atom in the ring, and is selected from the group consisting of oxo, alkyl, halogen, —OH, —O(alkyl), and haloalkyl;
$T^1$ is $C_1$-$C_4$ alkyl, $C_2$-$C_4$ alkenyl, $C_2$-$C_4$ alkynyl, halogen, —CN, —$OR^a$, —O—$(CH_2)_r$—C(O)N($R^{b1}$)($R^{c1}$), —O—$(CH_2)_s$—N($R^b$)($R^c$), —O—$(CH_2)_r$—CN, or $C_1$-$C_4$ haloalkyl;
$T^2$ is $C_1$-$C_4$ alkyl, $C_2$-$C_4$ alkenyl, $C_2$-$C_4$ alkynyl, halogen, —CN, or $C_1$-$C_4$ haloalkyl;
$R^2$ is $C_3$-$C_7$ alkyl, $C_3$-$C_7$ alkenyl, $C_3$-$C_7$ alkynyl, —$(CH_2)_s$—O-$G^1$, —$(CH_2)_s$—O—$(CH_2)_r$-$G^1$, —$(CH_2)_r$-$G^2$, —$(CH_2)_r$- $G^3$, —$(CH_2)_s$—N($R^b$)SO$_2$$R^d$, —$(CH_2)_r$—SO$_2$N($R^b$)($R^c$), —$(CH_2)_r$—CN, or $C_3$-$C_7$ haloalkyl;
$R^a$ and $R^c$ are each independently hydrogen, $C_1$-$C_4$ alkyl, $C_1$-$C_4$ haloalkyl, alkoxyalkyl, haloalkoxyalkyl, $G^1$, or —$(CH_2)_r$-$G^1$;
$R^b$ is hydrogen, $C_1$-$C_4$ alkyl, $C_3$-$C_6$ cycloalkyl, or methoxyethyl;
$R^{b1}$ is hydrogen, $C_1$-$C_4$ alkyl, $C_3$-$C_6$ cycloalkyl, or methoxyethyl;
$R^{c1}$ is hydrogen, $C_1$-$C_4$ alkyl or $C_3$-$C_6$ cycloalkyl;
$R^d$, at each occurrence, is independently $C_1$-$C_4$ alkyl, $G^1$, or —$(CR^eR^f)_r$-$G^1$;
$R^e$ and $R^f$ are each independently hydrogen or methyl;
$G^1$ is monocyclic heteroaryl, monocyclic heterocycle, or $C_3$-$C_6$ cycloalkyl;
$G^2$ is monocyclic heteroaryl or $C_3$-$C_6$ cycloalkyl;
wherein the rings as represented by $G^1$, $G^2$, or $G^3$ are each independently unsubstituted or substituted with 1, 2, 3, 4, or 5 substituents independently selected from the group consisting of $C_1$-$C_4$ alkyl, $C_2$-$C_4$ alkenyl, $C_2$-$C_4$ alkynyl, halogen, —CN, oxo, —$OR^m$, —S(O)$_2$$R^n$, —S(O)$_2$N($R^m$)$_2$, —C(O)$R^m$, —C(O)N($R^m$)$_2$, —N($R^m$)$_2$, —N($R^m$)C(O)$R^m$, —N($R^m$)S(O)$_2$$R^n$, —N($R^m$)C(O)N($R^m$)$_2$, and —$(CR^eR^f)_r$—O(haloalkyl);
$R^m$, at each occurrence, is independently hydrogen, $C_1$-$C_4$ alkyl or $C_3$-$C_6$ cycloalkyl;
$R^n$, at each occurrence, is independently $C_1$-$C_4$ alkyl or $C_3$-$C_6$ cycloalkyl;
r is 1, 2, 3, or 4; and
s is 2, 3, or 4.
Yet other compounds included are those having formula (IV) or (V) wherein
$X^1$ is $CH_2$, $X^2$ is O, and p is 1 or 2; or
$X^1$ is $CH_2CH_2$, $X^2$ is O, and p is 1; or X¹ is O, X² is CH₂, and p is 2;
q is 0, 1, 2, 3, or 4;
═══ is a single bond or a double bond;
$R^x$ is selected from the group consisting of oxo, methyl, and —OH;
$T^1$ is —$OR^a$;
$T^2$ is halogen, —CN, or trifluoromethyl;
$R^2$ is n-butyl, isobutyl, n-pentyl, —(CH₂)-G², —(CH₂)₂—CN, —(CH₂)₃—CN, or —(CH₂)₄—CN;
$R^a$ is methyl, ethyl, isopropyl, n-propyl, trifluoromethyl, 2,2,2-trifluoroethyl, or 2-fluoroethyl; and
$G^2$ is cyclopropyl, cyclobutyl, or cyclopentyl, each of which is optionally substituted as described generally and in embodiments herein above.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. BIOLOGICAL DATA (i) In Vitro Methods—CB₂ and CB₁ Radioligand Binding Assays:

The CB₁ and CB₂ radioligand binding assays described herein are utilized to ascertain the selectivity of compounds of the present application for binding to CB₂ relative to CB₁ receptors.

HEK293 cells stably expressing human CB₂ receptors were grown until a confluent monolayer was formed. Briefly, the cells were harvested and homogenized in TE buffer (50 mM Tris-HCl, 1 mM MgCl₂, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM MgCl₂, and 1 mM EDTA and 10% sucrose) and frozen at −78° C. until used. Saturation binding reactions were initiated by the addition of membrane preparation (protein concentration of 5 μg/well for human CB₂) into wells of a deep well plate containing [³H] CP-55,940 (120 Ci/mmol, a nonselective CB agonist commercially available from Tocris) in assay buffer (50 mM Tris, 2.5 mM EDTA, 5 mM MgCl₂, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [³H]CP-55,940 ranging from 0.01 to 8 nM. Competition experiments were conducted with 0.5 nM [³H]CP-55,940 and five concentrations (1 nM to 10 μM) of displacing ligands. The addition of 10 μM unlabeled CP-55,940 (Tocris, Ellisville, Mo.) was used to assess non-specific binding.

The majority of the compounds of the present application bound to CB₂ receptors with an affinity ($K_i$) of less than about 1,000 nM, preferably less than 400 nM, more preferably less than 200 nM, and most preferably lower than 100 nM.

HEK293 human CB₁ membranes were purchased from Perkin Elmer. Binding was initiated by the addition of membranes (8-12 μg per well) into wells (Scienceware 96-well DeepWell plate, VWR, West Chester, Pa.) containing [³H] CP-55,940 (120 Ci/mmol, Perkin Elmer, Boston, Mass.) and a sufficient volume of assay buffer (50 mM Tris, 2.5 mM EDTA, 5 mM MgCl₂, and 0.5 mg/mL fatty acid free BSA, pH 7.4) to bring the total volume to 250 μL. After incubation (30° C. for 90 minutes), binding was terminated by the addition of 300 μL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [³H]CP-55,940 and five concentrations (1 nM to 10 μM) of displacing ligands. The addition of 10 μM unlabeled CP-55,940 (Tocris, Ellisville, Mo.) was used to assess nonspecific binding. The majority of the compounds of the present application tested for CB₁ binding, bound to CB₁ receptors with affinities ($K_i$) 10×-1000× higher than the $K_i$ for CB₂. These results show that the compounds of the present application preferably bind to CB₂ receptors, therefore are selective ligands for the CB₂ receptor.

ii) In Vivo Data Animals

Adult male Sprague-Dawley rats (250-300 g body weight, Charles River Laboratories, Portage, Mich.) are used. Animal handling and experimental protocols are approved by the Institutional Animal Care and Use Committee (IACUC) at Abbott Laboratories. For all surgical procedures, animals are maintained under isoflurane anesthesia (4-5% to induce, 1-3% to maintain), and the incision sites are sterilized using a 10% povidone-iodine solution prior to and after surgeries.

Incision Model of Postoperative Pain

A skin incision model of postoperative pain was produced using the procedures previously described (Brennan et al., 1996, Pain, 64, 493). All rats were anesthetized with isoflurane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, W. J., 1980, Efficient analysis of experimental observations, Ann. Rev. Pharmacol. Toxicol. 20, 441).

Representative compounds of the present application showed a statistically significant change in paw withdrawal latency versus a saline vehicle at less than about 300 micromoles/kg in the incision model of postoperative pain. In a more preferred embodiment, compounds of the present application showed efficacy at less than about 50 micromoles/kg in the incision model of postoperative pain.

Spinal Nerve Ligation Model of Neuropathic Pain

A model of spinal nerve ligation-induced (SNL model) neuropathic pain as originally described by Kim and Chung (Kim, S. H. and J. M. Chung, 1992, Pain 50, 355) can be used to test the compounds of the present application The left L5 and L6 spinal nerves of the rat are isolated adjacent to the vertebral column and tightly ligated with a 5-0 silk suture distal to the DRG, and care is taken to avoid injury of the L4 spinal nerve. Sham rats undergo the same procedure, but without nerve ligation. All animals are allowed to recover for at least one week and not more than three weeks prior to assessment of tactile allodynia.

Tactile allodynia is measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53.55. Rats are placed into inverted individual plastic containers (20×12.5×20 cm) on top of a suspended wire mesh grid, and acclimated to the test chambers for 20 minutes. The von Frey filaments are presented perpendicularly to the plantar surface of the selected hind paw, and then hold in this position for approximately 8 sec with enough force to cause a slight bend in the filament. Positive responses include an abrupt withdrawal of the hind paw from the stimulus, or flinching behavior immediately following removal of the stimulus. A 50% withdrawal threshold is determined using an up-down procedure (Dixon, W. J., 1980, Efficient analysis of experimental observations, Ann. Rev. Pharmacol. Toxicol. 20, 441). Only rats with a baseline threshold score of less that 4.25 g are used in this study, and animals demonstrating motor deficit are excluded. Tactile allodynia thresholds are also assessed in several control groups, including naive, sham-operated, and saline infused animals as well as in the contralateral paws of nerve-injured rats.

Capsaicin-Induced Secondary Mechanical Hypersensitivity:

Rats were allowed to acclimate to the study room for 1 h. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds were injected (i.p.) 30 min before testing (150 min post-capsaicin).

Tactile allodynia was measured as described above.

Representative compounds of the present application showed a statistically significant change in paw withdrawal latency versus a saline vehicle at less than about 300 micromoles/kg in the capsaicin model of secondary mechanical hyperalgesia. In a more preferred embodiment, compounds of the present application showed efficacy at less than about 50 micromoles/kg in the capsaicin model of secondary mechanical hyperalgesia.

d. METHODS OF USING THE COMPOUNDS

One embodiment of the present invention provides a method for treating pain (for example, neuropathic pain or nociceptive pain) in a mammal (including human) in need of such treatment. The method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID).

Yet another embodiment of the present invention relates to a method for providing neuroprotection in a mammal in need of such treatment. This method comprises administering to the mammal a therapeutically effective amount of a compound of the invention or a pharmaceutically acceptable salt thereof.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. —Neuroinflammation occurs in several neurodegenerative diseases, and induction of microglial $CB_2$ receptors has been observed (Carrier, E. J., et al., Current Drug Targets —CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). CB$_2$ receptor expression has been detected on osteoclasts and osteoblastic precursor cells, and administration of a CB$_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the CB$_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, CB$_2$ modulators may be useful for the treatment and prevention of osteoporosis, osteoarthritis, and bone disorders.

Atherosclerosis is a chronic inflammatory disease and is a leading cause of heart disease and stroke. CB$_2$ receptors have been detected in both human and mouse atherosclerotic plaques. Administration of low doses of THC in apolipoprotein E knockout mice slowed the progression of atherosclerotic lesions, and these effects were inhibited by the CB$_2$-selective antagonist SR144528 (Steffens, S., et al., Nature, 2005, 434, 782-786). Thus, compounds with activity at the CB$_2$ receptor may be clinically useful for the treatment of atherscelorsis.

CB$_2$ receptors are expressed on malignant cells of the immune system and targeting CB$_2$ receptors to induce apoptosis may constitute a novel approach to treating malignancies of the immune system. Selective CB$_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, CB$_2$ modulators may have utility as anticancer agents against tumors of immune origin.

Activation of CB$_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, CB$_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.1 mg/kg body weight to about 100 mg/kg body weight. More preferable doses can be in the range of from about 0.3 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. PHARMACEUTICAL COMPOSITIONS

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising compounds of the invention, or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. GENERAL SYNTHESIS

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $R^1$, $R^2$, $R^3$, and $R^4$ have the meanings as set forth in the summary section unless otherwise noted, can be synthesized as shown in Schemes 1-7.

Abbreviations which have been used in the descriptions of the Schemes and the Examples that follow are: DMAP for 4-(dimethylamino)pyridine, DMF for N,N-dimethylformamide, DMSO for dimethyl sulfoxide, EDCI for 1-(3-dimethylaminopropyl)-3-ethylcarbodiimide hydrochloride, EtOAc for ethyl acetate, $CHCl_3$ for chloroform, $CH_2Cl_2$ for dichloromethane, $CH_3CN$ for acetonitrile, HOBt for 1-hydroxybenzotriazole hydrate; MeOH for methanol, THF for tetrahydrofuran; BOC for tert-butoxycarbonyl; and DMSO for dimethylsulfoxide.

Compounds of general formula (I) can be prepared using general procedures as outlined in Scheme 1.

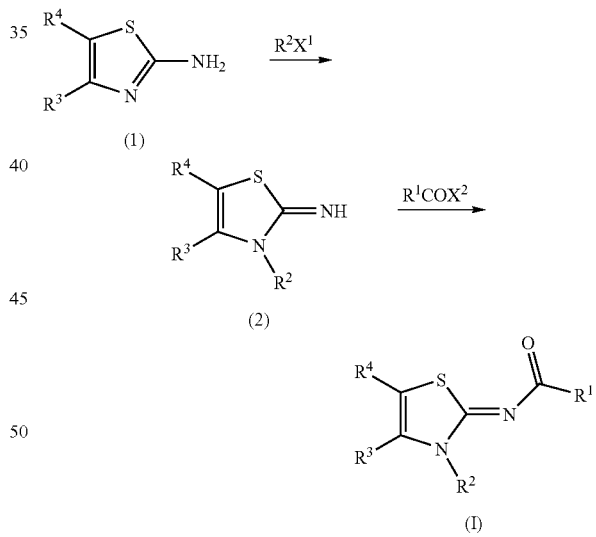

Thiazoles of formula (I) when treated with compounds of formula $R^2X^{101}$ wherein $X^{101}$ is a good leaving group such as, but not limited to, halide, mesylate or tosylate, with heating between about 50° C. to about 150° C., and optionally in the presence of a solvent such as N,N-dimethylformamide, dimethylsulfoxide, dioxane or tetrahydrofuran, provide compounds of formula (2). In certain cases the presence of a base such as a tertiary amine (for example, triethylamine), or an inorganic base such as potassium carbonate or sodium hydride, may be beneficial. When treated with an acid halide of formula $R^1COX^{102}$ wherein $X^{102}$ is chloride or bromide, in a solvent such as but not limited to tetrahydrofuran, diethyl ether or dichloromethane, and in the presence of a base such as, but not limited to, triethylamine or 4-dimethylaminopyridine, compounds of formula (2) can be converted to compounds of general formula (I). Alternatively (2) can be coupled with a carboxylic acid of formula $R^1COOH$, using standard amide bond forming conditions.

Alternatively, compounds of general formula (I) can also be prepared using general procedures as illustrated in Scheme 2.

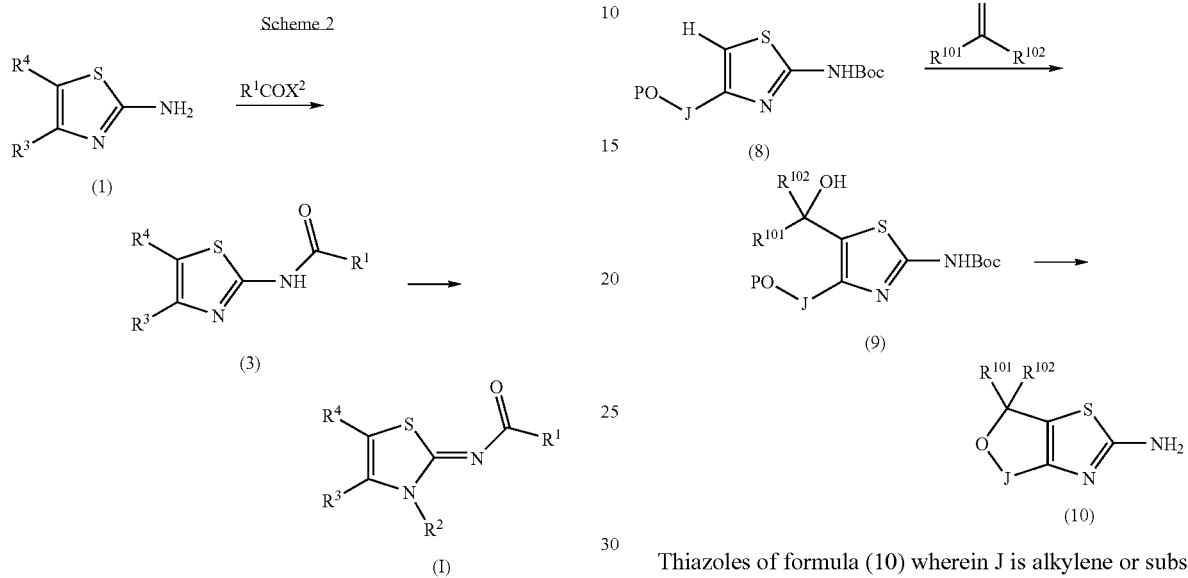

Thiazoles of formula (I) can be treated with acids of formula $R^1COOH$ or acid halides of formula $R^1COX^{102}$ using reaction conditions for the conversion of (2) to (I) in Scheme 1, to afford compounds of formula (3). Compounds of formula (3) can be transformed to compounds of general formula (I) by treating with compounds of formula $R^2X^{101}$, using reaction conditions for the transformation of (1) to (2) in Scheme 1.

Thiazoles of formula (I) wherein $R^3$ and $R^4$ form a monocyclic ring can be prepared as shown in Scheme 3.

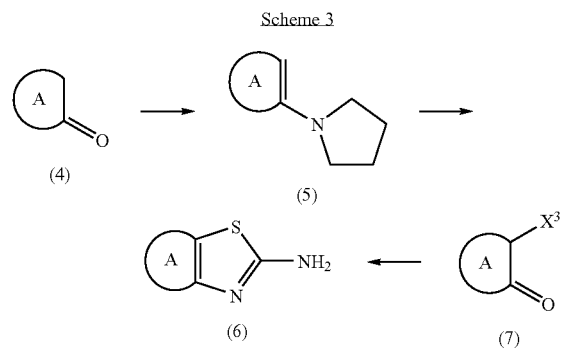

Thiazoles of formula (6) wherein A is a monocyclic ring as defined in general formula (I) can be prepared by (a) treating an appropriate ketone of formula (4) with pyrrolidine in cyclohexane; and (b) treating the enamine of formula (5) obtained from step (a) with sulfur and cyanamide in a solvent such as but not limited to methanol and ethanol, at a temperature from about 0° C. to about 50° C. Step (a) is generally conducted in the presence of a dehydrating agent, such as magnesium sulfate or molecular sieves, or alternatively through the use of a Dean-Stark trap with heating in the presence of a catalytic amount of p-toluenesulfonic acid.

An appropriate haloketone of formula (7) wherein $X^3$ is Cl or Br, when treated with thiourea, provides thiazoles of formula (6). The reaction is generally conducted in the presence of a base such as, but not limited to, triethylamine, in a solvent such as, but not limited to, ethanol, and at a temperature from about 25° C. to about 100° C.

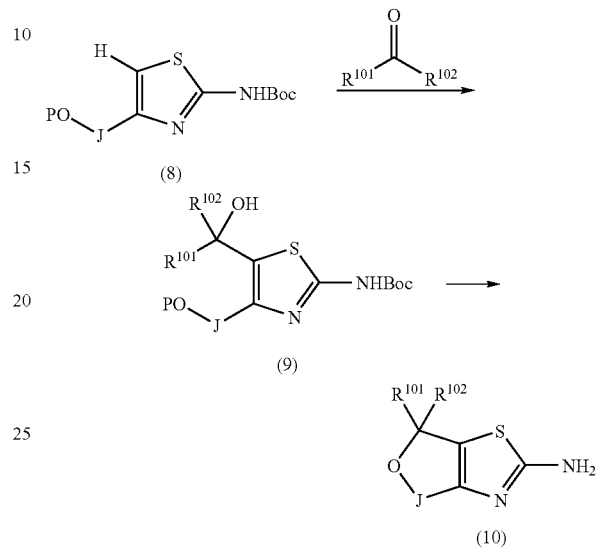

Thiazoles of formula (10) wherein J is alkylene or substituted alkylene can be prepared using the 2 step method as illustrated in Scheme 4. Thiazoles of formula (8) wherein the P is an oxygen protecting group such as, but not limited to, tetrahydropyranyl, t-butyldimethylsilyl, triisopropylsilyl, or methoxymethyl, can be converted to compounds of formula (9) by (a) reacting with excess (at least 2 equivalents) lithium diisopropylamide in a solvent such as tetrahydrofuran or diethyl ether; and (b) treating the intermediate obtained from step (a) with an appropriate aldehyde or ketone of formula $R^{101}C(O)R^{102}$, wherein $R^{101}$ and $R^{102}$ can be the same of different, and are independently hydrogen, alkyl, or haloalkyl, or $R^{101}$ and $R^{102}$ may form an optionally substituted monocyclic cycloalkyl ring. Treatment of (9) with an acid such as, but not limited to, hydrochloric acid at a temperature from about room temperature to about 100° C. removes the nitrogen and oxygen protecting groups and leads to the cyclization of the intermediates formed, providing thiazoles of formula (10). Alternatively, (9) can be converted to (10) by a stepwise reaction wherein the oxygen protecting group is first removed, followed by activation of the oxygen as the corresponding halide or mesylate prior to cyclization. Another alternative would be to conduct the cyclization using Mitsunobu or with dicyclohexylcarbodiimide conditions that are well known to those skilled in the art.

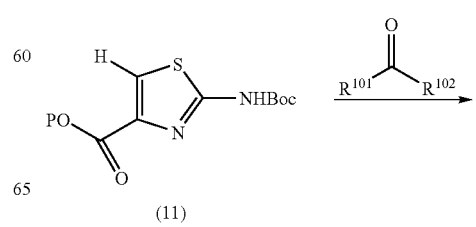

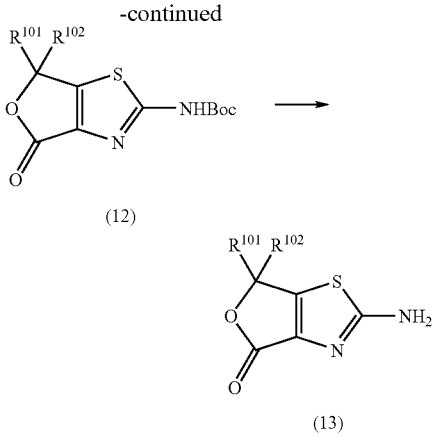

(12)

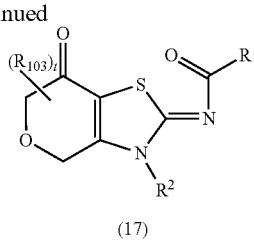

(17)

5-hydroxy-2H-pyran-3(6H)-ones of formula (14) wherein $R^{103}$ is selected from alkyl, halogen, —OH, —O(alkyl), or haloalkyl, and t is 0, 1, 2, 3, 4, or 5, or the corresponding salts such as sodium salt, can be treated with thioureas of formula (15), in the presence of DMSO/hydrochloric acid, at a temperature ranging from about room temperature to about 120° C., to provide compounds of formula (16). The reaction can be conducted in a solvent such as, but not limited to, dioxane or tetrahydrofuran, or mixture thereof.

Conversion of (16) to (17) can be accomplished using reaction conditions as described in Scheme 1.

Compounds of general formula (I) wherein $R^3$ and $R^4$, together with the carbon atoms to which they are attached, form a tetrahydropyranyl ring can be prepared using general methodology as described in Scheme 7.

Thiazole intermediates of formula (13) can be prepared using the 2-step method illustrated in Scheme 5. Thiazoles of formula (11) wherein P is alkyl, benzyl or allyl can be reacted with excess (at least 2 equivalents) lithium diisopropylamide in a solvent such as tetrahydrofuran or diethyl ether, followed by reaction with an appropriate aldehyde or ketone of formula $R^{101}C(O)R^{102}$ wherein $R^{101}$ and $R^{102}$ are as defined above, to generate intermediates of formula (12). Deprotection of this Scheme 7

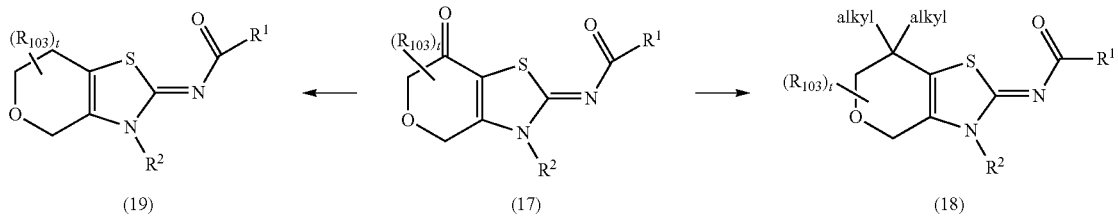

intermediate with an acid such as but not limited to hydrochloric acid or trifluoroacetic acid at about room temperature provides thiazoles of formula (13).

Intermediates of formula (2) wherein $R^3$ and $R^4$, together with the carbon atoms to which they are attached, form a tetrahydropyranyl ring, which is substituted with oxo, and may contain one or more additional substituents as described in formula (I), can be prepared as shown in Scheme 6.

Compounds of formula (17) wherein $R^{103}$ and t are as disclosed in Scheme 6, can be treated with titanium tetrachloride and dialkylzinc to provide compounds of formula (18). The conversion can be conducted in a solvent, for example, in dichloromethane, and at a temperature ranging from about 0° C. to about 50° C.

Compounds of formula (17) when treated with triethylsilane and trifluoroacetic acid, at a temperature from about room temperature to about 120° C., provide compounds of formula (19).

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatogra-

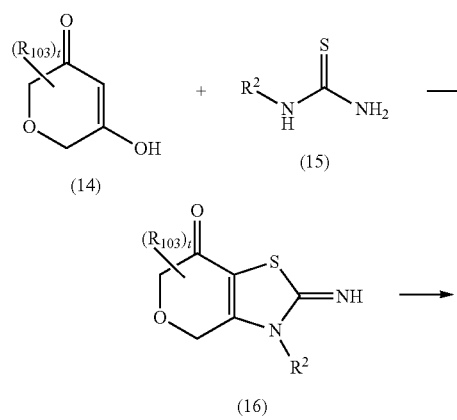

phy. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. EXAMPLES

The compounds and processes of the present application will be better understood by reference to the following Examples, which are intended as an illustration of and not a limitation upon the scope of the application. Compounds of the application were named by ACD/ChemSketch version 5.01 (developed by Advanced Chemistry Development, Inc., Toronto, ON, Canada) or were given names consistent with ACD nomenclature.

Example 1

N-[(2Z)-3-butyl-4,4,6,6-tetramethyl-4,6-dihydrofuro[3,4-d][1,3]thiazol-2(3H)-ylidene]-5-chloro-2-methoxybenzamide Example 1A 4-bromo-2,2,5,5-tetramethyldihydrofuran-3(2H)-one To a solution of 2,2,5,5-tetramethyldihydrofuran-3(2H)-one (Aldrich) (10.0 g, 0.07 mol) in dichloromethane (100 mL) was added bromine (3.6 mL, 0.07 mol) drop wise at room temperature. The reaction mixture was stirred for 2 hours as the brown reaction mixture became a clear solution. The reaction mixture was quenched with the addition of $NaHCO_3$ powder in small portions, filtered and concentrated to provide the title compound as viscous oil (14.1 g, 90%).

Example 1B 4,4,6,6-tetramethyl-4,6-dihydrofuro[3,4-d][1,3]thiazol-2-amine

To a solution of Example 1A (10.0 g, 0.045 mol) in ethanol (100 mL) were added thiourea (3.8 g, 0.05 mol) and triethylamine (6.3 mL, 0.045 mol). The reaction mixture was refluxed overnight, cooled and concentrated under reduced pressure. The residue was diluted with water (25 mL) and extracted with ethyl acetate (3×50 mL). The combined organic extracts were dried ($Na_2SO_4$), filtered and concentrated. The residue was purified by column chromatography ($SiO_2$, 0-5% methanol in dichloromethane) to afford 1.3 g (15%) of the title compound. MS ($ESI^+$) m/z 199 $(M+H)^+$ Example 1C 3-butyl-4,4,6,6-tetramethyl-4,6-dihydrofuro[3,4-d][1,3]thiazol-2(3H)-imine To Example 1B (1.0 g, 5 mmol) was added 1-bromobutane (Aldrich) (3.0 g, 22 mmol) and heated at 120° C. overnight. The reaction mixture was cooled, dissolved in water (20 mL) and washed with ethyl acetate (2×25 mL). The aqueous layer was basified with $NaHCO_3$ and then extracted with ethyl acetate (3×50 mL). The organic extracts were combined, dried ($Na_2SO_4$), filtered and concentrated to yield 0.51 g (40%) of the title compound as a thick oil. MS ($ESI^+$) m/z 255 $(M+H)^+$.

Example 1D 5-chloro-2-methoxybenzoyl chloride

5-Chloro-2-methoxybenzoic acid (11.3 g, 60.56 mmol) and $SOCl_2$ (9 mL, 123.7 mmol) in toluene (20 mL) were heated gently while vigorous gas evolution occurred. After gas evolution had subsided, the reaction was heated to reflux for 1.5 h, cooled and stirred overnight at room temperature. The volatiles were evaporated in vacuo and the remaining material was treated with toluene and evaporated (2×) to remove excess $SOCl_2$. The white solid obtained was taken directly on to the next step without purification. $^1$H NMR (300 MHz, $CDCl_3$) δ 3.92 (s, 3H), 6.95 (d, 1H), 7.53 (dd, 1H), 8.03 (d, 1H).

Example 1E

N-[(2Z)-3-butyl-4,4,6,6-tetramethyl-4,6-dihydrofuro[3,4-d][1,3]thiazol-2(3H)-ylidene]-5-chloro-2-methoxybenzamide To a solution of Example 1C (0.5 g, 2.0 mmol) in tetrahydrofuran (20 mL) were added triethylamine (0.5 mL), 4-dimethylaminopyridine (25.0 mg) and Example 1D (0.45 g, 2.2 mmol). The reaction mixture was stirred at room temperature overnight, diluted with ethyl acetate (20 mL), washed with 1M $NaHCO_3$ (20 mL) and the layers were separated. The aqueous layer was extracted with ethyl acetate (2×20 mL). The combined organic extracts were dried ($Na_2SO_4$), filtered and concentrated. The residue was purified by column chromatography using an Analogix® Intelliflash280™

(Analogix® IT280™) (SiO$_2$, 0-100% ethyl acetate in hexanes) to afford 86 mg (10%) of the title compound. $^1$H NMR (300 MHz, DMSO-d$_6$) δ ppm 0.95 (t, J=7.46 Hz, 3H) 1.36-1.46 (m, 2H) 1.48 (s, 6H) 1.56 (s, 6H) 1.73-1.86 (m, 2H) 3.80 (s, 3H) 4.04 (t, J=6.95 Hz, 2H) 7.13 (d, J=8.82 Hz, 1H) 7.48 (dd, J=8.82, 2.71 Hz, 1H) 7.73 (d, J=3.05 Hz, 1H); MS (ESI$^+$) m/z 423 (M+H)$^+$; Anal. Calculated for C$_{21}$H$_{27}$ClN$_2$O$_3$S: C, 59.63; H, 6.43; N, 6.62. Found: C, 59.77; H, 6.44; N, 6.67.

Example 2

5-chloro-N-[(2Z)-3-(2,4-difluorobenzyl)-4,4,6,6-tetramethyl-4,6-dihydrofuro[3,4-d][1,3]thiazol-2(3H)-ylidene]-2-methoxybenzamide Example 2A 5-chloro-2-methoxy-N-(4,4,6,6-tetramethyl-4,6-dihydrofuro[3,4-d][1,3]thiazol-2-yl)benzamide Example 1B, triethylamine, 4-dimethylaminopyridine and example 1D were processed as described in Example 1E to obtain the title compound. MS (ESI$^+$) m/z 367 (M+H)$^+$ Example 2B 5-chloro-N-[(2Z)-3-(2,4-difluorobenzyl)-4,4,6,6-tetramethyl-4,6-dihydrofuro[3,4-d][1,3]thiazol-2(3H)-ylidene]-2-methoxybenzamide To a solution of Example 2A (0.3 g, 0.8 mmol) in N,N-dimethylformamide/tetrahydrofuran (1:4, 10 mL) were added potassium t-butoxide (0.11 g, 1.0 mmol) and 1-(bromomethyl)-2,4-difluorobenzene (Aldrich) (0.21 g, 1.0 mmol). The reaction was stirred at 80° C. overnight and then diluted with ethyl acetate (10 mL). The mixture was washed with 1M NaHCO$_3$ and this aqueous layer was extracted with ethyl acetate (2×20 mL). The combined organic extracts were dried (Na$_2$SO$_4$), filtered and concentrated. The residue was purified by column chromatography using an Analogix® IT280™ (SiO$_2$, 0-100% ethyl acetate in hexanes) to afford 20 mg (5%) of the title compound. $^1$H NMR (300 MHz, DMSO-d$_6$) δ ppm 1.47 (s, 6H) 1.52 (s, 6H) 3.72 (s, 3H) 5.35 (s, 2H) 7.07 (d, 3H) 7.32 (d, 1H) 7.37 (d, J=2.71 Hz, 1H) 7.40-7.50 (m, J=8.81 Hz, 1H); MS (ESI$^+$) m/z 493 (M+H)$^+$.

Example 3

N-[(2Z)-1-butyl-4,4-dimethyl-1,4,6,7-tetrahydro-2H-pyrano[4,3-d][1,3]thiazol-2-ylidene]-5-chloro-2-methoxybenzamide Example 3A ethyl{2-[(tert-butoxycarbonyl)amino]-1,3-thiazol-4-yl}acetate The title compound was obtained from ethyl 2-(2-aminothiazol-4-yl)acetate (purchased from Aldrich) using the procedure as described in JP 06345736. The crude product was used in the next step without purification. MS (ESI$^+$) m/z 287 (M+H)$^+$ Example 3B tert-butyl 4-(2-hydroxyethyl)-1,3-thiazol-2-ylcarbamate To a cooled solution of crude Example 3A in tetrahydrofuran (100 mL) was added lithium borohydride (100 mL, 2M solution in tetrahydrofuran) at 0° C. The reaction mixture was refluxed overnight, cooled with an ice bath, quenched with water and extracted with ethyl acetate (3×100 mL). The combined organic extracts were dried (Na$_2$SO$_4$), filtered and concentrated. The residue was purified by column chromatography using an Analogix® IT280™ (SiO$_2$, 0-5% methanol in dichloromethane) to afford 6.3 g (26%) of the title compound. MS (ESI$^+$) m/z 245 (M+H)$^+$ Example 3C tert-butyl 4-[2-(tetrahydro-2H-pyran-4-yloxy)ethyl]-1,3-thiazol-2-ylcarbamate To a solution of Example 3B (6.3 g, 27.4 mmol) in dichloromethane (100 mL) were added commercially available 3,4-dihydro-2H-pyran (purchased from Aldrich) (21 g, 250 mmol) and pyridinium-p-toluenesulfonic acid (purchased from Aldrich) (3.5 g, 14.0 mmol). The reaction mixture was stirred overnight at room temperature and then diluted with dichloromethane, washed with water, dried (Na$_2$SO$_4$), filtered and concentrated. The residue was purified by column chromatography using an Analogix® IT280™ (SiO$_2$, 0-100% ethyl acetate in hexanes) to afford 7.4 g (82%) of the title compound. MS (ESI$^+$) m/z 329 (M+H)$^+$ Example 3D tert-butyl 5-(1-hydroxy-1-methylethyl)-4-[2-(tetrahydro-2H-pyran-4-yloxy)ethyl]-1,3-thiazol-2-ylcarbamate To a solution of diisopropylamine (9.5 mL, 67.2 mmol) in tetrahydrofuran (100 ml) was added butyllithium (42 mL, 1.6M in hexanes, 67.2 mmol) drop wise at -78° C. and stirred for 30 min. Thus obtained lithium diisopropylamide solution was immediately added by cannulation to a solution of Example 3C (7.36 g, 22.4 mmol) in tetrahydrofuran (100 ml) at -78° C. and stirred for 30 min at the same temperature. Then, dry acetone (8.2 ml, 112 mmol, Acros) was added slowly and the reaction mixture was removed from the cold bath and allowed to warm to room temperature with continued stirring overnight. The reaction mixture was quenched with saturated aqueous NH$_4$Cl solution (100 mL) and the aqueous layer was extracted with ethyl acetate (3×100 mL). The combined organic extracts were dried (Na$_2$SO$_4$), filtered and concentrated. The residue was purified by column chromatography using an Analogix® IT280™ (SiO$_2$, 0-100% ethyl acetate in hexanes) to afford 4.6 g (53%) of the title compound. MS (ESI$^+$) m/z 387 (M+H)$^+$ Example 3E 4,4-dimethyl-6,7-dihydro-4H-pyrano[4,3-d][1,3]thiazol-2-amine To a solution of Example 3D (4.6 g, 11 mmol) in tetrahydrofuran was added conc. HCl (6.9 mL). The reaction mixture was refluxed overnight and then cooled to room temperature. The mixture was basified with 5N NaOH (17 mL) and extracted with ethyl acetate (3×50 mL). The combined organic extracts were dried (Na$_2$SO$_4$), filtered and concentrated. The residue was purified by column chromatography using an Analogix® IT280™ (SiO$_2$, 0-10% methanol in dichloromethane to afford 1.04 g (51%) of the title compound. MS (ESI$^+$) m/z 185 (M+H)$^+$

Example 3F 5-chloro-N-(4,4-dimethyl-6,7-dihydro-4H-pyrano[4,3-d][1,3]thiazol-2-yl)-2-methoxybenzamide Example 3E, triethylamine, 4-dimethylaminopyridine, and Example 1D were processed as described in Example 1E to obtain the title compound. MS (ESI$^+$) m/z 353 (M+H)$^+$

Example 3G

N-[(2Z)-1-butyl-4,4-dimethyl-1,4,6,7-tetrahydro-2H-pyrano[4,3-d][1,3]thiazol-2-ylidene]-5-chloro-2-methoxybenzamide Example 3F, 1-bromobutane (purchased from Aldrich) and potassium t-butoxide were processed using the procedure as described for Example 2B to obtain the title compound. $^1$H NMR (300 MHz, DMSO-d$_6$) δ ppm 0.93 (t, J=7.46 Hz, 3H) 1.28-1.38 (m, 2H) 1.45 (s, 6H) 1.63-1.78 (m, 2H) 2.69 (t, J=5.42 Hz, 2H) 3.79 (s, 3H) 3.97 (t, J=5.42 Hz, 2H) 4.07-4.17 (m, 2H) 7.11 (d, J=8.81 Hz, 1H) 7.46 (dd, J=8.81, 2.71 Hz, 1H) 7.69 (d, J=2.71 Hz, 1H); MS (ESI$^+$) m/z 409 (M+H)$^+$; Anal. Calculated for C$_{20}$H$_{25}$ClN$_2$O$_3$S: C, 58.74; H, 6.16; N, 6.85. Found: C, 58.53; H, 6.30; N, 6.83.

Example 4

5-chloro-N-[(2Z)-1-(cyclobutylmethyl)-4,4-dimethyl-1,4,6,7-tetrahydro-2H-pyrano[4,3-d][1,3]thiazol-2-ylidene]-2-methoxybenzamide Example 3F, (bromomethyl)cyclobutane (purchased from Aldrich) and potassium t-butoxide were processed using the procedure as described for Example 2B to obtain the title compound. $^1$H NMR (300 MHz, DMSO-d$_6$) δ ppm 1.45 (s, 6H) 1.75-1.92 (m, 4H) 1.92-2.05 (m, 2H) 2.68 (t, J=5.43 Hz, 2H) 2.74-2.88 (m, 1H) 3.79 (s, 3H) 3.97 (t, J=5.26 Hz, 2H) 4.20 (d, J=7.12 Hz, 2H) 7.12 (d, J=8.82 Hz, 1H) 7.46 (dd, J=8.99, 2.88 Hz, 1H) 7.68 (d, J=3.05 Hz, 1H); MS (ESI$^+$) m/z 421 (M+H)$^+$; Anal. Calculated for C$_{21}$H$_{25}$ClN$_2$O$_3$S: C, 59.92; H, 5.99; N, 6.65. Found: C, 59.68; H, 6.06; N, 6.56.

Example 5

N-[(2Z)-3-butyl-6,6-dimethyl-4-oxo-4,6-dihydrofuro[3,4-d][1,3]thiazol-2(3H)-ylidene]-5-chloro-2-methoxybenzamide

Example 5A tert-butyl 6,6-dimethyl-4-oxo-4,6-dihydrofuro[3,4-d][1,3]thiazol-2-ylcarbamate Methyl 2-(tert-butoxycarbonylamino)thiazole-4-carboxylate (purchased from Combi-Blocks), diisopropylamine, butyllithium, and dry acetone (purchased from Acros) were processed as described in Example 3D to obtain the title compound. MS (ESI$^+$) m/z 285 (M+H)$^+$

Example 5B 2-amino-6,6-dimethylfuro[3,4-d][1,3]thiazol-4(6H)-one

To a solution of Example 5A (7.4 g, 26.0 mmol) in dichloromethane (20 mL) was added trifluoroacetic acid (20.0 ml, 260 mmol) slowly at 0° C. The reaction mixture was removed from the ice bath, allowed to reach room temperature and stirred for 3 hours. The reaction mixture was concentrated to dryness, diluted with ethyl acetate (100 mL) and neutralized with saturated NaHCO$_3$ solution. The layers were separated and the aqueous layer was extracted with ethyl acetate (5×100 mL). The combined organic extracts were dried (Na$_2$SO$_4$), filtered and concentrated to give 4.8 g (99%) of product as a white solid. MS (ESI$^+$) m/z 185 (M+H)$^+$.

Example 5C 5-chloro-N-(6,6-dimethyl-4-oxo-4,6-dihydrofuro[3,4-d][1,3]thiazol-2-yl)-2-methoxybenzamide Example 5B, triethylamine, 4-dimethylaminopyridine, and Example 1D were processed using the procedure as described for Example 1E to obtain the title compound. MS (ESI$^+$) m/z 353 (M+H)$^+$.

Example 5D

N-[(2Z)-3-butyl-6,6-dimethyl-4-oxo-4,6-dihydrofuro[3,4-d][1,3]thiazol-2(3H)-ylidene]-5-chloro-2-methoxybenzamide Example 5C, 1-bromobutane (purchased from Aldrich) and potassium t-butoxide were processed using the procedure as described for Example 2B to obtain the title compound. $^1$H NMR (300 MHz, DMSO-d$_6$) δ ppm 0.93 (t, J=7.46 Hz, 3H) 1.26-1.44 (m, 2H) 1.71 (s, 6H) 1.75-1.89 (m, 2H) 3.82 (s, 3H) 4.29 (t, J=7.12 Hz, 2H) 7.17 (d, J=8.82 Hz, 1H) 7.53 (dd, J=8.82, 2.71 Hz, 1H) 7.78 (d, J=3.05 Hz, 1H); MS (ESI$^+$) m/z 409 (M+H)$^+$; Anal. Calculated for C$_{19}$H$_{21}$ClN$_2$O$_4$S: C, 55.81; H, 5.18; N, 6.85. Found: C, 55.88; H, 4.96; N, 6.70.

Example 6

5-chloro-N-[(2Z)-3-(cyclobutylmethyl)-6,6-dimethyl-4-oxo-4,6-dihydrofuro[3,4-d][1,3]thiazol-2(3H)-ylidene]-2-methoxybenzamide Example 5C, (bromomethyl)cyclobutane (purchased from Aldrich) and potassium t-butoxide were processed using the procedure as described for Example 2B to obtain the title compound. $^1$H NMR (300 MHz, DMSO-d$_6$) δ ppm 1.71 (s, 6H) 1.78-1.91 (m, 4H) 1.91-2.08 (m, 2H) 2.80-3.03 (m, 1H) 3.73-3.97 (m, 3H) 4.35 (s, 2H) 7.17 (d, J=9.16 Hz, 1H) 7.53 (dd, J=8.82, 2.71 Hz, 1H) 7.75 (d, J=2.71 Hz, 1H); MS (ESI$^+$) m/z 421 (M+H)$^+$; Anal. Calculated for C$_{20}$H$_{21}$ClN$_2$O$_4$S: C, 57.07; H, 5.03; N, 6.66. Found: C, 57.07; H, 4.82; N, 6.55.

Example 7

N-[(2'Z)-3'-butyl-4'-oxo-4'H-spiro[cyclobutane-1,6'-furo[3,4-d][1,3]thiazol]-2'(3'H)-ylidene]-5-chloro-2-methoxybenzamide

Example 7A tert-butyl 4'-oxo-4'H-spiro[cyclobutane-1,6'-furo[3,4-d][1,3]thiazol]-2'-ylcarbamate Methyl 2-(tert-butoxycarbonylamino)thiazole-4-carboxylate (purchased from Combi-Blocks), diisopropylamine, butyllithium, and cyclobutanone (purchased from Aldrich)

were processed using the procedure as described for Example 3D to obtain the title compound. MS (ESI+) m/z 297 (M+H)+

Example 7B

2'-amino-4'H-spiro[cyclobutane-1,6'-furo[3,4-d][1,3]thiazol]-4'-one

Example 7A and trifluoroacetic acid were processed using the procedure as described for Example 5B to obtain the title compound. MS (ESI+) m/z 197 (M+H)+

Example 7C 5-chloro-2-methoxy-N-(4'-oxo-4'H-spiro[cyclobutane-1,6'-furo[3,4-d][1,3]thiazol]-2'-yl)benzamide Example 7B, triethylamine, 4-dimethylaminopyridine, and Example 1D were processed using the procedure as described for Example 1E to obtain the title compound. MS (ESI+) m/z 365 (M+H)+.

Example 7D

N-[(2'Z)-3'-butyl-4'-oxo-4'H-spiro[cyclobutane-1,6'-furo[3,4-d][1,3]thiazol]-2'(3'H)-ylidene]-5-chloro-2-methoxybenzamide Example 7C, 1-bromobutane (purchased from Aldrich) and potassium t-butoxide were processed using the procedure as described for Example 2B to obtain the title compound. $^1$H NMR (300 MHz, DMSO-$d_6$) δ ppm 0.92 (t, J=7.29 Hz, 3H) 1.24-1.43 (m, 2H) 1.73-1.86 (m, 2H) 1.84-1.95 (m, 1H) 1.96-2.11 (m, 1H) 2.53-2.64 (m, 2H) 2.67-2.82 (m, 2H) 3.83 (s, 3H) 4.30 (t, J=7.12 Hz, 2H) 7.17 (d, J=9.15 Hz, 1H) 7.54 (dd, J=8.81, 2.71 Hz, 1H) 7.81 (d, J=2.71 Hz, 1H); MS (ESI+) m/z 421 (M+H)+; Anal. Calculated for $C_{20}H_{21}ClN_2O_4S$: C, 57.07; H, 5.03; N, 6.66. Found: C, 57.06; H, 4.59; N, 6.47.

Example 8

N-[(2Z)-3-butyl-6,7-dihydro-4H-pyrano[3,4-d][1,3]thiazol-2(3H)-ylidene]-5-chloro-2-methoxybenzamide

Example 8A 6,7-dihydro-4H-pyrano[3,4-d][1,3]thiazol-2-amine

To a solution of dihydro-2H-pyran-3(4H)-one (purchased from JW-Pharmlab) (5.0 g, 50 mmol) in cyclohexane (100 mL) were added pyrrolidine (4.3 mL, 52 mmol) and p-toluenesulfonic acid monohydrate (0.05 g). The reaction mixture was refluxed for 3 h with a Dean-Stark trap, cooled and concentrated. The residue was dissolved in methanol (80 mL) and then sulfur (1.66 g, 52 mmol) was added. To the mixture was added a solution of cyanamide (2.52 g, 52 mmol) in methanol (20 mL) at 0° C. The reaction mixture was stirred at room temperature overnight, filtered, concentrated and purified by column chromatography using an Analogix® IT280™ (SiO$_2$, 0-5% methanol in dichloromethane) to afford 0.4 g (5%) of the title compound. MS (ESI+) m/z 157 (M+H)+.

Example 8B 5-chloro-N-6,7-dihydro-4H-pyrano[3,4-d][1,3]thiazol-2-yl-2-methoxybenzamide Example 8A, triethylamine, 4-dimethylaminopyridine, and Example 1D were processed using the procedure as described for Example 1E to obtain the title compound. MS (ESI+) m/z 325 (M+H)+

Example 8C

N-[(2Z)-3-butyl-6,7-dihydro-4H-pyrano[3,4-d][1,3]thiazol-2(3H)-ylidene]-5-chloro-2-methoxybenzamide Example 8B, 1-bromobutane (purchased from Aldrich) and potassium t-butoxide were processed using the procedure as described for Example 2B to obtain the title compound. $^1$H NMR (300 MHz, DMSO-$d_6$) δ ppm 0.92 (t, J=7.29 Hz, 3H) 1.20-1.45 (m, 2H) 1.56-1.83 (m, 2H) 2.67 (t, J=5.26 Hz, 2H) 3.79 (s, 3H) 3.91 (t, J=5.42 Hz, 2H) 3.97-4.12 (m, 2H) 4.70 (s, 2H) 7.12 (d, J=8.81 Hz, 1H) 7.46 (dd, J=8.81, 2.71 Hz, 1H) 7.73 (d, J=2.71 Hz, 1H); MS (ESI+) m/z 380 (M+H)+; Anal. Calculated for $C_{18}H_{21}ClN_2O_3S$: C, 56.76; H, 5.56; N, 7.35. Found: C, 56.74; H, 5.29; N, 7.25.

Example 9

5-chloro-N-[(2Z)-3-(cyclobutylmethyl)-6,7-dihydro-4H-pyrano[3,4-d][1,3]thiazol-2(3H)-ylidene]-2-methoxybenzamide

Example 9A 3-(cyclobutylmethyl)-6,7-dihydro-4H-pyrano[3,4-d][1,3]thiazol-2(3H)-imine Example 8A and (bromomethyl)cyclobutane (purchased from Aldrich) were processed using the procedure as described for Example 1C to obtain the title compound. MS (ESI+) m/z 225 (M+H)+

Example 9B 5-chloro-N-[(2Z)-3-(cyclobutylmethyl)-6,7-dihydro-4H-pyrano[3,4-d][1,3]thiazol-2(3H)-ylidene]-2-methoxybenzamide Example 9A, triethylamine, 4-dimethylaminopyridine, and Example 1D were processed using the procedure as described for Example 1E to obtain the title compound. $^1$H NMR (300 MHz, DMSO-$d_6$) δ ppm 1.75-1.88 (m, 4H) 1.89-2.02 (m, 2H) 2.67 (t, J=5.34 Hz, 2H) 2.72-2.88 (m, 1H) 3.80 (s, 3H) 3.91 (t, J=5.34 Hz, 2H) 4.12 (d, J=7.32 Hz, 2H) 4.68 (s, 2H) 7.12 (d, J=8.85 Hz, 1H) 7.12 (d, J=8.85 Hz, 1H) 7.46 (dd, J=8.85, 2.75 Hz, 1H); MS (ESI+) m/z 393 (M+H)+

Example 10

N-[(2Z)-3-butyl-7-oxo-6,7-dihydro-4H-pyrano[3,4-d][1,3]thiazol-2(3H)-ylidene]-5-chloro-2-methoxybenzamide To a mixture of sodium 5-oxo-5,6-dihydro-2H-pyran-3-olate (Wenke et al. J. Org. Chem. 2006, 71, 1725-1727) (1.36 g, 10.0 mmol) and n-butylthiourea (Trans World) (1.32 g, 10.0 mmol) in tetrahydrofuran (15 mL) was added a mixture of DMSO (2.1 mL) and 12 N HCl (2.5 mL). The reaction mixture was heated at 40° C. overnight and cooled. The mixture was diluted with ethyl acetate and washed with aqueous sodium bicarbonate. The organic extract was dried ($MgSO_4$), filtered and concentrated. The residue was dried under vacuum for 12 hours and dissolved in tetrahydrofuran (40 mL). To the solution was added 5-chloro-2-methoxybenzoic acid (1.86 g, 10.0 mmol), N-(3-dimethylaminopropyl)-N-ethylcarbodimide hydrochloride (1.91 g, 10.0 mmol), 1-hydroxybenzotriazole (1.35 g, 10.0 mmol) and triethylamine (3.5 mL, 3.5 mmol). The mixture was stirred overnight at 80° C., then cooled to room temperature. The mixture was diluted with ethyl acetate, washed with 1 M aqueous $NaHCO_3$, dried ($Na_2SO_4$), filtered and concentrated. The residue was purified by flash chromatography using an Analogix® IT280™ ($SiO_2$, 0-75% ethyl acetate in hexanes) to afford 412 mg of the title compound. $^1$H NMR (300 MHz, $CDCl_3$) δ ppm 1.03 (t, J=7.46 Hz, 3H) 1.38-1.52 (m, 2H) 1.77-1.90 (m, 2H) 3.93 (s, 3H) 4.16 (t, J=7.46 Hz, 2H) 4.32 (s, 2H) 4.90 (s, 2H) 6.94 (d, J=8.82 Hz, 1H) 7.40 (dd, J=8.99, 2.88 Hz, 1H) 8.11 (d, J=2.71 Hz, 1H); MS ($ESI^+$) m/z 395 $(M+H)^+$.

Example 11

N-[(2Z)-3-butyl-7,7-dimethyl-6,7-dihydro-4H-pyrano[3,4-d][1,3]thiazol-2(3H)-ylidene]-5-chloro-2-methoxybenzamide To a solution of $TiCl_4$ (purchased from Aldrich) (0.62 mL of 1M in dichloromethane, 0.62 mmol) in dichloromethane (4 mL) was added dimethylzinc (Aldrich, 0.31 mL of 2M in toluene, 0.62 mmol) drop wise at −30° C. and stirred for 10 minutes at the same temperature. Then, a solution of Example 10 (82 mg, 0.21 mmol) in dichloromethane (2 mL) was added drop wise to the reaction mixture and the reaction was allowed to reach room temperature slowly with continued stirring overnight. The reaction mixture was then quenched with 5 mL of 2% $NH_4OH$ aqueous solution, filtered through celite and washed with ethyl acetate (3×10 mL). To the filtrate, 10 mL of saturated $NaHCO_3$ was added and the layers were separated. The aqueous layer was extracted with ethyl acetate (15 mL). The combined organic extracts were dried ($Na_2SO_4$), filtered and concentrated. The residue was purified by column chromatography using an Analogix® IT280™ ($SiO_2$, 0-100% ethyl acetate in hexanes) to afford 52 mg (60%) of the title compound. $^1$H NMR (300 MHz, DMSO-$d_6$) δ ppm 0.92 (t, J=7.34 Hz, 3H) 1.23 (s, 6H) 1.25-1.41 (m, 2H) 1.57-1.79 (m, J=7.34, 7.34 Hz, 2H) 3.60 (s, 2H) 3.79 (s, 3H) 3.93-4.07 (m, 2H) 4.70 (s, 2H) 7.11 (d, J=9.12 Hz, 1H) 7.46 (dd, J=9.12, 2.78 Hz, 1H) 7.69 (d, J=2.78 Hz, 1H); MS ($ESI^+$) m/z 409 $(M+H)^+$; Anal. Calculated $C_{20}H_{25}ClN_2O_3S$: C, 58.74; H, 6.16; N, 6.85. Found: C, 58.45; H, 6.02; N, 6.92.

Example 12

N-[(2Z)-3-butyl-3,4,7,8-tetrahydro-2H-4,7-epoxycyclohepta[d][1,3]thiazol-2-ylidene]-5-chloro-2-methoxybenzamide Example 12A 7,8-dihydro-4H-4,7-epoxycyclohepta[d][1,3]thiazol-2-amine To 8-oxabicyclo[3.2.1]oct-6-en-2-one (prepared as described in Vogel et al. *Tetrahedron* 1993, 49 (8), 1649-1664) (0.5 g, 4.0 mmol) in cyclohexane (3 mL) in a sealable tube was added pyrrolidine (1.7 mL, 20.1 mmol) followed by $MgSO_4$ (4.8 g, 40.3 mmol). The tube was sealed and the mixture was warmed to 100° C. and stirred for 16 hours. The reaction mixture was cooled to ambient temperature, filtered and the filtrate was concentrated under reduced pressure. The residue was dissolved in 10 mL methanol, sulfur (0.13 g, 4.0 mmol) was added and the mixture stirred for 20 min. Cyanamide (0.17 g, 4.0 mmol) was then added and the mixture stirred at ambient temperature for 48 hours. The reaction mixture was concentrated under reduced pressure and purified by flash column chromatography ($SiO_2$, 50% hexanes in ethyl acetate) to give the title compound (90 mg, 0.5 mmol, 12% yield). $^1$H NMR (300 MHz, $CDCl_3$) δ ppm 2.30 (d, J=16.3 Hz, 1H) 3.21 (ddd, J=16.4, 6.0, 1.0 Hz, 1H) 4.64-4.77 (m, 2H) 5.12 (dd, J=5.9, 1.9 Hz, 1H) 5.25-5.29 (m, J=1.9, 1.9 Hz, 1H) 6.00 (dd, J=5.9, 1.9 Hz, 1H) 6.63 (dd, J=5.6, 1.5 Hz, 1H); MS (DCI/$NH_3$) m/z 181 $(M+H)^+$.

Example 12B 3-butyl-3,4,7,8-tetrahydro-2H-4,7-epoxycyclohepta[d][1,3]thiazol-2-imine To the product of Example 12A (90 mg, 0.5 mmol) was added 1-bromobutane (2 mL). This mixture was warmed to 85° C. and was allowed to stir for 16 hours. At this point, insoluble materials were observed so 1 mL N,N-dimethylformamide was added to the reaction mixture and the mixture was stirred for an additional 4 hours at 85° C. The mixture was cooled to ambient temperature and concentrated under reduced pressure. The crude material was purified by column chromatography ($SiO_2$, 10% MeOH in ethyl acetate then 9:1:0.1 $CH_2Cl_2$:methanol:$NH_4OH$) to give a mixture of the title compound and the iminium ion resulting from reaction with N,N-dimethylformamide. This mixture was not separated but was carried on. MS (DCI/$NH_3$) m/z 237 $(M+H)^+$ and m/z 292 (iminium ion).

Example 12C

N-[(2Z)-3-butyl-3,4,7,8-tetrahydro-2H-4,7-epoxycyclohepta[d][1,3]thiazol-2-ylidene]-5-chloro-2-methoxybenzamide To a solution of the product of Example 12B (40 mg, ~0.17 mmol) in tetrahydrofuran (3 ml) was added triethylamine (0.71 μL, 0.19 mmol) followed by Example 1D in 3 mL tetrahydrofuran via cannula. The mixture was warmed to 50° C. and allowed to stir for 2 hours. The mixture was cooled to ambient temperature, quenched with 5 mL saturated, aqueous $NaHCO_3$, extracted 3×5 mL ethyl acetate, dried over anhydrous $Na_2SO_4$, filtered and concentrated under reduced pressure. The mixture was purified by flash column chromatography ($SiO_2$, 30% hexanes in ethyl acetate) to give the title compound (14 mg, 0.035 mmol, 21% yield). $^1$H NMR (300 MHz, $CDCl_3$) δ ppm 1.02 (t, J=7.3 Hz, 3H) 1.36-1.51 (m, 2H) 1.70-1.89 (m, 2H) 2.31 (d, J=16.7 Hz, 1H) 3.19 (dd, J=16.5, 6.5 Hz, 1H) 3.90 (s, 3H) 4.10-4.32 (m, 2H) 5.21 (dd, J=6.1, 1.8 Hz, 1H) 5.30 (s, 1H) 6.13 (dd, J=5.9, 2.0 Hz, 1H) 6.57 (dd, J=5.9, 1.2 Hz, 1H) 6.90 (d, J=8.7 Hz, 1H) 7.33 (dd, J=9.1, 2.8 Hz, 1H) 8.02 (d, J=2.8 Hz, 1H) MS (DCI/$NH_3$) m/z 405

(M+H)$^+$; anal. calculated for $C_{20}H_{21}ClN_2O_3S$: C, 59.33; H, 5.23; N, 6.92. Found: C, 59.50; H, 5.38; N, 6.77.

Example 13

N-[(2Z)-3-butyl-3,4,5,6,7,8-hexahydro-2H-4,7-epoxycyclohepta[d][1,3]thiazol-2-ylidene]-5-chloro-2-methoxybenzamide Example 13A 5,6,7,8-tetrahydro-4H-4,7-epoxycyclohepta[d][1,3]thiazol-2-amine To 8-oxabicyclo[3.2.1]octan-2-one (prepared as described in Vogel et al. *Tetrahedron* 1993, 49 (8), 1649-1664) (1.1 g, 9.0 mmol) in cyclohexane (10 mL) was added pyrrolidine (0.78 mL, 9.4 mmol) and p-TsOH.H$_2$O (0.085 g, 0.45 mmol). The flask was equipped with a Dean-Stark trap that was pre-filled with cyclohexane. The mixture was warmed to reflux and was allowed to stir for 18 hours with the Dean-Stark trap. This mixture was concentrated and redissolved in methanol (15 mL). Sulfur (0.29 g, 9.0 mmol) was added and the mixture stirred for 15 min. Cyanamide (0.38 g, 9.0 mmol) was then added and the mixture was stirred for 72 hours at ambient temperature. The crude mixture was concentrated under reduced pressure and purified by flash column chromatography (SiO$_2$, 20% hexanes in ethyl acetate) to give the title compound (0.75 g, 4.1 mmol, 46% yield). MS (DCI/NH$_3$) m/z 183 (M+H)$^+$.

Example 13B 3-butyl-3,4,5,6,7,8-hexahydro-2H-4,7-epoxycyclohepta[d][1,3]thiazol-2-imine A mixture of the product of Example 13A (0.4 g, 2.2 mmol) and 1-bromobutane (1.9 mL, 17.6 mmol) was warmed to 85° C. and allowed to stir for 1 hour before clumping of solids was observed and a small amount of N,N-dimethylformamide (1 mL) was added. The mixture was stirred for an additional 18 hours at 85° C. then purified by flash column chromatography (SiO$_2$, 10% methanol in ethyl acetate then 9:1:0.1 CH$_2$Cl$_2$:methanol:NH$_4$OH). Two products were obtained, the title compound and the N,N-dimethylformamide-derived iminium ion. The latter was converted to the title compound by washing with 10 mL saturated, aqueous NaHCO$_3$ and extraction with 3×5 mL ethyl acetate. Total yield of the title compound was 0.18 g (0.76 mmol, 34% yield). MS (DCI/NH$_3$) m/z 239 (M+H)$^+$.

Example 13C

N-[(2Z)-3-butyl-3,4,5,6,7,8-hexahydro-2H-4,7-epoxycyclohepta[d][1,3]thiazol-2-ylidene]-5-chloro-2-methoxybenzamide To a solution of the product of Example 13B (0.18 g, 0.76 mmol) in tetrahydrofuran (5 ml) was added triethylamine (0.32 ml, 2.3 mmol) followed by N,N-dimethylpyridin-4-amine (9.2 mg, 0.076 mmol). To this mixture was added Example 1D in 3 mL tetrahydrofuran via cannula. The mixture was warmed to 50° C. and allowed to stir for 4 hours. The mixture was cooled to ambient temperature, quenched with 5 mL saturated, aqueous NaHCO$_3$, extracted 3×10 mL ethyl acetate, dried over anhydrous Na$_2$SO$_4$, filtered and concentrated under reduced pressure. The mixture was purified by flash column chromatography (SiO$_2$, 30% hexanes in ethyl acetate) to give the title compound (0.16 g, 0.39 mmol, 52% yield). $^1$H NMR (300 MHz, CDCl$_3$) δ ppm 1.01 (t, J=7.3 Hz, 3H) 1.46 (dd, J=15.1, 7.5 Hz, 2H) 1.71-1.88 (m, 3H) 2.03-2.13 (m, 1H) 2.16-2.37 (m, 3H) 3.17 (dd, J=15.9, 4.8 Hz, 1H) 3.88-3.92 (m, 3H) 3.93-4.03 (m, 1H) 4.24-4.37 (m, 1H) 4.81-4.90 (m, 1H) 5.05 (d, J=5.6 Hz, 1H) 6.90 (d, J=8.7 Hz, 1H) 7.33 (dd, J=9.1, 2.8 Hz, 1H) 8.03 (d, J=2.8 Hz, 1H) MS (DCI/NH$_3$) m/z 407 (M+H)$^+$; anal. calculated for $C_{20}H_{23}ClN_2O_3S$: C, 59.03; H, 5.70; N, 6.88. Found: C, 58.99; H, 5.35; N, 6.80.

Example 14

5-chloro-N-[(2Z)-1-isobutyl-4,4-dimethyl-1,4,6,7-tetrahydro-2H-pyrano[4,3-d][1,3]thiazol-2-ylidene]-2-methoxybenzamide To a solution of Example 3F (1.0 g, 2.8 mmol) in N,N-dimethylformamide/tetrahydrofuran (1:4, 20 mL) was added potassium tert-butoxide (0.35 g, 3.1 mmol, Aldrich), 1-bromo-2-methylpropane (0.43 g, 3.1 mmol, Aldrich) and tetrabutyl ammonium iodide (0.1 g, 0.3 mmol, Aldrich). After stirring at 80° C. for 16 h, the reaction mixture was cooled to room temperature and quenched with saturated aqueous NaHCO$_3$ (20 mL). The aqueous layer was extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-100% ethyl acetate in hexanes) to afford 90 mg (29%) of the title compound. $^1$H NMR (300 MHz, DMSO-d$_6$) δ ppm 0.81-0.88 (m, 3H), 0.91 (s, 3H), 1.46 (s, 6H), 2.29 (t, 1H), 2.67 (t, J=5.4 Hz, 2H), 3.79 (s, 3H), 3.88-4.11 (m, 4H), 7.12 (d, J=9.1 Hz, 1H), 7.46 (dd, J=8.7, 2.8 Hz, 1H), 7.67 (d, J=3.2 Hz, 1H); MS (ESI$^+$) m/z 409 (M+H)$^+$; Anal. Calculated $CO_1H_{25}ClN_3O_3S$: C, 58.74; H, 60.16; N, 6.85. Found: C, 58.80; H, 5.97; N, 6.88.

Example 15

N-[(2Z)-3-butyl-7-hydroxy-6,7-dihydro-4H-pyrano[3,4-d][1,3]thiazol-2(3H)-ylidene]-5-chloro-2-methoxybenzamide To a solution of Example 10 (50 mg, 0.13 mmol) in tetrahydrofuran (5 mL) was added sodium borohydride (5.8 mg, 0.15 mmol, Aldrich). The reaction mixture was stirred at room temperature for 6 h and then quenched with saturated aqueous NH$_4$Cl solution. The aqueous layer was extracted with EtOAc (2×10 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-5% methanol in methylene chloride) to afford 20 mg (40%) of the title compound. $^1$H NMR (300 MHz, DMSO-d$_6$) δ ppm 0.93 (t, J=7.3 Hz, 3H), 1.24-1.45 (m, 2H), 1.59-1.77 (m, 2H), 3.72 (dd, J=11.7, 4.2 Hz, 1H), 3.80 (s, 3H), 3.84-3.93 (m, 1H), 3.99-4.10 (m, J=7.1 Hz, 2H), 4.56 (d, J=5.2 Hz, 1H), 4.58-4.84 (m, 2H), 5.70 (d, J=5.9 Hz, 1H), 7.12 (d, J=8.7 Hz, 1H), 7.44-7.50 (m, 1H), 7.75 (d, J=2.8 Hz, 1H); MS (ESI$^+$) m/z 397 (M+H)$^+$.

Example 16

N-[(2Z)-3-butyl-7-hydroxy-7-methyl-6,7-dihydro-4H-pyrano[3,4-d][1,3]thiazol-2(3H)-ylidene]-5-chloro-2-methoxybenzamide To a solution of methyllithium (0.8 mL, 1.3 mmol, 1.6M in tetrahydrofuran, Aldrich) in tetrahydrofuran (10 mL) was added slowly a solution of Example 10 (0.25 g, 0.63 mmol) in tetrahydrofuran (5 mL) at −78° C. The reaction mixture was stirred at −78° C. for 30 minutes and was allowed to reach room temperature. The reaction mixture was quenched with water (10 mL) and extracted with EtOAc (2×20 mL). The combined organic extracts were dried over anhydrous $Na_2SO_4$, filtered, and concentrated under reduced pressure. The residue was purified by column chromatography using an Analogix® Intelliflash280™ ($SiO_2$, 0-5% methanol in methylene chloride) to afford 92 mg (35%) of the title compound. $^1$H NMR (300 MHz, DMSO-$d_6$) δ ppm 0.93 (t, J=7.3 Hz, 3H), 1.24-1.37 (m, 2H), 1.39 (s, 3H), 1.56-1.76 (m, 2H), 3.64-3.70 (m, J=3.4 Hz, 2H), 3.79 (s, 3H), 3.92-4.13 (m, 2H), 4.55-4.80 (m, 2H), 5.57 (s, 1H), 7.12 (d, J=9.2 Hz, 1H), 7.46 (dd, J=9.0, 2.9 Hz, 1H), 7.73 (s, 1H)); MS (ESI$^+$) m/z 411 (M+H)$^+$.

Example 17

N-[(2Z)-3-butyl-4,6-dihydrofuro[3,4-d][1,3]thiazol-2 (3H)-ylidene]-5-chloro-2-methoxybenzamide Example 17A 3-butyl-4,6-dihydrofuro[3,4-d]thiazol-2(3H)-imine To a solution of dihydrofuran-3(2H)-one (0.5 g, 6.0 mmol, Small Molecules Inc.) in acetonitrile (10 mL) were added molecular sieves (0.5 g) and butan-1-amine (0.4 g, 5.5 mmol, Aldrich). The reaction mixture was stirred at room temperature overnight and then filtered. To the filtrate was added potassium thiocyanate (0.7 g, 7.3 mmol, Aldrich). The temperature was adjusted to 50° C. and the mixture was stirred until the solids were dissolved. Then, iodine (2.8 g, 10.9 mmol, EMD Chemicals) was added to the mixture and stirred at 50° C. overnight. The reaction mixture was cooled, concentrated and dissolved in EtOAc (15 mL). The solution was washed with Na-meta-bisulfite 20% (15 mL) by mixing the layers for 30 minutes. The organic layer was washed twice with 1N HCl (15 mL). The aqueous layers (metabisulfite and HCl) were combined and the pH was adjusted to pH ~9 by adding $NH_4OH$. The product was extracted with EtOAc (4×20 mL). The combined organic extracts were dried ($Na_2SO_4$), filtered and concentrated to obtain the crude product (0.22 g) of the title compound. MS (ESI$^+$) m/z 199 (M+H)$^+$.

Example 17B

N-[(2Z)-3-butyl-4,6-dihydrofuro[3,4-d][1,3]thiazol-2 (3H)-ylidene]-5-chloro-2-methoxybenzamide To a solution of Example 17A (220 mg, 0.56 mmol) in tetrahydrofuran (10 mL) were added 5-chloro-2-methoxybenzoic acid (114 mg, 0.61 mmol, Aldrich), 1-hydroxybenzotriazole (93 mg, 0.61 mmol, Aldrich), N-(3-dimethylaminopropyl)-N-ethylcarbodiimide hydrochloride (117 mg, 0.61 mmol) and triethylamine (0.23 mL, 1.7 mmol, Aldrich). The reaction mixture was stirred at 80° C. for 2 h, then cooled and quenched with saturated $NaHCO_3$ (10 mL). The aqueous layer was extracted with EtOAc (3×20 mL). The combined organic extracts were dried over anhydrous $Na_2SO_4$, filtered and concentrated under reduced pressure. The residue was purified by column chromatography using an Analogix® Intelliflash280™ ($SiO_2$, 0-100% EtOAc in hexanes) to afford 60 mg (30%) of the title compound. $^1$H NMR (300 MHz, DMSO-$d_6$) δ ppm 0.92 (t, J=7.3 Hz, 3H), 1.33 (t, 2H), 1.74 (t, 2H), 3.80 (s, 3H), 4.10 (t, J=7.3 Hz, 2H), 4.87-5.08 (m, J=1.7 Hz, 4H), 7.13 (d, J=8.8 Hz, 1H), 7.47 (dd, J=8.8, 3.1 Hz, 1H), 7.75 (d, J=3.1 Hz, 1H); MS (ESI$^+$) m/z 367 (M+H)$^+$; Anal. Calculated $C_{17}H_{19}ClN_2O_3S$: C, 55.66; H, 5.22; N, 7.64. Found: C, 55.46; H, 5.03; N, 7.74.

Example 18

5-chloro-N-[(2Z)-3-(cyclobutylmethyl)-4,6-dihydro-furo[3,4-d][1,3]thiazol-2(3H)-ylidene]-2-methoxy-benzamide Example 18A 3-(cyclobutylmethyl)-4,6-dihydrofuro[3,4-d]thiazol-2(3H)-imine Commercially available dihydrofuran-3(2H)-one (Small Molecules Inc.), triethylamine, cyclobutylmethanamine hydrochloride (prepared from cyclobutanecarbonitrile as described in WO 2005075464), potassium thiocyanate (Aldrich) and iodine (EMD chemicals) were processed using the method described in Example 17A to afford the title compound. LC/MS (ESI$^+$) m/z 211 (M+H)$^+$.

Example 18B 5-chloro-N-[(2Z)-3-(cyclobutylmethyl)-4,6-dihydro-furo[3,4-d][1,3]thiazol-2(3H)-ylidene]-2-methoxy-benzamide Example 18A, 5-chloro-2-methoxy-benzoic acid (Aldrich), N-(3-dimethylaminopropyl)-N-ethylcarbodiimide hydrochloride, 1-hydroxybenzotriazole and triethylamine were processed as described for Example 17B to obtain the title compound. $^1$H NMR (300 MHz, DMSO-$d_6$) δ ppm 1.59-1.93 (m, 4H), 1.90-2.11 (m, 2H), 2.73-2.89 (m, 1H), 3.81 (s, 3H), 4.16 (d, J=7.5 Hz, 2H), 4.88-5.05 (m, 4H), 7.13 (d, J=8.7 Hz, 1H), 7.48 (dd, J=8.7, 2.8 Hz, 1H), 7.73 (d, J=2.8 Hz, 1H); MS (ESI$^+$) m/z 379 (M+H)$^+$; Anal. Calculated $C_{18}H_{19}ClN_2O_3S$: C, 57.06; H, 5.05; N, 7.39. Found: C, 56.89; H, 4.84; N, 7.36.

Example 19

5-chloro-N-[(2Z)-3-isobutyl-4,4,6,6-tetramethyl-4,6-dihydrofuro[3,4-d][1,3]thiazol-2(3H)-ylidene]-2-methoxybenzamide Example 19A 3-isobutyl-4,4,6,6-tetramethyl-4,6-dihydrofuro[3,4-d]thiazol-2(3H)-imine Commercially available 2,2,5,5-tetramethyldihydrofuran-3(2H)-one (Aldrich), 2-methylpropan-1-amine (Aldrich), potassium thiocyanate (Aldrich) and iodine (EMD chemicals) were processed using the method described in Example 17A to afford the title compound. MS (ESI$^+$) m/z 255 (M+H)$^+$.

Example 19B 5-chloro-N-[(2Z)-3-isobutyl-4,4,6,6-tetramethyl-4,6-dihydrofuro[3,4-d][1,3]thiazol-2(3H)-ylidene]-2-methoxybenzamide Example 19A, 5-chloro-2-methoxy-benzoic acid (Aldrich), N-(3-dimethylaminopropyl)-N-ethylcarbodiimide hydrochloride, 1-hydroxybenzotriazole and triethylamine were processed as described for Example 17B to obtain the title compound. $^1$H NMR (300 MHz, DMSO-$d_6$) δ ppm 0.92 (d, J=6.8 Hz, 6H), 1.48 (s, 6H), 1.55 (s, 6H), 2.53-2.68 (m, 1H), 3.80 (s, 3H), 3.89 (d, J=7.5 Hz, 2H), 7.13 (d, J=8.8 Hz, 1H), 7.48 (dd, J=8.8, 3.1 Hz, 1H), 7.68 (d, J=3.1 Hz, 1H); MS (ESI$^+$) m/z 423 (M+H)$^+$; Anal. Calculated $C_{21}H_{27}ClN_2O_3S$: C, 59.63; H, 6.43; N, 6.62. Found: C, 59.69; H, 6.46; N, 6.59.

Example 20

5-chloro-N-[(2Z)-3-(cyclobutylmethyl)-4,4,6,6-tetramethyl-4,6-dihydrofuro[3,4-d][1,3]thiazol-2(3H)-ylidene]-2-methoxybenzamide Example 20A 3-(cyclobutylmethyl)-4,4,6,6-tetramethyl-4,6-dihydrofuro[3,4-d]thiazol-2(3H)-imine Commercially available 2,2,5,5-tetramethyldihydrofuran-3(2H)-one (Aldrich), triethyl amine, cyclobutylmethanamine hydrochloride (prepared from cyclobutanecarbonitrile as described in WO 2005075464), potassium thiocyanate (Aldrich) and iodine (EMD chemicals) were processed using the method described in Example 17A to afford the title compound. MS (ESI$^+$) m/z 267 (M+H)$^+$.

Example 20B 5-chloro-N-[(2Z)-3-(cyclobutylmethyl)-4,4,6,6-tetramethyl-4,6-dihydrofuro[3,4-d][1,3]thiazol-2(3H)-ylidene]-2-methoxybenzamide Example 20A, 5-chloro-2-methoxy-benzoic acid (Aldrich), N-(3-dimethylaminopropyl)-N-ethylcarbodiimide hydrochloride, 1-hydroxybenzotriazole and triethylamine were processed as described for Example 17B to obtain the title compound. $^1$H NMR (300 MHz, DMSO-$d_6$) δ ppm 1.48 (s, 6H), 1.55 (s, 6H), 1.73-1.87 (m, 2H), 1.89-2.07 (m, 4H), 2.80-3.00 (m, 1H), 3.81 (s, 3H), 4.13 (d, J=7.1 Hz, 2H), 7.13 (d, J=8.8 Hz, 1H), 7.40-7.55 (m, 1H), 7.70 (d, J=2.7 Hz, 1H); MS (ESI$^+$) m/z 435 (M+H)$^+$; Anal. Calculated $C_{22}H_{27}ClN_2O_3S$: C, 60.75; H, 6.26; N, 6.44. Found: C, 60.75; H, 6.30; N, 6.38.

Example 21

5-chloro-N-[(2Z)-1-(cyclobutylmethyl)-1,4,6,7-tetrahydro-2H-pyrano[4,3-d][1,3]thiazol-2-ylidene]-2-methoxybenzamide Example 21A (Z)-5-chloro-N-(6,7-dihydro-1H-pyrano[4,3-d]thiazol-2(4H)-ylidene)-2-methoxybenzamide To a solution of commercially available 6,7-dihydro-4H-pyrano[4,3-d]thiazol-2-amine (1.73 g, 11.1 mmol, JW-Pharmalab) in tetrahydrofuran/N,N-dimethylformamide (5:1, 60 mL) were added 5-chloro-2-methoxybenzoic acid (2.27 g, 12.2 mmol, Aldrich), 1-hydroxybenzotriazole (1.9 g, 12.2 mmol, Aldrich), N-(3-dimethylaminopropyl)-N-ethylcarbodiimide hydrochloride (2.3 g, 12.2 mmol, Aldrich) and triethylamine (4.6 ml, 33.2 mmol). After stirring at 60° C. for 16 h, the reaction mixture was cooled, diluted with EtOAc (50 mL) and quenched with saturated NaHCO$_3$ (50 mL). The aqueous layer was extracted with EtOAc (2×50 mL). The combined organic extracts were washed with brine (50 mL), dried (Na$_2$SO$_4$), filtered and concentrated under reduced pressure. The residue was purified by column chromatography using an Analogix® Intelliflash280 ™ (SiO$_2$, 0-5% methanol in methylene chloride). MS (ESI$^+$) m/z 325 (M+H)$^+$.

Example 21B 5-chloro-N-[(2Z)-1-(cyclobutylmethyl)-1,4,6,7-tetrahydro-2H-pyrano[4,3-d][1,3]thiazol-2-ylidene]-2-methoxybenzamide Example 21A, (bromomethyl)cyclobutane (Aldrich) and potassium t-butoxide were processed using the procedure as described for Example 2B to obtain the title compound. $^1$H NMR (300 MHz, DMSO-$d_6$) δ ppm 1.76-1.91 (m, 4H), 1.91-2.09 (m, 2H), 2.68-2.78 (m, 2H), 2.77-2.89 (m, J=7.8 Hz, 1H), 3.80 (s, 3H), 3.95 (t, J=5.4 Hz, 2H), 4.21 (d, J=7.5 Hz, 2H), 4.58 (s, 2H), 7.12 (d, J=8.8 Hz, 1H), 7.46 (dd, J=8.8, 2.7 Hz, 1H), 7.71 (d, J=3.1 Hz, 1H); MS (ESI$^+$) m/z 393 (M+H)$^+$; Anal. Calculated $C_{19}H_{21}ClN_2O_3S$: C, 58.08; H, 5.39; N, 7.13. Found: C, 58.32; H, 5.19; N, 7.01.

Example 22

N-[(2Z)-1-butyl-1,4,6,7-tetrahydro-2H-pyrano[4,3-d][1,3]thiazol-2-ylidene]-5-chloro-2-methoxybenzamide Example 21A, 1-bromobutane (Aldrich) and potassium t-butoxide were processed using the procedure as described for Example 2B to obtain the title compound. $^1$H NMR (300 MHz, DMSO-$d_6$) δ ppm 0.93 (t, 3H), 1.22-1.46 (m, 2H), 1.60-1.84 (m, 2H), 2.75 (t, J=5.6 Hz, 2H), 3.79 (s, 3H), 3.96 (t, J=5.4 Hz, 2H), 4.12 (t, 2H), 4.59 (s, 2H), 7.12 (d, J=9.2 Hz, 1H), 7.46 (dd, J=8.8, 2.7 Hz, 1H), 7.73 (d, J=3.1 Hz, 1H); MS (ESI$^+$) m/z 381 (M+H)$^+$; Anal. Calculated $C_{18}H_{21}ClN_2O_3S$: C, 56.76; H, 5.56; N, 7.35. Found: C, 56.74; H, 5.32; N, 7.24.

Example 23

5-chloro-N-[(2Z)-1-isobutyl-1,4,6,7-tetrahydro-2H-pyrano[4,3-d][1,3]thiazol-2-ylidene]-2-methoxybenzamide Example 23A 1-isobutyl-6,7-dihydro-1H-pyrano[4,3-d]thiazol-2(4H)-imine Commercially available dihydro-2H-pyran-4(3H)-one (Aldrich), 2-methylpropan-1-amine (Aldrich), potassium thiocyanate (Aldrich) and iodine (EMD chemicals) were processed using the method described in Example 17A to afford the title compound. MS (ESI$^+$) m/z 213 (M+H)$^+$ Example 23B 5-chloro-N-[(2Z)-1-isobutyl-1,4,6,7-tetrahydro-2H-pyrano[4,3-d][1,3]thiazol-2-ylidene]-2-methoxybenzamide Example 23A, triethylamine, 4-dimethylaminopyridine, and Example 1D were processed using the procedure as described for Example 1E to obtain the title compound. $^1$H NMR (300 MHz, DMSO-d$_6$) δ ppm 0.90 (d, J=6.7 Hz, 6H), 2.26 (d, 1H), 2.73 (d, 2H), 3.79 (s, 3H), 3.96 (t, J=5.9 Hz, 2H), 3.95 (d, J=6.7 Hz, 2H), 4.60 (s, 2H), 7.12 (d, J=8.7 Hz, 1H), 7.42-7.53 (m, 1H), 7.70 (d, J=3.2 Hz, 1H); MS (ESI$^+$) m/z 381 (M+H)$^+$; Anal. Calculated C$_{18}$H$_{21}$ClN$_2$O$_3$S: C, 56.76; H, 5.56; N, 7.35. Found: C, 56.79; H, 5.17; N, 7.28.

Example 24

5-chloro-N-[(2Z)-1-(3-cyanopropyl)-1,4,6,7-tetrahydro-2H-pyrano[4,3-d][1,3]thiazol-2-ylidene]-2-methoxybenzamide Example 21A and 4-bromobutanenitrile (Aldrich) were processed using the procedure as described for Example 2B (sodium hydride used instead of potassium t-butoxide) to obtain the title compound. $^1$H NMR (300 MHz, DMSO-d$_6$) δ ppm 1.99-2.19 (m, 2H), 2.61 (t, J=7.1 Hz, 2H), 2.76 (t, J=5.6 Hz, 2H), 3.80 (s, 3H), 3.97 (t, J=5.4 Hz, 2H), 4.13-4.27 (m, 2H), 4.58 (s, 2H), 7.12 (d, J=8.8 Hz, 1H), 7.45 (dd, J=8.8, 2.7 Hz, 1H), 7.71 (d, J=3.1 Hz, 1H); MS (ESI$^+$) m/z 392 (M+H)$^+$; Anal. Calculated C$_{18}$H$_{18}$N$_3$O$_3$S: C, 55.17; H, 4.63; N, 10.72. Found: C, 54.83; H, 4.58; N, 10.60.

Example 25

N-[(2Z)-1-butyl-1,4,6,7-tetrahydro-2H-pyrano[4,3-d][1,3]thiazol-2-ylidene]-5-cyano-2-methoxybenzamide

Example 25A methyl 5-cyano-2-methoxybenzoate

Commercially available 3-Bromo-4-methoxybenzonitrile (10 g, 47 mmol, Aldrich) in MeOH (100 mL) was treated with triethylamine (9.1 g, 12.5 mL, 90 mmol) and [1,1'-bis(diphenylphosphino)ferrocene]dichloropalladium(II) (1.0 g) in methylene chloride. The mixture was heated at 100° C. under CO at 60 psi for 4 hrs, filtered, and concentrated. The residue was purified by column chromatography using an Analogix® Intelliflash280 ™ (SiO$_2$, 0-50% EtOAc in hexanes) to afford 8.2 g (93%) of the title compound. $^1$H NMR (500 MHz, CHLOROFORM-D) δ ppm 3.92 (s, 3H) 3.98 (s, 3H) 7.06 (d, J=8.54 Hz, 1H) 7.76 (dd, J=8.54, 2.14 Hz, 1H) 8.10 (d, J=2.14 Hz, 1H).

Example 25B 5-cyano-2-methoxybenzoic acid

A mixture of Example 25A (6.1 g, 31.9 mmol) and lithium hydroxide monohydrate (5.36 g, 128 mmol) in tetrahydrofuran (100 mL) and H$_2$O (50 mL) was stirred at room temperature for 3 h. The reaction pH was adjusted to pH=3 with 3N HCl, and the mixture was extracted twice with isopropanol/CH$_2$Cl$_2$ (1:3). The organics were combined, dried (MgSO$_4$), filtered and concentrated to afford 5.6 g (99%) of the title compound. $^1$H NMR (500 MHz, CHLOROFORM-D) δ ppm 4.15 (s, 3H) 7.17 (d, J=8.85 Hz, 1H) 7.86 (dd, J=8.85, 2.44 Hz, 1H) 8.47 (d, J=2.14 Hz, 1H).

Example 25C (Z)-5-cyano-N-(6,7-dihydro-1H-pyrano[4,3-d]thiazol-2(4H)-ylidene)-2-methoxybenzamide Commercially available 6,7-dihydro-4H-pyrano[4,3-d]thiazol-2-amine (Aldrich), Example 25B, N-(3-dimethylaminopropyl)-N-ethylcarbodiimide hydrochloride, 1-hydroxybenzotriazole and triethylamine were processed as described for Example 21A to obtain the title compound. MS (ESI$^+$) m/z 316 (M+H)$^+$.

Example 25D

N-[(2Z)-1-butyl-1,4,6,7-tetrahydro-2H-pyrano[4,3-d][1,3]thiazol-2-ylidene]-5-cyano-2-methoxybenzamide Example 21A and 1-bromobutane (Aldrich) were processed using the procedure as described for Example 2B (sodium hydride used instead of potassium t-butoxide) to obtain the title compound. $^1$H NMR (300 MHz, DMSO-d$_6$) δ ppm 0.83-1.05 (m, J=14.9 Hz, 3H), 1.20-1.52 (m, 2H), 1.63-1.92 (m, 2H), 2.65-2.85 (m, 2H), 3.89 (s, 3H), 3.97 (t, J=5.4 Hz, 2H), 4.06-4.28 (m, 2H), 4.59 (s, 2H), 7.28 (d, J=8.8 Hz, 1H), 7.90 (dd, J=8.8, 2.4 Hz, 1H), 8.10 (d, J=2.4 Hz, 1H)); MS (ESI$^+$) m/z 372 (M+H)$^+$; Anal. Calculated C$_{19}$H$_{21}$N$_3$O$_3$S: C, 61.44; H, 5.70; N, 11.31. Found: C, 60.90; H, 5.56; N, 11.07.

Example 26

N-[(2Z)-1-butyl-6,7-dihydro-5H-pyrano[3,2-d][1,3]thiazol-2(1H)-ylidene]-5-chloro-2-methoxybenzamide

Example 26A 6,7-dihydro-5H-pyrano[3,2-d]thiazol-2-amine

A mixture of dihydro-2H-pyran-3(4H)-one (0.5 g, 5.0 mmol, Small Molecules Inc), piperidine (0.5 mL, 5.0 mmol, Aldrich) and p-toluenesulfonic acid monohydrate (10 mg, 0.05 mmol) in cyclohexane (20 mL) was refluxed for 6 h with a Dean-Stark trap. The reaction mixture was concentrated under reduced pressure. The residue was dissolved in methanol (10 mL). To the above solution were added sulfur (0.16 g, 5.0 mmol) and a solution of cyanamide (0.21 g, 5.0 mmol) in methanol (3 mL) at 0° C. The reaction mixture was stirred at room temperature for 16 h and then concentrated under reduced pressure. The residue was purified by column chromatography using an Analogix® Intelliflash280 ™ (SiO$_2$, 0-5% methanol in methylene chloride) to obtain 60 mg of a product containing two regioisomers (6,7-dihydro-4H-pyrano[3,4-d]thiazol-2-amine (Example 8A) and the title compound 6,7-dihydro-5H-pyrano[3,2-d]thiazol-2-amine (3:1)). MS (ESI$^+$) m/z 157 (M+H)$^+$.

Example 26B 5-chloro-N-(6,7-dihydro-5H-pyrano[3,2-d]thiazol-2-yl)-2-methoxybenzamide To a solution of Example 26A (mixture of isomers) (60 mg, 0.19 mmol) in tetrahydrofuran (10 mL) were added Example 1D (40 mg, 0.19 mmol), triethylamine (0.08 mL, 0.58 mmol), and 4-dimethylaminopyridine (1 mg). After stirring at 60° C. for 14 h, the reaction mixture was cooled and quenched with saturated NaHCO$_3$ (10 mL). The aqueous layer was extracted with EtOAc (3×15 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-50% EtOAc in hexanes) to afford 80 mg of a product containing 5-chloro-N-(6,7-dihydro-4H-pyrano[3,4-d]thiazol-2-yl)-2-methoxybenzamide and the title compound 5-chloro-N-(6,7-dihydro-5H-pyrano[3,2-d]thiazol-2-yl)-2-methoxybenzamide (3:1). MS (APCI) m/z 325 (M+H)$^+$.

Example 26C

N-[(2Z)-1-butyl-6,7-dihydro-5H-pyrano[3,2-d][1,3]thiazol-2(1H)-ylidene]-5-chloro-2-methoxybenzamide To a solution of the product from Example 26B (mixture) in 10 mL of N,N-dimethylformamide and tetrahydrofuran (1:4) were added potassium t-butoxide (21 mg, 0.18 mmol) and 1-bromobutane (25 mg, 0.18 mmol). After stirring at 80° C. for 16 h, the reaction mixture was cooled to room temperature and quenched with saturated aqueous NaHCO$_3$ (10 mL). The aqueous layer was extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-50% ethyl acetate in methylene chloride) to afford 3 mg of the title compound as a single regioisomer. $^1$H NMR (300 MHz, DMSO-d$_6$) δ ppm 0.94 (t, J=7.3 Hz, 3H), 1.28-1.42 (m, 2H), 1.73 (t, 2H), 2.06 (t, 2H), 2.67 (t, J=6.3 Hz, 2H), 3.79 (s, 3H), 4.06-4.13 (m, 2H), 4.18-4.25 (m, 2H), 7.11 (d, J=8.8 Hz, 1H), 7.45 (dd, J=8.8, 3.1 Hz, 1H), 7.71 (d, J=3.1 Hz, 1H); MS (ESI$^+$) m/z 381 (M+H)$^+$.

We claim:

1. A compound of formula (I)

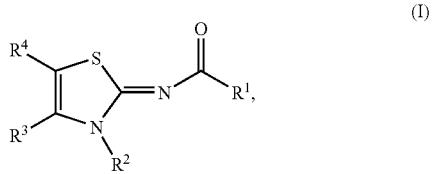

(I)

or a pharmaceutically acceptable salt thereof, wherein $R^1$ is phenyl, wherein the phenyl is independently unsubstituted or substituted by 1, 2, 3, 4, or 5 substituents as represented by T, wherein each T is independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$ R$^d$, —N(R$^b$)C(O)O(R$^a$), —N(R$^b$)C(O)N(R$^b$)(R$^c$)—(CR$^e$R$^f$)$_r$—NO$_2$, —(CR$^e$R$^f$)—OR$^a$, —(CR$^e$R$^f$)$_r$—OC(O)R$^a$, —(CR$^e$R$^f$)$_r$—OC(O)N(R$^b$)(R$^c$), —(CR$^e$R$^f$)$_r$—SR$^a$, —(CR$^e$R$^f$)$_r$—S(O)$_2$R$^d$, —(CR$^e$R$^f$)$_r$—S(O)$_2$N(R$^b$)(R$^c$), —(CR$^e$R$^f$)$_r$—C(O)R$^a$, —(CR$^e$R$^f$)$_r$—C(O)OR$^a$, —(CR$^e$R$^f$)$_r$—C(O)N(R$^b$)(R$^c$), —(CR$^e$R$^f$)$_r$—N(R$^b$)(R$^c$), —(CR$^e$R$^f$)$_r$—N(R$^b$)C(O)R$^a$, —(CR$^e$R$^f$)$_r$—N(R$^b$)S(O)$_2$R$^d$, —(CR$^e$R$^f$)$_r$—N(R$^b$)C(O)O(R$^a$), —(CR$^e$R$^f$)$_r$ —N(R$^b$)C(O)N(R$^b$)(R$^c$), —(CR$^e$R$^f$)$_r$-G$^1$, —(CR$^e$R$^f$)$_r$—CN, haloalkyl, —O—(CR$^e$R$^f$)$_r$—C(O)N(R$^{b1}$)(R$^{c1}$), —O—(CR$^e$R$^f$)$_r$—C(S)N(R$^{b1}$)(R$^{c1}$), —O—(CR$^e$R$^f$)$_r$—S(O)$_2$N(R$^{b1}$)(R$^{c1}$), —O—(CR$^e$R$^f$)$_s$—N(R$^b$)(R$^c$), —O—(CR$^e$R$^f$)$_s$—N(R$^b$)C(O)R$^a$, —O—(CR$^e$R$^f$)$_s$—N(R$^b$)S(O)$_2$R$^d$, and —O—(CR$^e$R$^f$)$_r$—CN;

two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$R$^d$, —N(R$^b$)C(O)O(R$^a$), —N(R$^b$)C(O)N(R$^b$)(R$^c$), —(CR$^e$R$^f$)$_r$—NO$_2$, —(CR$^e$R$^f$)$_r$—OR$^a$, —(CR$^e$R$^f$)$_r$—OC(O)R$^a$, —(CR$^e$R$^f$)$_r$—OC(O)N(R$^b$)(R$^c$), —(CR$^e$R$^f$)$_r$—SR$^a$, —(CR$^e$R$^f$)$_r$—S(O)$_2$R$^d$, —(CR$^e$R$^f$)$_r$—S(O)$_2$N(R$^b$)(R$^c$), —(CR$^e$R$^f$)$_r$—C(O)R$^a$, —(CR$^e$R$^f$)$_r$—C(O)OR$^a$, —(CR$^e$R$^f$)$_r$—C(O)N(R$^b$)(R$^c$), —(CR$^e$R$^f$)$_r$—N(R$^b$)(R$^c$), —(CR$^e$R$^f$)$_r$—N(R$^b$)C(O)R$^a$, —(CR$^e$R$^f$)$_r$—N(R$^b$)S(O)$_2$R$^d$, —(CR$^e$R$^f$)$_r$—N(R$^b$)C(O)O(R$^a$), —(CR$^e$R$^f$)$_r$—N(R$^b$)C(O)N(R$^b$)(R$^c$), —(CR$^e$R$^f$)$_r$- G$^1$, —(CR$^e$R$^f$)$_r$—CN, and haloalkyl;

$R^2$ is —(CH$_2$)-G$^2$;

$R^3$ and $R^4$, together with the atoms to which they are attached, form a 5-membered monocyclic heterocycle; wherein said monocyclic heterocycle contains one oxygen atom, zero nitrogen atoms, zero additional double bonds, no alkenylene or alkylene bridge, and is unsubstituted or substituted with 1, 2, 3, or 4 C$_1$-C$_4$ alkyl groups;

$R^a$, $R^c$, and $R^{c1}$, at each occurrence, are each independently hydrogen, alkyl, haloalkyl, alkoxyalkyl, haloalkoxyalkyl, G$^1$, or —(CR$^e$R$^f$)$_r$-G$^1$;

$R^b$ and $R^{b1}$, at each occurrence, are each independently hydrogen, alkyl, haloalkyl, alkoxyalkyl, cycloalkyl, or haloalkoxyalkyl;

$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^d$, at each occurrence, is independently alkyl, haloalkyl, alkoxyalkyl, cyanoalkyl, G$^1$, or —(CR$^e$R$^f$)$_r$-G$^1$;

$R^e$ and $R^f$, at each occurrence, are each independently hydrogen, alkyl, halogen, or haloalkyl;

r, at each occurrence, is independently 1, 2, 3, 4, 5, or 6;

s, at each occurrence, is independently 2, 3, 4, 5, or 6;

G$^1$, at each occurrence, is independently aryl, heteroaryl, cycloalkyl, cycloalkenyl, or heterocycle;

G$^2$, at each occurrence, is aryl;

wherein the rings as represented by G$^1$ or G$^2$ are each independently unsubstituted or substituted with 1, 2, 3, 4, or 5 substituents independently selected from the group consisting of alkyl, alkenyl, alkynyl, halogen, =N—CN, =N—OR$^n$, —CN, oxo, —NO$_2$, —OR$^m$, —OC(O)R$^m$, —OC(O)N(R$^m$)$_2$, —SR$^m$, —S(O)$_2$R$^n$, —S(O)$_2$N(R$^m$)$_2$, —C(O)R$^m$, —C(O)OR$^m$, —C(O)N(R$^m$)$_2$, —N(R$^m$)$_2$, —N(R$^m$)C(O)R$^m$, —N(R$^m$)S(O)$_2$R$^n$, —N(R$^m$)C(O)O(R$^m$), —N(R$^m$)C(O)N(R$^m$)$_2$, —(CR$^e$R$^f$)$_r$ —NO$_2$, —(CR$^e$R$^f$)$_r$—OR$^m$, —(CR$^e$R$^f$)$_r$—OC(O)R$^m$, —(CR$^e$R$^f$)$_r$—OC(O)N(R$^m$)$_2$, —(CR$^e$R$^f$)$_r$—SR$^m$, —(CR$^e$R$^f$)$_r$—S(O)$_2$R$^n$, —(CR$^e$R$^f$)$_r$—S(O)$_2$N(R$^m$)$_2$, —(CR$^e$R$^f$)$_r$—C(O)R$^m$, —(CR$^e$R$^f$)$_r$—C(O)OR$^m$, —(CR$^e$R$^f$)$_r$—C(O)N(R$^m$)$_2$, —(CR$^e$R$^f$)$_r$—N(R$^m$)$_2$, —(CR$^e$R$^f$)$_r$—N(R$^m$)C(O)R$^m$, —(CR$^e$R$^f$)$_r$—N(R$^m$)S(O)$_2$ R$^n$, —(CR$^e$R$^f$)$_r$—N(R$^m$)C(O)O(R$^m$), —(CR$^e$R$^f$)$_r$—N(R$^m$)C(O)N(R$^m$), —(CR$^e$R$^f$)$_r$—CN, and haloalkyl;

$R^m$, at each occurrence, is independently hydrogen, alkyl, haloalkyl, alkoxyalkyl, cycloalkyl, or haloalkoxyalkyl;

two R$^m$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and $R^n$, at each occurrence, is independently alkyl, haloalkyl, cycloalkyl, cycloalkylalkyl, alkoxyalkyl, or cyanoalkyl, wherein the compound is not a solvate.

2. The compound according to claim 1, wherein the compound is 5-chloro-N-[(2Z)-3-(2,4-difluorobenzyl)-4,4,6,6-tetramethyl-4,6-dihydrofuro[3,4-d][1,3]thiazol-2(3H)-ylidene]-2-methoxybenzamide, or a pharmaceutically acceptable salt thereof.

3. A pharmaceutical composition comprising a therapeutically effective amount of a compound of formula (I) according to claim 1, or a pharmaceutically acceptable salt thereof, in combination with a pharmaceutically acceptable carrier.

4. A compound of formula (I)

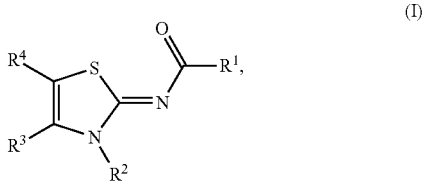

(I)

or a pharmaceutically acceptable salt thereof, wherein $R^1$ is phenyl, wherein the phenyl is independently unsubstituted or substituted by 1, 2, 3, 4, or 5 substituents as represented by T, wherein each T is independently selected from the group consisting of alkyl, alkenyl, alkynyl, halogen, —CN, oxo, -$G^1$, —$NO_2$, —$OR^a$, —$OC(O)R^a$, —$OC(O)N(R^b)(R^c)$, —$SR^a$, —$S(O)R^d$, —$S(O)N(R^b)(R^c)$, $C(O)R^a$, —$C(O)OR^a$, —$C(O)N(R^b)(R^c)$, —$N(R^b)(R^c)$, —$N(R^b)C(O)R^a$, —$N(R^b)S(O)_2R^d$, —$N(R^b)C(O)O(R)$, —$N(R^b)C(O)N(R^b)(R^c)$—$(CR^eR^f)_r$—$NO_2$, —$(CR^eR^f)_r$—$OR^a$, —$(CR^eR^f)_r$—$OC(O)R^a$, $(CR^eR^f)_r$—$OC(O)N(R^b)(R^c)$, —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^b)C(O)R^a$, —$(CR^eR^f)_r$—$N(R^b)S(O)_2R^d$, —$(CR^eR^f)_r$—$N(R^b)C(O)O(R^a)$, —$(CR^eR^f)_r$—N$(R^b)C(O)N(R^b)(R^c)$, —$(CR^eR^f)_r$-$G^1$, —$(CR^eR^f)_r$—CN, haloalkyl, —O—$(CR^eR^f)_r$—$C(O)N(R^{b1})(R^{c1})$, —O—$(CR^eR^f)_r$—$C(S)N(R^{b1})(R^{c1})$, —O—$(CR^eR^f)_r$—$S(O)_2N(R^{b1})(R^c)$, —O—$(CR^eR^f)_s$—$N(R^b)(R^c)$, —O—$(CR^eR^f)_s$—$N(R^b)C(O)R^a$, —O—$(CR^eR^f)_s$—$N(R^b)S(O)_2R^d$, and —O—$(CR^eR^f)_r$—CN;

two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -$G^1$, —$NO_2$, —$OR^a$, —$OC(O)R^a$, —$OC(O)N(R^b)(R^c)$, —$SR^a$, —$S(O)_2R^d$, —$S(O)_2N(R^b)(R^c)$, —$C(O)R^a$, —$C(O)OR^a$, —$C(O)N(R^b)(R^c)$, —$N(R^b)(R^c)$, —$N(R^b)C(O)R^a$, —$N(R^b)S(O)_2R^d$, —$N(R^b)C(O)O(R^a)$, —$N(R^b)C(O)N(R^b)(R^c)$, —$(CR^eR^f)_r$—$NO_2$, —$(CR^eR^f)_r$—$OR^a$, —$(CR^eR^f)_r$—$OC(O)R^a$, —$(CR^eR^f)_r$—$OC(O)N(R^b)(R^c)$, —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^b)C(O)R^a$, —$(CR^eR^f)_r$—$N(R^b)C(O)N(R^b)(R^c)$, —$(CR^eR^f)_r$—$N(R^b)S(O)_2R^d$, —$(CR^eR^f)_r$—$N(R^b)C(O)N(R^b)(R^c)$, —$(CR^eR^f)_r$- $G^1$, —$(CR^eR^f)_r$—CN, and haloalkyl;

$R^2$ is alkyl, alkenyl, alkynyl, $G^2$, —$C(O)R^a$, —$S(O)_2$—$R^d$, —$O(G^1)$, —O—$(CR^eR^f)_r$-$G^1$, —$(CR^eR^f)_s$—O-$G^1$, —$(CR^eR^f)_s$—O—$(CR^eR^f)_r$-$G^3$, —$(CR^eR^f)_r$—$C(O)$—$R^a$, —$(CR^eR^f)_r$—$SO_2$—$R^d$, —$(CR^eR^f)_s$—$N(R^b)(R^c)$, —$(CR^eR^f)_r$-$G^2$, —$(CR^eR^f)_r$-$G^3$, —$(CR^eR^f)_s$—$N(R^b)SO_2R^d$, —$(CR^eR^f)_s$—$N(R^b)COR^a$, —$(CR^eR^f)_s$—$N(R^b)CON(R^b)(R^c)$, —$(CR^eR^f)_s$—$N(R^b)$ $SO_2N(R^b)(R^c)$, —$(CR^eR^f)_r$—$SO_2N(R^b)(R^c)$, —$(CR^eR^f)_r$—$C(O)N(R^b)(R^c)$, —$(CR^eR^f)_r$—CN, haloalkyl, or haloalkoxyalkyl;

$R^3$ and $R^4$, together with the atoms to which they are attached, form a 5-membered monocyclic heterocycle; wherein said monocyclic heterocycle contains one oxygen atom, zero nitrogen atoms, zero additional double bonds, no alkenylene or alkylene bridge, and is substituted with 1 oxo group and 0, 1 or 2 $C_1$-$C_4$ alkyl groups;

$R^a$, $R^c$, and $R^{c1}$, at each occurrence, are each independently hydrogen, alkyl, haloalkyl, alkoxyalkyl, haloalkoxyalkyl, $G^1$, or —$(CR^eR^f)_r$-$G^1$;

$R^b$ and $R^{b1}$, at each occurrence, are each independently hydrogen, alkyl, haloalkyl, alkoxyalkyl, cycloalkyl, or haloalkoxyalkyl;

$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^d$, at each occurrence, is independently alkyl, haloalkyl, alkoxyalkyl, cyanoalkyl, $G^1$, or —$(CR^eR^f)_r$-$G^1$;

$R^e$ and $R^f$, at each occurrence, are each independently hydrogen, alkyl, halogen, or haloalkyl;

r, at each occurrence, is independently 1, 2, 3, 4, 5, or 6;

s, at each occurrence, is independently 2, 3, 4, 5, or 6;

$G^1$, at each occurrence, is independently aryl, heteroaryl, cycloalkyl, cycloalkenyl, or heterocycle;

$G^2$, at each occurrence, is independently aryl, heteroaryl, cycloalkyl, or cycloalkenyl;

$G^3$, is a monocyclic heterocycle containing 1 or 2 nitrogen atoms and 0 or 1 sulfur atom;

wherein the rings as represented by $G^1$, $G^2$, or $G^3$ are each independently unsubstituted or substituted with 1, 2, 3, 4, or 5 substituents independently selected from the group consisting of alkyl, alkenyl, alkynyl, halogen, =N—CN, =N—$OR^n$, —CN, oxo, —$NO_2$, —$OR^m$, —$OC(O)R^m$, —$OC(O)N(R^m)_2$, —$SR^m$, —$S(O)_2R^n$, —$S(O)_2N(R^m)_2$, —$C(O)R^m$, —$C(O)OR^m$, —$C(O)N(R^m)_2$, —$N(R^m)_2$, —$N(R^m)C(O)R^m$, —$N(R^m)S(O)_2R^n$, —$N(R^m)C(O)O(R^m)$, —$N(R^m)C(O)N(R^m)_2$, —$(CR^eR^f)_r$ —$NO_2$, —$(CR^eR^f)_r$—$OR^m$, —$(CR^eR^f)_r$—$OC(O)R^m$, —$(CR^eR^f)_r$—$OC(O)N(R^m)_2$, —$(CR^eR^f)_r$—$SR^m$, —$(CR^eR^f)_r$—$S(O)R^n$, —$(CR^eR^f)_r$—$S(O)_2N(R^m)_2$, —$(CR^eR^f)_r$—$C(O)R^m$, —$(CR^eR^f)_r$—$C(O)OR^m$, —$(CR^eR^f)_r$—$C(O)N(R^m)_2$, —$(CR^eR^f)_r$—$N(R^m)_2$, —$(CR^eR^f)_r$—$N(R^m)C(O)R^m$, —$(CR^eR^f)_r$—$N(R^m)S(O)_2$ $R^n$, —$(CR^eR^f)_r$—$N(R^m)C(O)O(R^m)$, —$(CR^eR^f)_r$—$N(R^m)C(O)N(R^m)$, —$(CR^eR^f)_r$—CN, and haloalkyl;

$R^m$, at each occurrence, is independently hydrogen, alkyl, haloalkyl, alkoxyalkyl, cycloalkyl, or haloalkoxyalkyl;

two $R^m$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and R", at each occurrence, is independently alkyl, haloalkyl, cycloalkyl, cycloalkylalkyl, alkoxyalkyl, or cyanoalkyl, wherein the compound is not a solvate.

5. The compound according to claim 4, wherein $R^2$ is $C_3$-$C_7$ alkyl.

6. The compound according to claim 4, wherein $R^2$ is —$(CH_2)$-$G^2$ and $G^2$ is $C_3$-$C_6$ cycloalkyl.

7. The compound according to claim 4, wherein the compound is selected from the group consisting of:
N-[(2Z)-3-butyl-6,6-dimethyl-4-oxo-4,6-dihydrofuro[3,4-d][1,3]thiazol-2(3H)-ylidene]-5-chloro-2-methoxybenzamide, and
5-chloro-N-[(2Z)-3-(cyclobutylmethyl)-6,6-dimethyl-4-oxo-4,6-dihydrofuro[3,4-d][1,3]thiazol-2(3H)-ylidene]-2-methoxybenzamide,
or a pharmaceutically acceptable salt thereof.

8. A pharmaceutical composition comprising a therapeutically effective amount of a compound of formula (I) according to claim 4, or a pharmaceutically acceptable salt thereof, in combination with a pharmaceutically acceptable carrier.

9. A compound of formula (I)

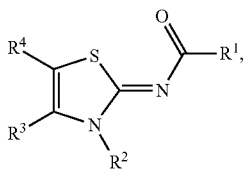

or a pharmaceutically acceptable salt thereof, wherein
$R^1$ is phenyl, wherein the phenyl is independently unsubstituted or substituted by 1, 2, 3, 4, or 5 substituents as represented by T, wherein each T is independently selected from the group consisting of alkyl, alkenyl, alkynyl, halogen, —CN, oxo, -$G^1$, —$NO_2$, —$OR^a$, —OC(O)$R^a$, —OC(O)N($R^b$)($R^c$), —$SR^a$, —S(O)$_2R^d$, —S(O)$_2$N($R^b$)($R^c$), —C(O)$R^a$, —C(O)O$R^a$, —C(O)N($R^b$)($R^c$), —N($R^b$)($R^c$), —N($R^b$)C(O)$R^a$, —N($R^b$)S(O)$_2$ $R^d$, —N($R^b$)C(O)O($R^a$), —N($R^b$)C(O)N($R^b$)($R^c$)—(CR$^e$R$^f$)$_r$—$NO_2$, —(CR$^e$R$^f$)$_r$—$OR^a$, —(CR$^e$R$^f$)$_r$—OC(O)$R^a$, —(CR$^e$R$^f$)$_r$—OC(O)N($R^b$)$R^c$), —(CR$^e$R$^f$)$_r$—$SR^a$, —(CR$^e$R$^f$)$_r$—S(O)$_2R^d$, —(CR$^e$R$^f$)$_r$—S(O)$_2$N($R^b$)($R^c$), —(CR$^e$R$^f$)$_r$—C(O)$R^a$, —(CR$^e$R$^f$)$_r$—C(O)O$R^a$, —(CR$^e$R$^f$)$_r$—C(O)N($R^b$)($R^c$), —(CR$^e$R$^f$)$_r$—N($R^b$)($R^c$), —(CR$^e$R$^f$)$_r$—N($R^b$)C(O)$R^a$, —(CR$^e$R$^f$)$_r$—N($R^b$)S(O)$_2R^d$, —(CR$^e$R$^f$)$_r$—N($R^b$)C(O)O($R^a$), —(CR$^e$R$^f$)$_r$—N($R^b$)C(O)N($R^b$)($R^c$), —(CR$^e$R$^f$)$_r$-$G^1$, —(CR$^e$R$^f$)$_r$—CN, haloalkyl, —O—(CR$^e$R$^f$)$_r$—C(O)N($R^{b1}$)($R^{c1}$), —O—(CR$^e$R$^f$)$_r$—C(S)N($R^{b1}$)($R^{c1}$), —O—(CR$^e$R$^f$)$_r$—S(O)$_2$N($R^{b1}$)($R^{c1}$), —O—(CR$^e$R$^f$)$_s$—N($R^b$)($R^c$), —O—(CR$^e$R$^f$)$_s$—N($R^b$)C(O)$R^a$, —O—(CR$^e$R$^f$)$_s$—N($R^b$)S(O)$_2R^d$, and —O—(CR$^e$R$^f$)$_r$—CN;
two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -$G^1$, —$NO_2$, —$OR^a$, —OC(O)$R^a$, —OC(O)N($R^b$)($R^c$), —$SR^a$, —S(O)$_2R^d$, —S(O)$_2$N($R^b$)($R^c$), —C(O)$R^a$, —C(O)O$R^a$, —C(O)N($R^b$)($R^c$), —N($R^b$)($R^c$), —N($R^b$)C(O)$R^a$, —N($R^b$)S(O)$_2R^d$, —N($R^b$)C(O)O($R^a$), —N($R^b$)C(O)N($R^b$)($R^c$), —(CR$^e$R$^f$)$_r$—$NO_2$, —(CR$^e$R$^f$)$_r$—$OR^a$, —(CR$^e$R$^f$)$_r$—OC(O)$R^a$, —(CR$^e$R$^f$)$_r$—OC(O)N($R^b$)($R^c$), —(CR$^e$R$^f$)$_r$—$SR^a$, —(CR$^e$R$^f$)$_r$—S(O)$_2R^d$, —(CR$^e$R$^f$)$_r$ S(O)$_2$N($R^b$)($R^c$), —(CR$^e$R$^f$)$_r$—C(O)$R^a$, —(CR$^e$R$^f$)$_r$—C(O)O$R^a$, —(CR$^e$R$^f$)$_r$—C(O)N($R^b$)($R^c$), —(CR$^e$R$^f$)$_r$—N($R^b$)($R^c$), —(CR$^e$R$^f$)$_r$—N($R^b$)C(O)$R^a$, —(CR$^e$R$^f$)$_r$—N($R^b$)S(O)$_2R^d$, —(CR$^e$R$^f$)$_r$—N($R^b$)C(O)O($R^a$), —(CR$^e$R$^f$)$_r$—N($R^b$)C(O)N($R^b$)($R^c$), —(CR$^e$R$^f$)$_r$-$G^1$, —(CR$^e$R$^f$)$_r$—CN, and haloalkyl;

$R^2$ is alkyl, alkenyl, alkynyl, $G^2$, —C(O)$R^a$, —S(O)$_2$—$R^d$, —O($G^1$), —O—(CR$^e$R$^f$)$_r$-$G^1$, —(CR$^e$R$^f$)$_s$—O-$G^1$, —(CR$^e$R$^f$)$_s$—O—(CR$^e$R$^f$)$_r$-$G^1$, —(CR$^e$R$^f$)$_r$—C(O)—$R^a$, —(CR$^e$R$^f$)$_r$—SO$_2$—$R^d$, —(CR$^e$R$^f$)$_s$—N($R^b$)($R^c$), —(CR$^e$R$^f$)$_r$-$G^2$, —(CR$^e$R$^f$)$_r$-$G^3$, —(CR$^e$R$^f$)$_s$—N($R^b$) SO$_2R^d$, —(CR$^e$R$^f$)$_s$—N($R^b$)CO$R^a$, —(CR$^e$R$^f$)$_s$—N($R^b$) CON($R^b$)($R^c$), —(CR$^e$R$^f$)$_s$—N($R^b$) SO$_2$N($R^b$)($R^c$), —(CR$^e$R$^f$)$_r$—SO$_2$N($R^b$)($R^c$), —(CR$^e$R$^f$)$_r$—C(O)N($R^b$)($R^c$), —(CR$^e$R$^f$)$_r$—CN, haloalkyl, or haloalkoxyalkyl;

$R^3$ and $R^4$, together with the atoms to which they are attached, form a spiroheterocycle; said spiroheterocycle can be unsubstituted or substituted with 1, 2, 3, 4, or 5 substituents independently selected from the group consisting of oxo, alkyl, halogen, —OH, —O(alkyl), and haloalkyl;

$R^a$, $R^c$, and $R^{c1}$, at each occurrence, are each independently hydrogen, alkyl, haloalkyl, alkoxyalkyl, haloalkoxyalkyl, $G^1$, or —(CR$^e$R$^f$)$_r$-$G^1$;

$R^b$ and $R^{b1}$, at each occurrence, are each independently hydrogen, alkyl, haloalkyl, alkoxyalkyl, cycloalkyl, or haloalkoxyalkyl;

$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^d$, at each occurrence, is independently alkyl, haloalkyl, alkoxyalkyl, cyanoalkyl, $G^1$, or —(CR$^e$R$^f$)$_r$-$G^1$;

$R^e$ and $R^f$, at each occurrence, are each independently hydrogen, alkyl, halogen, or haloalkyl;

r, at each occurrence, is independently 1, 2, 3, 4, 5, or 6;

s, at each occurrence, is independently 2, 3, 4, 5, or 6;

$G^1$, at each occurrence, is independently aryl, heteroaryl, cycloalkyl, cycloalkenyl, or heterocycle;

$G^2$, at each occurrence, is independently aryl, heteroaryl, cycloalkyl, or cycloalkenyl;

$G^3$, is a monocyclic heterocycle containing 1 or 2 nitrogen atoms and 0 or 1 sulfur atom;

wherein the rings as represented by $G^1$, $G^2$, or $G^3$ are each independently unsubstituted or substituted with 1, 2, 3, 4, or 5 substituents independently selected from the group consisting of alkyl, alkenyl, alkynyl, halogen, =N—CN, =N—OR", —CN, oxo, —$NO_2$, —$OR^m$, —OC(O)$R^m$, —OC(O)N($R^m$)$_2$, —$SR^m$, —S(O)$_2R^n$, —S(O)$_2$N($R^m$)$_2$, —C(O)$R^m$, —C(O)O$R^m$, —C(O)N($R^m$)$_2$, —N($R^m$)$_2$, —N($R^m$)C(O)$R^m$, —N($R^m$)S(O)$_2R^n$, —N($R^m$)C(O)O($R^m$), —N($R^m$)C(O)N($R^m$), —(CR$^e$R$^f$)$_r$—$NO_2$, —(CR$^e$R$^f$)$_r$—$OR^m$, —(CR$^e$R$^f$)$_r$—OC(O)$R^m$, —(CR$^e$R$^f$)$_r$—OC(O)N($R^m$)$_2$, —(CR$^e$R$^f$)$_r$—$SR^m$, —(CR$^e$R$^f$)$_r$—S(O)$_2R^n$, —(CR$^e$R$^f$)$_r$—S(O)$_2$N($R^m$)$_2$, —(CR$^e$R$^f$)$_r$—C(O)R$^m$, —(CR$^e$R$^f$)$_r$—C(O)OR$^m$, —(CR$^e$R$^f$)$_r$—C(O)N(R$^m$)$_2$, —(CR$^e$R$^f$, N(R$^m$)$_2$, —(CR$^e$R$^f$)$_r$—N(R$^m$)C(O)R$^m$, —(CR$^e$R$^f$), —N(R$^m$)S(O)$_2$R$^n$, —(CR$^e$R$^f$)$_r$—N(R$^m$)C(O)O(R$^m$), —(CR$^e$R$^f$)$_r$—N(R$^m$)C(O)N(R$^m$)$_2$, —(CR$^e$R$^f$)$_r$—CN, and haloalkyl;

R$^m$, at each occurrence, is independently hydrogen, alkyl, haloalkyl, alkoxyalkyl, cycloalkyl, or haloalkoxyalkyl; two R$^m$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and R$^n$, at each occurrence, is independently alkyl, haloalkyl, cycloalkyl, cycloalkylalkyl, alkoxyalkyl, or cyanoalkyl, wherein the compound is not a solvate.

10. The compound according to claim 9, wherein the compound is N-[(2'Z)-3'-butyl-4'-oxo-4'H-spiro[cyclobutane-1,6'-furo[3,4-d][1,3]thiazol]-2'(3'H)-ylidene]-5-chloro-2-methoxybenzamide, or a pharmaceutically acceptable salt thereof.

11. A pharmaceutical composition comprising a therapeutically effective amount of a compound of formula (I) according to claim 9, or a pharmaceutically acceptable salt thereof, in combination with a pharmaceutically acceptable carrier.

12. A compound of formula (I)

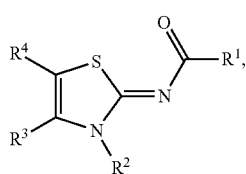

(I)

or a pharmaceutically acceptable salt thereof, wherein

R$^1$ is phenyl, wherein the phenyl is independently unsubstituted or substituted by 1, 2, 3, 4, or 5 substituents as represented by T, wherein each T is independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$R$^d$, —N(R$^b$)C(O)O(R$^a$), —N(R$^b$)C(O)N(R$^b$)(R$^c$)—(CR$^e$R$^f$)$_r$—NO$_2$, —(CR$^e$R$^f$)$_r$—OR$^a$, —(CR$^e$R$^f$)$_r$—OC(O)R$^a$, —(CR$^e$R$^f$)$_r$—OC(O)N(R$^b$)(R$^c$), —(CR$^e$R$^f$)$_r$—SR$^a$, —(CR$^e$R$^f$)$_r$—S(O)$_2$R$^d$, —(CR$^e$R$^f$)$_r$—S(O)$_2$N(R$^b$)(R$^c$), —(CR$^e$R$^f$)$_r$—C(O)R$^a$, —(CR$^e$R$^f$)$_r$—C(O)OR$^a$, —(CR$^e$R$^f$)$_r$—C(O)N(R$^b$)(R$^c$), —(CR$^e$R$^f$)$_r$—N(R$^b$)(R$^c$), —(CR$^e$R$^f$)$_r$—N(R$^b$)C(O)R$^a$, —(CR$^e$R$^f$)$_r$—N(R$^b$)S(O)$_2$R$^d$, —(CR$^e$R$^f$)$_r$—N(R$^b$)C(O)O(R$^a$), —(CR$^e$R$^f$)$_r$—N(R$^b$)C(O)N(R$^b$)(R$^c$), —(CR$^e$R$^f$)$_r$-G$^1$, —(CR$^e$R$^f$)$_r$—CN, haloalkyl, —O—(CR$^e$R$^f$)$_r$—C(O)N(R$^{b1}$)(R$^{c1}$), —O—(CR$^e$R$^f$)$_r$—C(S)N(R$^{b1}$)(R$^{c1}$), —O—(CR$^e$R$^f$)$_r$—S(O)$_2$N(R$^{b1}$)(R$^{c1}$), —O—(CR$^e$R$^f$)$_s$—N(R$^b$)(R$^c$), —O—(CR$^e$R$^f$)$_s$—N(R$^b$)C(O)R$^a$, —O—(CR$^e$R$^f$)$_s$—N(R$^b$)S(O)$_2$R$^d$, and —O—(CR$^e$R$^f$)$_r$—CN;

two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -G$^1$, —NO$_2$, —OR$^a$, —OC(O)R$^a$, —OC(O)N(R$^b$)(R$^c$), —SR$^a$, —S(O)$_2$R$^d$, —S(O)$_2$N(R$^b$)(R$^c$), —C(O)R$^a$, —C(O)OR$^a$, —C(O)N(R$^b$)(R$^c$), —N(R$^b$)(R$^c$), —N(R$^b$)C(O)R$^a$, —N(R$^b$)S(O)$_2$R$^d$, —N(R$^b$)C(O)O(R$^a$), —N(R$^b$)C(O)N(R$^b$)(R$^c$), —(CR$^e$R$^f$)$_r$—NO$_2$, —(CR$^e$R$^f$)$_r$—OR$^a$, —(CR$^e$R$^f$)$_r$—OC(O)R$^a$, —(CR$^e$R$^f$)$_r$—OC(O)N(R$^b$)(R$^c$), —(CR$^e$R$^f$)$_r$—SR$^a$, —(CR$^e$R$^f$)$_r$—S(O)$_2$R$^d$, —(CR$^e$R$^f$)$_r$—S(O)$_2$N(R$^b$)(R$^c$), —(CR$^e$R$^f$)$_r$—C(O)R$^a$, —(CR$^e$R$^f$)$_r$—C(O)OR$^a$, —(CR$^e$R$^f$)$_r$—C(O)N(R$^b$)(R$^c$), —(CR$^e$R$^f$)$_r$—N(R$^b$)(R$^c$), —(CR$^e$R$^f$)$_r$—N(R$^b$)C(O)R$^a$, —(CR$^e$R$^f$)$_r$—N(R$^b$)S(O)$_2$R$^d$, —(CR$^e$R$^f$)$_r$—N(R$^b$)C(O)O(R$^a$), —(CR$^e$R$^f$)$_r$—N(R$^b$)C(O)N(R$^b$)(R$^c$), —(CR$^e$R$^f$)$_r$-G$^1$, —(CR$^e$R$^f$)$_r$—CN, and haloalkyl;

R$^2$ is —(CR$^e$R$^f$)$_r$—CN;

R$^3$ and R$^4$, together with the atoms to which they are attached, form a 6-membered monocyclic heterocycle; wherein said monocyclic heterocycle contains one oxygen atom, zero nitrogen atoms, zero additional double bonds, no alkenylene or alkylene bridge, and is unsubstituted or substituted with 1, 2, 3, or 4 substituents independently selected from the group consisting of alkyl and —OH;

R$^a$, R$^c$, and R$^{c1}$, at each occurrence, are each independently hydrogen, alkyl, haloalkyl, alkoxyalkyl, haloalkoxyalkyl, G$^1$, or —(CR$^e$R$^f$)$_r$-G$^1$;

R$^b$ and R$^{b1}$, at each occurrence, are each independently hydrogen, alkyl, haloalkyl, alkoxyalkyl, cycloalkyl, or haloalkoxyalkyl;

R$^{b1}$ and R$^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

R$^d$, at each occurrence, is independently alkyl, haloalkyl, alkoxyalkyl, cyanoalkyl, G$^1$, or —(CR$^e$R$^f$)$_r$-G$^1$;

R$^e$ and R$^f$, at each occurrence, are each independently hydrogen or methyl;

r, at each occurrence, is independently 2, 3, or 4;

s, at each occurrence, is independently 2, 3, 4, 5, or 6;

G$^1$, at each occurrence, is independently aryl, heteroaryl, cycloalkyl, cycloalkenyl, or heterocycle;

wherein the rings as represented by G$^1$ are each independently unsubstituted or substituted with 1, 2, 3, 4, or 5 substituents independently selected from the group consisting of alkyl, alkenyl, alkynyl, halogen, =N—CN, =N—OR$^n$, —CN, oxo, —NO$_2$, —OR$^m$, —OC(O)R$^m$, —OC(O)N(R$^m$)$_2$, —SR$^m$, —S(O)$_2$R$^n$, —S(O)$_2$N(R$^m$)$_2$, —C(O)R$^m$, —C(O)OR$^m$, —C(O)N(R$^m$)$_2$, —N(R$^m$)$_2$, —N(R$^m$)C(O)R$^m$, —N(R$^m$)S(O)$_2$R$^n$, —N(R$^m$)C(O)O(R$^m$), —N(R$^m$)C(O)N(R$^m$)$_2$, —(CR$^e$R$^f$)$_r$—NO$_2$, —(CR$^e$R$^f$)$_r$—OR$^m$, —(CR$^e$R$^f$)$_r$—OC(O)R$^m$, —(CR$^e$R$^f$)$_r$—OC(O)N(R$^m$)$_2$, —(CR$^e$R$^f$)$_r$—SR$^m$, —(CR$^e$R$^f$)$_r$—S(O)$_2$R$^n$, —(CR$^e$R$^f$)$_r$—S(O)$_2$N(R$^m$)$_2$, —(CR$^e$R$^f$)$_r$—C(O)R$^m$, —(CR$^e$R$^f$)$_r$—C(O)OR$^m$, —(CR$^e$R$^f$)$_r$—C(O)N(R$^m$)$_2$, —(CR$^e$R$^f$)$_r$—N(R$^m$), —(CR$^e$R$^f$)$_r$—N(R$^m$)C(O)R$^m$, —(CR$^e$R$^f$)$_r$—N(R$^m$)S(O)$_2$R$^n$, —(CR$^e$R$^f$)$_r$—N(R$^m$)C(O)O(R$^m$), —(CR$^e$R$^f$)$_r$—N(R$^m$)C(O)N(R$^m$)$_2$, —(CR$^e$R$^f$)$_r$—CN, and haloalkyl;

R$^m$, at each occurrence, is independently hydrogen, alkyl, haloalkyl, alkoxyalkyl, cycloalkyl, or haloalkoxyalkyl; two R$^m$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and R", at each occurrence, is independently alkyl, haloalkyl, cycloalkyl, cycloalkylalkyl, alkoxyalkyl, or cyanoalkyl, wherein the compound is not a solvate.

13. The compound according to claim 12, wherein the compound is 5-chloro-N-[(2Z)-1-(3-cyanopropyl)-1,4,6,7-tetrahydro-2H-pyrano[4,3-d][1,3]thiazol-2-ylidene]-2-methoxybenzamide, or a pharmaceutically acceptable salt thereof.

14. A pharmaceutical composition comprising a therapeutically effective amount of a compound of formula (I) according to claim 12, or a pharmaceutically acceptable salt thereof, in combination with a pharmaceutically acceptable carrier.

15. A compound of formula (I)

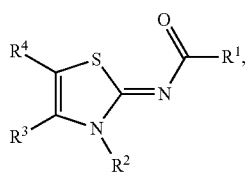

(I)

or a pharmaceutically acceptable salt thereof, wherein $R^1$ is phenyl, wherein the phenyl is independently unsubstituted or substituted by 1, 2, 3, 4, or 5 substituents as represented by T, wherein each T is independently selected from the group consisting of alkyl, alkenyl, alkynyl, halogen, —CN, oxo, -$G^1$, —$NO_2$, —$OR^a$, —$OC(O)R^a$, —$OC(O)N(R^b)(R^c)$, —$SR^a$, —$S(O)_2R^d$, —$S(O)_2N(R^b)(R^c)$, —$C(O)R^a$, —$C(O)OR^a$, —$C(O)N(R^b)(R^c)$, —$N(R^b)(R^c)$, —$N(R^b)C(O)R^a$, —$N(R^b)S(O)_2R^d$, —$N(R^b)C(O)O(R^a)$, —$N(R^b)C(O)N(R^b)(R^c)$—$(CR^eR^f)_r$—$NO_2$, —$(CR^eR^f)_r$—$OR^a$, —$(CR^eR^f)_r$—$OC(O)R^a$, —$(CR^eR^f)_r$—$OC(O)N(R^b)(R^c)$, —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^b)C(O)R^a$, —$(CR^eR^f)_r$—$N(R^b)S(O)_2R^d$, —$(CR^eR^f)_r$—$N(R^b)C(O)O(R^a)$, —$(CR^eR^f)_r$—$N(R^b)C(O)N(R^b)(R^c)$, —$(CR^eR^f)_r$-$G^1$, —$(CR^eR^f)_r$—CN, haloalkyl, —O—$(CR^eR^f)_r$—$C(O)N(R^{b1})(R^{c1})$, —O—$(CR^eR^f)_r$—$C(S)N(R^{b1})(R^{c1})$, —O—$(CR^eR^f)_r$—$S(O)_2N(R^{b1})(R^{c1})$, —O—$(CR^eR^f)_s$—$N(R^b)(R^c)$, —O—$(CR^eR^f)_s$—$N(R^b)C(O)R^a$, —O—$(CR^eR^f)_s$—N$(R^b)S(O)_2R^d$, and —O—$(CR^eR^f)_r$—CN;

two of the adjacent substituents T, together with the atoms to which they are attached optionally form a monocyclic ring selected from the group consisting of phenyl, heterocycle, and heteroaryl, wherein each ring is optionally further substituted with 1, 2, 3, 4, or 5 substituents independently selected from the group consisting of alkyl, alkenyl, alkynyl, halogen, —CN, oxo, -$G^1$, —$NO_2$, —$OR^a$, —$OC(O)R^a$, —$OC(O)N(R^b)(R^c)$, —$SR^a$, —$S(O)_2R^d$, —$S(O)_2N(R^b)(R^c)$, —$C(O)R^a$, —$C(O)OR^a$, —$C(O)N(R^b)(R^c)$, —$N(R^b)(R^c)$, —$N(R^b)C(O)R^a$, —$N(R^b)S(O)_2R^d$, —$N(R^b)C(O)O(R^a)$, —$N(R^b)C(O)N(R^b)(R^c)$, —$(CR^eR^f)_r$—$NO_2$, —$(CR^eR^f)_r$—$OR^a$, —$(CR^eR^f)_r$—$OC(O)R^a$, —$(CR^eR^f)_r$—$OC(O)N(R^b)(R^c)$, —$(CR^eR^f)_r$—$SR^a$, —$(CR^eR^f)_r$—$S(O)_2R^d$, —$(CR^eR^f)_r$—$S(O)_2N(R^b)(R^c)$, —$(CR^eR^f)_r$—$C(O)R^a$, —$(CR^eR^f)_r$—$C(O)OR^a$, —$(CR^eR^f)_r$—$C(O)N(R^b)(R^c)$, —$(CR^eR^f)_r$—$N(R^b)(R^c)$, —$(CR^eR^f)_r$—$N(R^b)C(O)R^a$, —$(CR^eR^f)_r$—$N(R^b)S(O)_2R^d$, —$(CR^eR^f)_r$—$N(R^b)C(O)O(R^a)$, —$(CR^eR^f)_r$—$N(R^b)C(O)N(R^b)(R^c)$, —$(CR^eR^f)_r$-$G^1$, —$(CR^eR^f)_r$—CN, and haloalkyl;

$R^2$ is alkyl, alkenyl, alkynyl, $G^2$, —$C(O)R^a$, —$S(O)_2$—$R^d$, —O(G), —O—$(CR^eR^f)_r$-$G^1$, —$(CR^eR^f)_s$—O-$G^1$, $(CR^eR^f)_s$—O—$(CR^eR^f)_r$-$G^1$, —$(CR^eR^f)_r$—$C(O)$—$R^a$, —$(CR^eR^f)_r$—SO—$R^d$, —$(CR^eR^f)_s$—$N(R^b)(R^c)$, —$(CR^eR^f)_r$-$G^2$, —$(CR^eR^f)_r$-$G^3$, —$(CR^eR^f)_s$—$N(R^b)SO_2R^d$, —$(CR^eR^f)_s$—$N(R^b)COR^a$, —$(CR^eR^f)_s$—$N(R^b)CON(R^b)(R^c)$, —$(CR^eR^f)_s$—$N(R^b)$ $SO_2N(R^b)(R^c)$, —$(CR^eR^f)_r$—$SO_2N(R^b)(R^c)$, —$(CR^eR^f,$ —$C(O)N(R^b)(R^c)$, —$(CR^eR^f)_r$—CN, haloalkyl, or haloalkoxyalkyl;

$R^3$ and $R^4$, together with the atoms to which they are attached, form a 6-membered monocyclic heterocycle; wherein said monocyclic heterocycle contains one oxygen atom, zero or one nitrogen atom, and zero or one additional double bond; two non-adjacent atoms of said monocyclic heterocycle are linked by an alkenylene bridge of 2 carbon atoms, or are linked by an alkylene bridge of 2 carbon atoms, wherein one of the methylene groups of the alkenylene or the alkylene bridge can be optionally replaced by O, S, S(O), $S(O)_2$, N(H), or N(alkyl); said monocyclic heterocycle can be unsubstituted or substituted with 1, 2, 3, 4, or 5 substituents independently selected from the group consisting of oxo, alkyl, halogen, —OH, —O(alkyl), and haloalkyl;

$R^a$, $R^c$, and $R^{c1}$, at each occurrence, are each independently hydrogen, alkyl, haloalkyl, alkoxyalkyl, haloalkoxyalkyl, $G^1$, or —$(CR^eR^f)_r$-$G^1$;

$R^b$ and $R^{b1}$, at each occurrence, are each independently hydrogen, alkyl, haloalkyl, alkoxyalkyl, cycloalkyl, or haloalkoxyalkyl;

$R^{b1}$ and $R^{c1}$, together with the nitrogen atom to which they are both attached optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo;

$R^d$, at each occurrence, is independently alkyl, haloalkyl, alkoxyalkyl, cyanoalkyl, $G^1$, or —$(CR^eR^f)_r$-$G^1$;

$R^e$ and $R^f$, at each occurrence, are each independently hydrogen, alkyl, halogen, or haloalkyl;

r, at each occurrence, is independently 1, 2, 3, 4, 5, or 6;

s, at each occurrence, is independently 2, 3, 4, 5, or 6;

$G^1$, at each occurrence, is independently aryl, heteroaryl, cycloalkyl, cycloalkenyl, or heterocycle;

$G^2$, at each occurrence, is independently aryl, heteroaryl, cycloalkyl, or cycloalkenyl;

$G^3$, is a monocyclic heterocycle containing 1 or 2 nitrogen atoms and 0 or 1 sulfur atom;

wherein the rings as represented by $G^1$, $G^2$, or $G^3$ are each independently unsubstituted or substituted with 1, 2, 3, 4, or 5 substituents independently selected from the group consisting of alkyl, alkenyl, alkynyl, halogen, =N—CN, =N—$OR^n$, —CN, oxo, —$NO_2$, —$OR^m$, —$OC(O)R^m$, —$OC(O)N(R^m)_2$, —$SR^m$, —$S(O)_2R^n$, —$S(O)_2N(R^m)_2$, —$C(O)R^m$, —$C(O)OR^m$, —$C(O)N(R^m)_2$, —$N(R^m)_2$, —$N(R^m)C(O)R^m$, —$N(R^m)S(O)_2R^n$, —$N(R^m)C(O)O(R^m)$, —$N(R^m)C(O)N(R^m)_2$, —$(CR^eR^f)_r$—$NO_2$, —$(CR^eR^f)_r$—$OR^m$, —$(CR^eR^f)_r$—$OC(O)R^m$, —$(CR^eR^f)_r$—$OC(O)N(R^m)_2$, —$(CR^eR^f)_r$—$SR^m$, —$(CR^eR^f)_r$—$S(O)_2R^n$, —$(CR^eR^f)_r$—$S(O)_2N(R^m)_2$, —$(CR^eR^f)_r$—$C(O)R^m$, —$(CR^eR^f)_r$—$C(O)OR^m$, —$(CR^eR^f)_r$—$C(O)N(R^m)_2$, —$(CR^eR^f)_r$—$N(R^m)_2$, —(CR$^e$R$^f$)$_r$—N(R$'''$)C(O)R$'''$, —(CR$^e$R$^f$)$_r$—N(R$'''$)S(O)$_2$R$''$, —(CR$^e$R$^f$)$_r$—N(R$'''$)C(O)O(R$'''$), —(CR$^e$R$^f$)N(R$'''$)C(O)N(R$'''$)$_2$, —(CR$^e$R$^f$)$_r$—CN, and haloalkyl;

R$'''$, at each occurrence, is independently hydrogen, alkyl, haloalkyl, alkoxyalkyl, cycloalkyl, or haloalkoxyalkyl; two R$'''$ when attached to the same nitrogen atom optionally form a 4-7 membered monocyclic heterocycle; wherein said monocyclic heterocycle contains 0 or 1 additional heteroatom, 0 or 1 double bond, and is optionally substituted with 1, 2, or 3 substituents independently selected from the group consisting of alkyl, alkoxy, haloalkyl, halo, hydroxy, and oxo; and R$''$, at each occurrence, is independently alkyl, haloalkyl, cycloalkyl, cycloalkylalkyl, alkoxyalkyl, or cyanoalkyl, wherein the compound is not a solvate.

16. The compound according to claim 15, wherein
R$^2$ is C$_3$-C$_7$ alkyl or —(CH$_2$)-G$^2$; and
G$^2$ is C$_3$-C$_6$ cycloalkyl.

17. The compound according to claim 15, wherein the compound is selected from the group consisting of:
N-[(2Z)-3-butyl-3,4,7,8-tetrahydro-2H-4,7-epoxycyclohepta[d][1,3]thiazol-2-ylidene]-5-chloro-2-methoxybenzamide, and
N-[(2Z)-3-butyl-3,4,5,6,7,8-hexahydro-2H-4,7-epoxycyclohepta[d][1,3]thiazol-2-ylidene]-5-chloro-2-methoxybenzamide,
or a pharmaceutically acceptable salt thereof.

18. A pharmaceutical composition comprising a therapeutically effective amount of a compound of formula (I) according to claim 15, or a pharmaceutically acceptable salt thereof, in combination with a pharmaceutically acceptable carrier.

19. A compound selected from the group consisting of:
N-[(2Z)-3-butyl-4,4,6,6-tetramethyl-4,6-dihydrofuro[3,4-d][1,3]thiazol-2(3H)-ylidene]-5-chloro-2-methoxybenzamide,
N-[(2Z)-1-butyl-4,4-dimethyl-1,4,6,7-tetrahydro-2H-pyrano[4,3-d][1,3]thiazol-2-ylidene]-5-chloro-2-methoxybenzamide,
5-chloro-N-[(2Z)-1-(cyclobutylmethyl)-4,4-dimethyl-1,4,6,7-tetrahydro-2H-pyrano[4,3-d][1,3]thiazol-2-ylidene]-2-methoxybenzamide,
N-[(2Z)-3-butyl-6,6-dimethyl-4-oxo-4,6-dihydrofuro[3,4-d][1,3]thiazol-2(3H)-ylidene]-5-chloro-2-methoxybenzamide,
5-chloro-N-[(2Z)-3-(cyclobutylmethyl)-6,7-dihydro-4H-pyrano[3,4-d][1,3]thiazol-2(3H)-ylidene]-2-methoxybenzamide,
N-[(2Z)-3-butyl-7-hydroxy-6,7-dihydro-4H-pyrano[3,4-d][1,3]thiazol-2(3H)-ylidene]-5-chloro-2-methoxybenzamide,
N-[(2Z)-3-butyl-7-hydroxy-7-methyl-6,7-dihydro-4H-pyrano[3,4-d][1,3]thiazol-2(3H)-ylidene]-5-chloro-2-methoxybenzamide,
N-[(2Z)-3-butyl-4,6-dihydrofuro[3,4-d][1,3]thiazol-2(3H)-ylidene]-5-chloro-2-methoxybenzamide,
5-chloro-N-[(2Z)-3-(cyclobutylmethyl)-4,6-dihydrofuro[3,4-d][1,3]thiazol-2(3H)-ylidene]-2-methoxybenzamide,
5-chloro-N-[(2Z)-1-(cyclobutylmethyl)-1,4,6,7-tetrahydro-2H-pyrano[4,3-d][1,3]thiazol-2-ylidene]-2-methoxybenzamide,
N-[(2Z)-1-butyl-1,4,6,7-tetrahydro-2H-pyrano[4,3-d][1,3]thiazol-2-ylidene]-5-chloro-2-methoxybenzamide,
5-chloro-N-[(2Z)-1-isobutyl-1,4,6,7-tetrahydro-2H-pyrano[4,3-d][1,3]thiazol-2-ylidene]-2-methoxybenzamide,
N-[(2Z)-1-butyl-1,4,6,7-tetrahydro-2H-pyrano[4,3-d][1,3]thiazol-2-ylidene]-5-cyano-2-methoxybenzamide, and
N-[(2Z)-1-butyl-6,7-dihydro-5H-pyrano[3,2-d][1,3]thiazol-2(1H)-ylidene]-5-chloro-2-methoxybenzamide,
or a pharmaceutically acceptable salt thereof.

20. A pharmaceutical composition comprising a therapeutically effective amount of a compound of claim 19, or a pharmaceutically acceptable salt thereof, in combination with a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,735,434 B2 | Page 1 of 1 |
| APPLICATION NO. | : 12/120969 | |
| DATED | : May 27, 2014 | |
| INVENTOR(S) | : Carroll | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this
Eleventh Day of August, 2015

Michelle K. Lee
*Director of the United States Patent and Trademark Office*